US012721812B2

(12) United States Patent
Perreault et al.

(10) Patent No.: US 12,721,812 B2
(45) Date of Patent: Sep. 1, 2026

(54) METHOD FOR STIMULATING T CELL RESPONSE AGAINST LYMPHOBLASTIC LEUKEMIA WITH LEUKEMIA TUMOR SPECIFIC ANTIGENS

(71) Applicant: UNIVERSITE DE MONTREAL, Montreal (CA)

(72) Inventors: Claude Perreault, Montreal (CA); Pierre Thibault, Montreal (CA); Marie-Pierre Hardy, Terrebonne (CA)

(73) Assignee: UNIVERSITE DE MONTREAL, Montreal (CA)

( * ) Notice: Subject to any disclaimer, the term of this patent is extended or adjusted under 35 U.S.C. 154(b) by 765 days.

(21) Appl. No.: 17/916,545

(22) PCT Filed: Apr. 9, 2021

(86) PCT No.: PCT/CA2021/050471

§ 371 (c)(1),
(2) Date: Sep. 30, 2022

(87) PCT Pub. No.: WO2021/207826

PCT Pub. Date: Oct. 21, 2021

(65) Prior Publication Data

US 2023/0158132 A1 May 25, 2023

Related U.S. Application Data

(60) Provisional application No. 63/009,796, filed on Apr. 14, 2020.

(51) Int. Cl.

| | |
|---|---|
| ***A61P 35/00*** | (2006.01) |
| ***A61K 9/127*** | (2025.01) |
| ***A61K 39/00*** | (2006.01) |
| ***A61K 45/06*** | (2006.01) |

(52) U.S. Cl.

CPC .......... *A61K 9/127* (2013.01); *A61K 39/0011* (2013.01); *A61K 45/06* (2013.01); *A61P 35/00* (2018.01); *A61K 2039/5154* (2013.01)

(58) Field of Classification Search

CPC ........................ A61K 39/0011; C07K 14/4748
See application file for complete search history.

(56) References Cited

FOREIGN PATENT DOCUMENTS

| | | | |
|---|---|---|---|
| WO | 2017036936 | A1 | 3/2017 |
| WO | 2017097602 | A1 | 6/2017 |
| WO | 2018189152 | A2 | 10/2018 |
| WO | 2020041876 | A1 | 3/2020 |

OTHER PUBLICATIONS

Janelle, V, et al., "T-Cell Immunotherapies Targeting Histocompatibility and Tumor Antigens in Hematological Malignancies", Frontiers in Immunology 11, 276, 1-15 (2020).
Rui, C, et al., "Identification of MHC Peptides Using Mass Spectrometry for Neoantigen Discovery and Cancer Vaccine Development", Mass Spectrometry reviews DOI:10.1002/mas, 1-16 (2019).
Bassani-Sternberg, M , et al., "Direct identification of clinically relevant neoepitopes presented on native human melanoma tissue by mass spectrometry", Nature Communications 7, 13404, doi:10.1038/ncomms13404, 16 pages (2016).
Biernacki, M. , et al., "Neoantigens in Hematologic Malignancies", Frontiers in Immunology 11(121), 1-14 (2020).
Bilich, T , et al., "The HLA ligandome landscape of chronic myeloid leukemia delineates novel T-cell epitopes for immunotherapy", Blood 133(6), 550-565 (2019).
Blum, J. , et al., "Pathways of Antigen Processing", Annual Review of Immunology 31, 443-473 (2013).
Bray, N. , et al., "Near-optimal probabilistic rna-seq quantification", Nature Biotechnology 34(5), 525-528 (2016).
Caron, E , et al., "Analysis of Major Histocompatibility Complex (MHC) Immunopeptidomes Using Mass Spectrometry", Molecular & Cellular Proteomics 14, 3105-3117 (2015).
Courcelles, M. , et al., "MAPDP: A Cloud-Based Computational Platform for Immunopeptidomics Analyses", Journal of Proteome Res 19, 1873-1881 (2020).
Davis, M. , et al., "T Cells as a Self-Referential Sensory Organ", Annu. Rev. Immunol 25, 681-695 (2007).
Douglass, J. , et al., "Bispecific antibodies targeting mutant RAS neoantigens", Sci. Immunol 6(57), doi:10.1126/sciimmunol.abd5515, 29 pages (2021).
Ehx, G. , et al., "Atypical acute myeloid leukemia-specilc transcripts generate shared and immunogenic MHC class-I-associated epitopes", Immunity 54, 737-752 (2021).
Ehx, G , et al., "Discovery and characterization of actionable tumor antigens", Genome Medicine 11(29), 3 pages (2019).
Garrison, E , et al., "Haplotype-based variant detection from short-read sequencing", arXiv:1207.3907v2[q-bio.GN], 9 pages (2012).
Genomes Project Consortium , "A map of human genome variation from population-scale sequencing", Nature 467 (7319), 1061-1073 (2010).
Granados, D , et al., "Impact of genomic polymorphisms on the repertoire of human MHC class I-associated peptides", Nature Communications 5, 3600, 14 pages (2014).
Granados, D. , et al., "MHC I-associated peptides preferentially derive from transcripts bearing miRNA response elements", Blood 119(26), e181-e191 (2012).
Grandados, D. , et al., "Proteogenomic-based discovery of minor histocompatibility antigens with suitable features for immunotherapy of hematologic cancers", Leukemia 30, 1344-1354 (2016).

(Continued)

*Primary Examiner* — Elly-Gerald Stoica
(74) *Attorney, Agent, or Firm* — Viksnins Harris Padys Malen LLP

(57) ABSTRACT

Acute lymphoblastic leukemia (ALL) has not benefited from innovative immunotherapies, mainly because of the lack of actionable immune targets. Novel tumor-specific antigens (TSAs) specifically expressed by ALL cells are described herein. Most of the TSAs described herein derives from aberrantly expressed unmutated genomic sequences, such as intronic and intergenic sequences, which are not expressed in normal tissues. Nucleic acids, compositions, cells, antibodies and vaccines derived from these TSAs are described. The use of the TSAs, nucleic acids, compositions, antibodies, cells and vaccines for the treatment of leukemia such as ALL is also described.

12 Claims, 19 Drawing Sheets

Specification includes a Sequence Listing.

(56) References Cited

OTHER PUBLICATIONS

Grandados, D. , et al., "The nature of self for T cells—a systems-level perspective", Current Opinion in Immunology 34, 1-8 (2015).
Hoare, H. , et al., "Structural basis for a major histocompatibility complex class lb-restricted T cell response", Nature Immunology 7(3), 256-264 (2006).
Hisiue, E. , et al., "Targeting a neoantigen derived from a common TP53 mutation", Science 371(6533), doi: 10.1126/science.abc8697, 31 pages (2021).
Hunt, S. , et al., "Ensembl variation resources", Database 2108, article ID bay119; doi:10.1093/database/bay119, 12 pages (2018).
Lanoix, J , et al., "Comparison of the MHC I Immunopeptidome Repertoire of B-Cell Lymphoblasts Using Two Isolation Methods", Proteomics 18, 1700251, 13 pages (2018).
Laumont, C. , et al., "Exploiting non-canonical translation to identify new targets for T cell-based cancer immunotherapy", Cell Mol Life Sci 75, 607-621 (2018).
Laumont, C , et al., "Noncoding regions are the main source of targetable tumor-specific antigens", Sci Transl Med 10, eaau5516, 11 pages (2018).
Liepe, J. , et al., "A large fraction of HLA class I ligands are proteasome-generated spliced peptides", Science 354 (6310), 354-358 (2016).
McAlister, G. , et al., "MultiNotch MS3 Enables Accurate, Sensitive, and Multiplexed Detection of Differential Expression across Cancer Cell Line Proteomes", Analytical Chemistry 86, 7150-7158 (2014).
Mommen, G. , et al., "Expanding the detectable HLA peptide repertoire using electron-transfer/higher-energy collision dissociation (EThcD)", PNAS 111(12) 4507-4512 (2014).
Murata, S. , et al., "The immunoproteasome and thymoproteasome: functions, evolution and human disease", Nature Immunology 19, 923-931 (2018).
Murphy, P. , et al., "MHC-I Ligand Discovery Using Targeted Database Searches of Mass Spectrometry Data: Implications for T-Cell Immunotherapies", Journal of Proteome Res16, 1806-1816 (2017).
Murphy, P. , et al., "Multiplexed Relative Quantitation with Isobaric Tagging Mass Spectrometry Reveals Class I Major Histocompatibility Complex Ligand Dynamics in Response to Doxorubicin", Anal. Chem. 91(8), 5106-5115 (2019).
Neefjes, J. , et al., "Towards a systems understanding of MHC class I and MHC class II antigen presentation", Immunology 11, 823-836 (2011).
Patent Cooperation Treaty , International Search Report and Written Opinion for PCT/CA2021/050471, 20 pages, dated Jun. 18, 2021.
Pearson, H , et al., "MHC class-associated peptides derive from selective regions of the human genome", J Clin Invest 126(12), 4690-4701 (2016).
Perez-Riverol, Y , et al., "The PRIDE database and related tools and resources in 2019: improving support for quantification data", Nucleic Acids Research 47, D442-D450 (2019).
Pfammatter, S. , et al., "A Novel Differential Ion Mobility Device Expands the Depth of Proteome Coverage and the Sensitivity of Multiplex Proteomic Measurements", Molecular & Cellular Proteomics 17(10), 2051-2067 (2018).
Pfammatter, S. , et al., "Improvement of Quantitative Measurements in Multiplex Proteomics Using High-Field Asymmetric Waveform Spectrometry", Journal of Proteome Res 15, 4653-4665 (2016).
Robinson, J. , et al., "Distinguishing Functional Polymorphism from random variation in the sequences of >10,000 HLA-A, -B and -C Alleles", PLOS Genetics https:doi.org/10.1371/journal.pgen.1006862, 1-28 (2017).
Robinson, J. , et al., "The IPD and IMGT/HLA database: allele variant databases", Nucleic Acids Research 43, D423-D431 (2015).
Roche, P. , et al., "The ins and outs of MHC class II-mediated antigen processing and presentation", Immunology 15, 203-216 (2015).
Rock, K. , et al., "Present Yourself! By MHC Class I and MHC Class II Molecules", Trends in Immunology 37(11), 724-737 (2016).
Roopenian, D. , et al., "The immunogenomics of minor histocompatibility antigens", Immunological Reviews 190, 86-94 (2002).
Shraibman, B. , et al., "Identification of Tumor Antigens Among the HLA Peptidomes of Glioblastoma Tumors and Plasma", Molecular & Cellular Proteomics 18, 1255-1268 (2019).
Spierings, E , et al., "Phenotype Frequencies of Autosomal Minor Histocompatibility Antigens Display Significant Differences among Populations", PLoS Genetics 3(6), 1108-1119 (2007).
Thompson, A. , et al., "Tandem Mass Tags: A Novel Quantification Strategy for Comparative Analysis of Complex Protein Mixtures by MS/MS", Anal. Chem. 75, 1895-1904 (2003).
Thomsen, M. , et al., "MHCcluster, a method for functional clustering of MHC molecules", Immunogenetics 65(9), 655-665 (2013).
Tsai, C. , et al., "Tandem Mass Tag Labeling Facilitates Reversed-Phase Liquid Chromatography-Mass Spectrometry Analysis of Hydrophilic Phosphopeptides", Anal Chem 91(18), 11606-11613 (2019).
Weinzierl, A. , et al., "Distorted Relation between mRNA Copy Number and Corresponding Major Histocompatibility Complex Ligand Density on the Cell Surface", Molecular & Cellular Proteomics 6, 102-113 (2007).
Yang, X. , et al., "Opportunities and Challenges for Antibodies against Intracellular Antigens", Theranostics 9(25), 7792-7806 (2019).
Zecha, J. , et al., "TMT Labeling for the Masses: A Robust and Cost-efficient, In-solution Labeling Approach", Molecular & Cellular Proteomics 18, 1468-1478 (2019).
Croft, et al., "Most viral peptides displayed by class I MHC on infected cells are immunogenic", PNAS 116 (8), 3112-3117 (2019).
European Examination Report, for EP Application No. 21789353.6, 7 pages, dated Oct. 17, 2025.
Klein, et al., "Positive and negative selection of the T cell repertoire: what thymocytes see and don't see", Nat Rev Immunol 14 (6), 377-391 (2014).
Lu, et al., "Tumor Neoantigenicity Assessment with CSIN Score Incorporates Clonality and Immunogenicity to Predict Immunotherapy Outcomes", Sci Immunol 5 (44), 24 pages (2020).
Mirabile-Brightman, et al., "Advances in the development of personalized neoantigen therapies", J Exp Med 223 (2), e20241234, 1-14 (2026).
Nguyen, et al., "Neoantigen-based mRNA vaccine exhibits superior anti-tumor activity compared to synthetic long peptides in an in vivo lung carcinoma model", Cancer Immunology, Immunotherapy 74, 145, 17 pages (2025).
Ruiz Cuevas, et al., "BamQuery: a proteogenomic tool to explore the immunopeptidome and prioritize actionable tumor antigens", Genome Biology 24 (188), 1-33 (2023).
Sette, et al., "The Relationship Between Class I Binding Affinity and Immunogenicity of Potential Cytotoxic T Cell Epitopes", The Journal of Immunology 153, 5586-5592, 9 pages (1994).

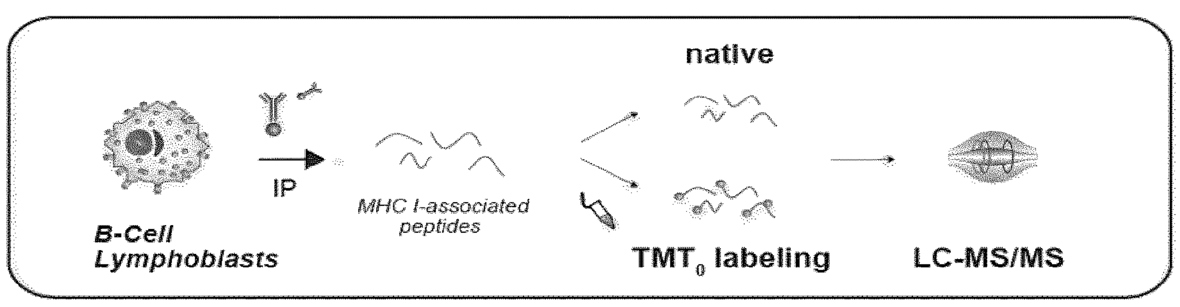
FIG. 1A
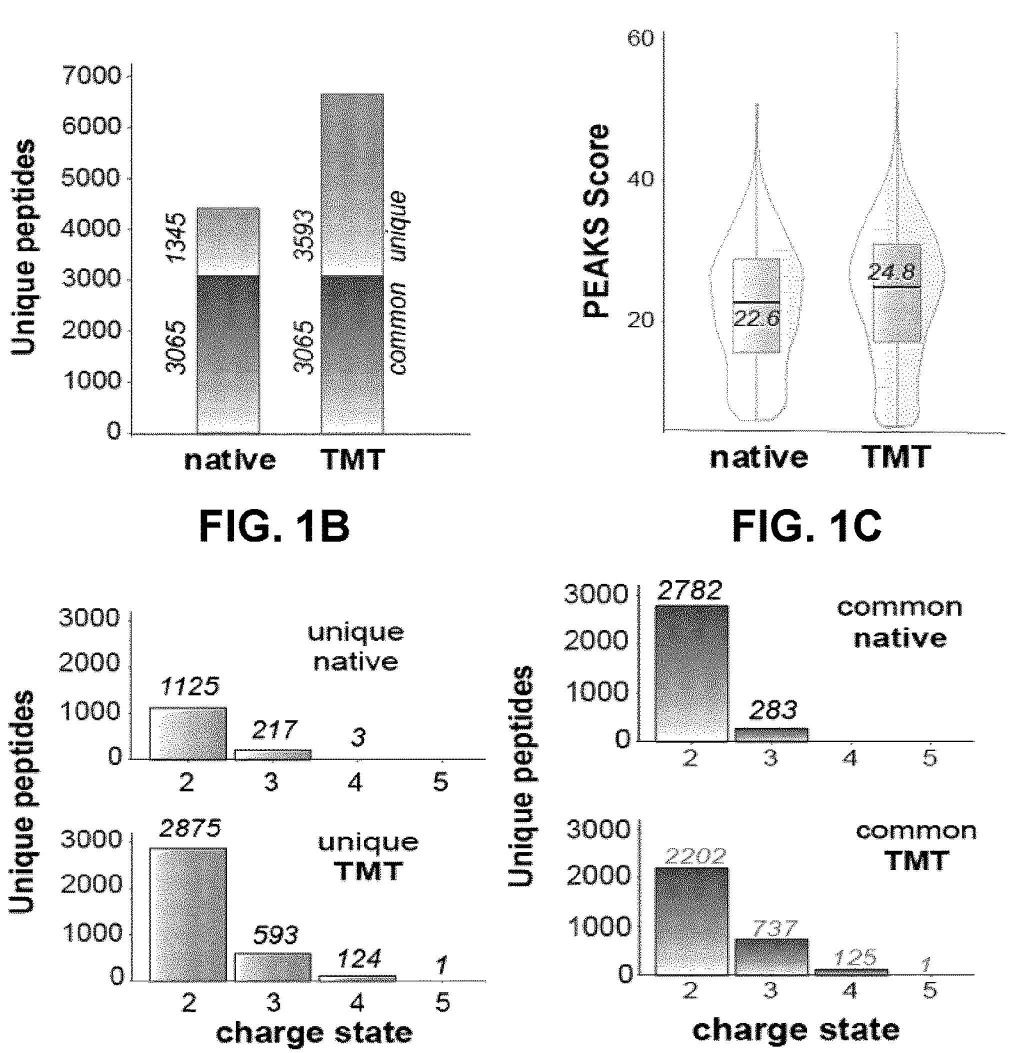
FIG. 1B
FIG. 1C
FIG. 1D

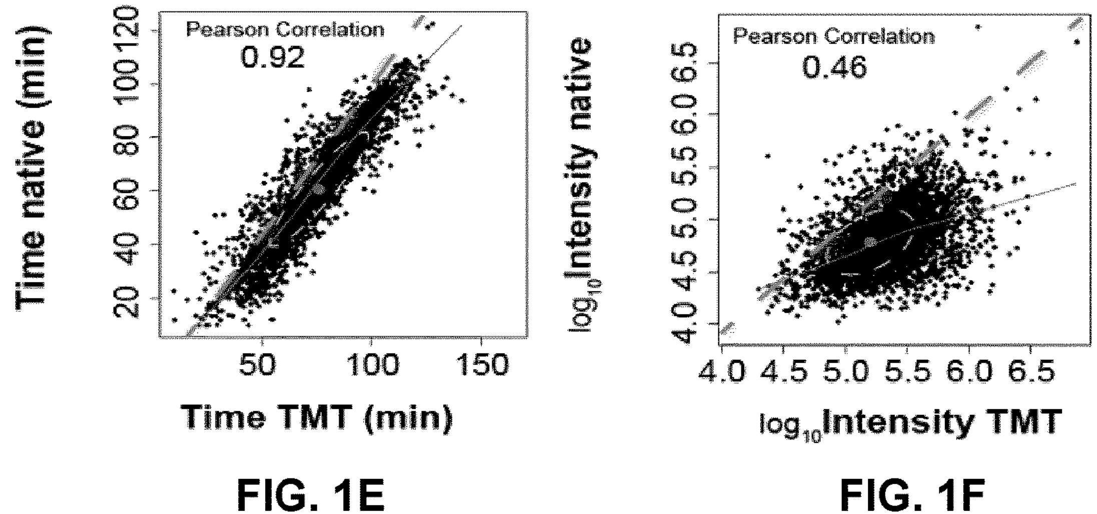
FIG. 1E
FIG. 1F
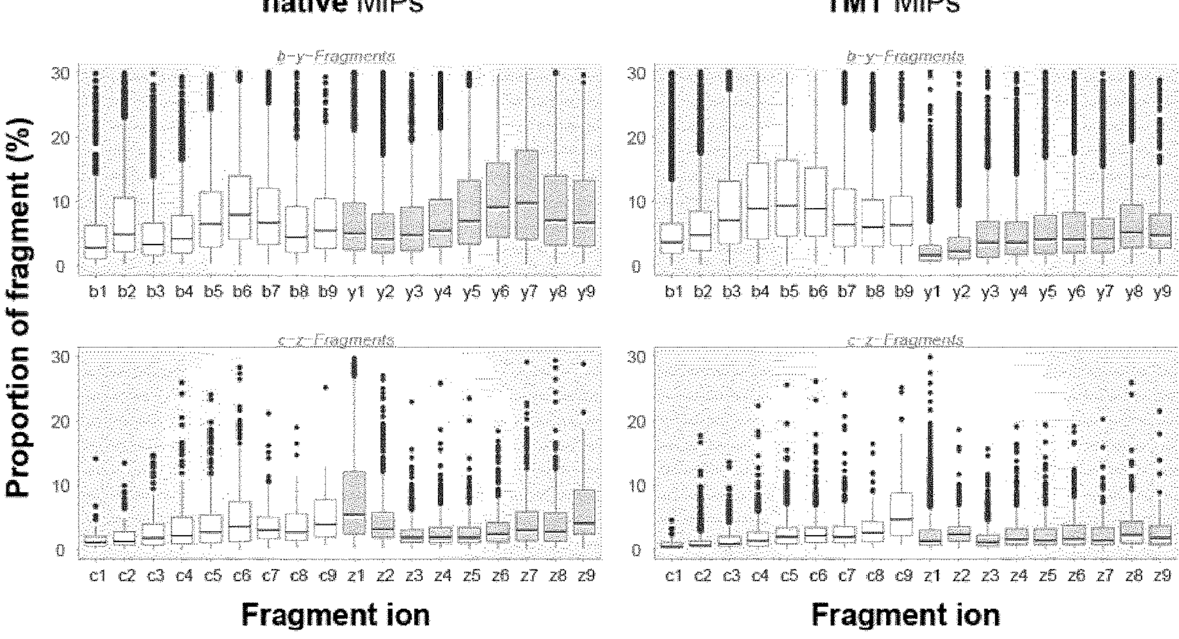
FIG. 2A

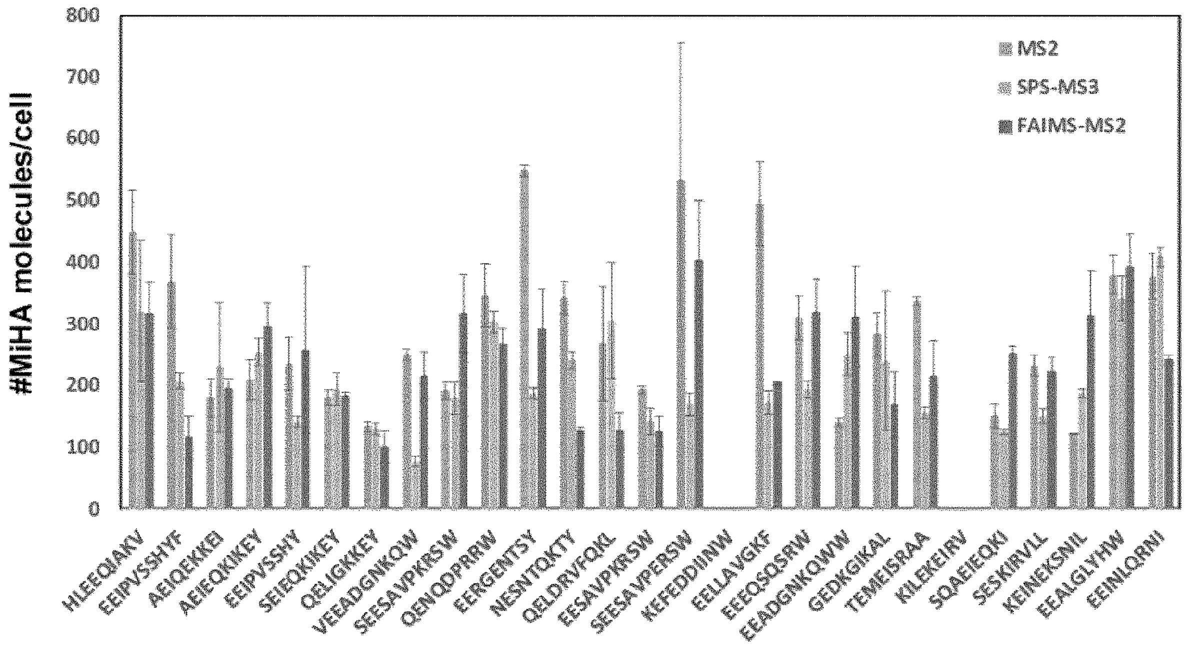
FIG. 5B
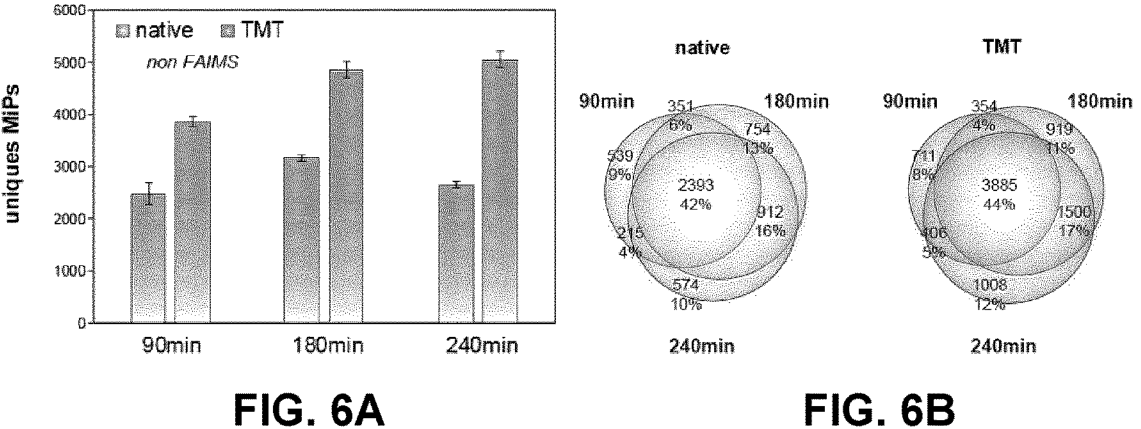
FIG. 6A
FIG. 6B

ALFSNEVSL / 2+

*SynthPeptides_MHC_200220_4.raw* [25035] (*Synthetic − top*)

*20Mio_BALL_TMT_nonFAIMS_Rep1.raw* [15953] (*Endogenous − bottom*)

$m_{theo} = 1202.6546$, $m_{endo} = 1202.6556(0.83\,ppm)$, $m_{syn} = 1202.6516(0.8\,ppm)$ $r = 0.78$, $P < 2.86e-06$, 95% *CI* 0.56 *to* 0.90

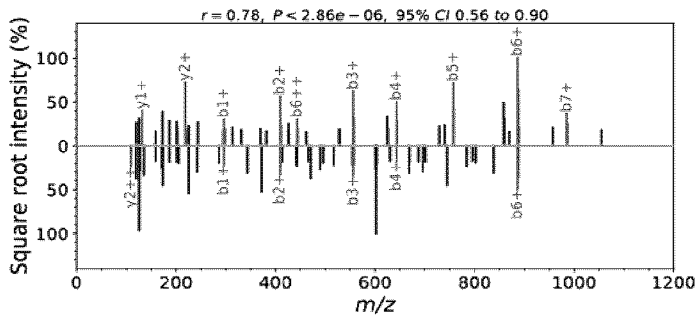

FIPDLFTEL / 2+

*SynthPeptides_MHC_200220_6.raw* [25900] (*Synthetic − top*)

*100Mio_BALL_TMT_nonFAIMS_Rep1.raw* [38351] (*Endogenous − bottom*)

$m_{theo} = 1317.7220$, $m_{endo} = 1317.7230(0.76\,ppm)$, $m_{syn} = 1317.7256(5.5\,ppm)$ $r = 0.97$, $P < 1.66e-15$, 95% *CI* 0.92 *to* 0.98

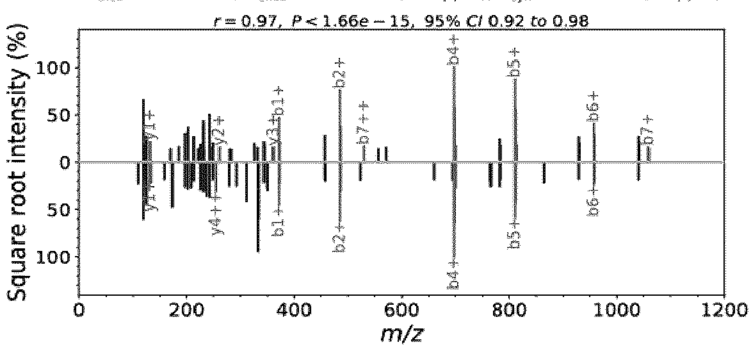

FLLPTSLSL / 2+

*SynthPeptides_MHC_200220_6.raw* [23003] (*Synthetic − top*)

*100Mio_BALL_TMT_nonFAIMS_Rep2.raw* [33678] (*Endogenous − bottom*)

$m_{theo} = 1213.7321$, $m_{endo} = 1213.7308(-1.07\,ppm)$, $m_{syn} = 1213.7350(5.1\,ppm)$ $r = 0.96$, $P < 4.45e-15$, 95% *CI* 0.91 *to* 0.98

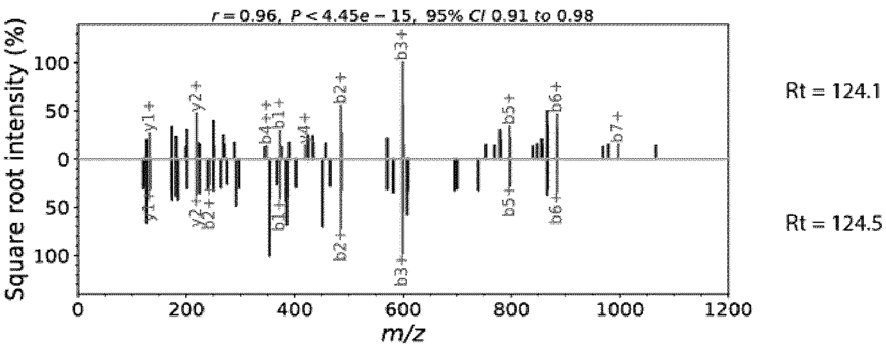

GEVDGAQQAM / 2+

*SynthPeptides_MHC_200220_6.raw* [6877] (*Synthetic* − *top*)

*100Mio_BALL_TMT_nonFAIMS_Rep3.raw* [8163] (*Endogenous* − *bottom*)

$m_{theo}$ = 1228.5758, $m_{endo}$ = 1228.5780(1.84 *ppm*), $m_{syn}$ = 1228.5800(6.2 *ppm*)

*r* = 0.83, *P* < 5.51e − 10, 95% *CI* 0.69 to 0.91

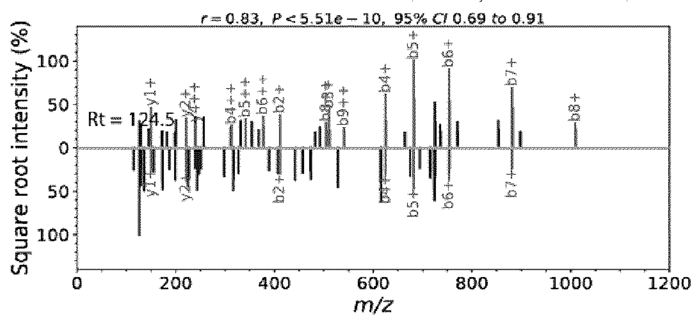

GLATAVWLL / 2+

*SynthPeptides_MHC_020320_1.raw* [23016] (*Synthetic* − *top*)

*100Mio_BALL_TMT_nonFAIMS_Rep3.raw* [35794] (*Endogenous* − *bottom*)

$m_{theo}$ = 1166.7062, $m_{endo}$ = 1166.7074(1.03 *ppm*), $m_{syn}$ = 1166.7124(5.3 *ppm*)

*r* = 0.95, *P* < 5.40e − 13, 95% *CI* 0.89 to 0.98

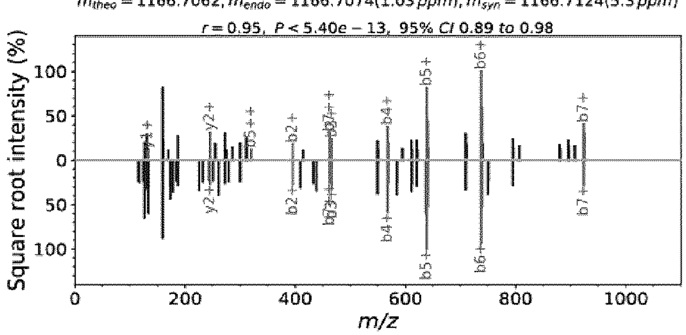

GTLCLLTFI / 2+

*SynthPeptides_MHC_200220_6.raw* [25127] (*Synthetic* − *top*)

*100Mio_BALL_TMT_nonFAIMS_Rep1.raw* [35376] (*Endogenous* − *bottom*)

$m_{theo}$ = 1203.6936, $m_{endo}$ = 1203.6962(2.16 *ppm*), $m_{syn}$ = 1203.6916(1.1 *ppm*)

*r* = 0.91, *P* < 2.12e − 09, 95% *CI* 0.79 to 0.96

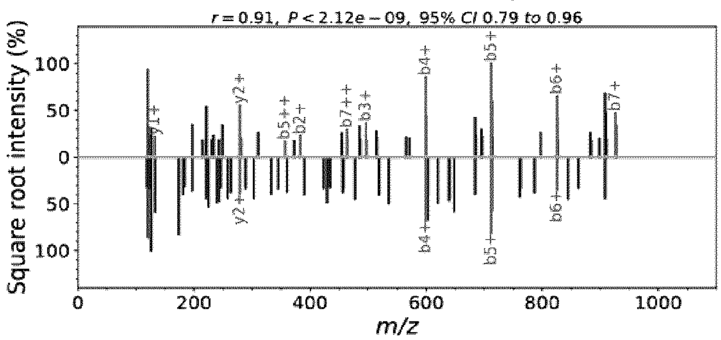

GVANSLLK / 2+

*SynthPeptides_MHC_200220_2.raw* [7863] (*Synthetic* − *top*)

100*Mio_BALL_TMT_nonFAIMS_Rep2.raw* [14458] (*Endogenous* − *bottom*)

$m_{theo} = 1248.7804, m_{endo} = 1248.7826(1.76\,ppm), m_{syn} = 1248.7806(2.9\,ppm)$ $r = 0.92,\ P < 2.03e-09,\ 95\%\ CI\ 0.81\ to\ 0.97$

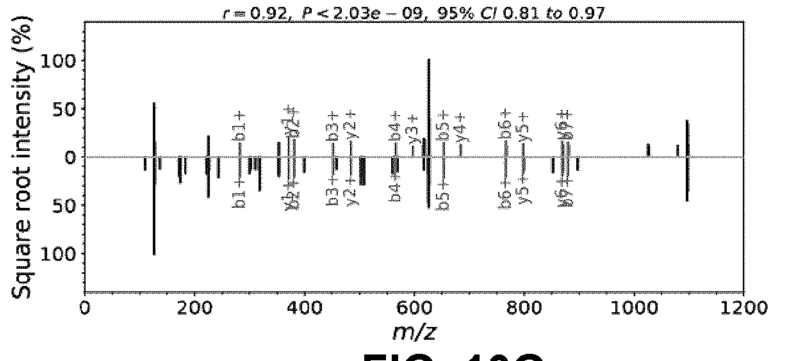

FIG. 10G

GVSPVLFLK / 2+

*SynthPeptides_MHC_200220_2.raw* [12066] (*Synthetic* − *top*)

100*Mio_BALL_TMT_nonFAIMS_Rep1.raw* [28216] (*Endogenous* − *bottom*)

$m_{theo} = 1406.8901, m_{endo} = 1406.8934(2.37\,ppm), m_{syn} = 1406.8882(1.5\,ppm)$ $r = 0.96,\ P < 8.25e-14,\ 95\%\ CI\ 0.90\ to\ 0.98$

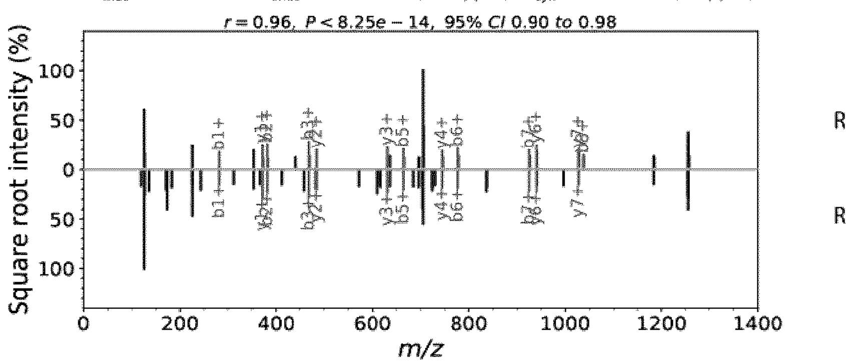

FIG. 10H

IDPFHFLK / 2+

*SynthPeptides_MHC_200220_2.raw* [11101] (*Synthetic* − *top*)

20*Mio_BALL_native_nonFAIMS_Rep1.raw* [14225] (*Endogenous* − *bottom*)

$m_{theo} = 1015.5490, m_{endo} = 1015.5440(-4.91\,ppm), m_{syn} = 1015.5456(-0.5\,ppm)$ $r = 0.08,\ P < 7.02e-01,\ 95\%\ CI\ -0.33\ to\ 0.47$

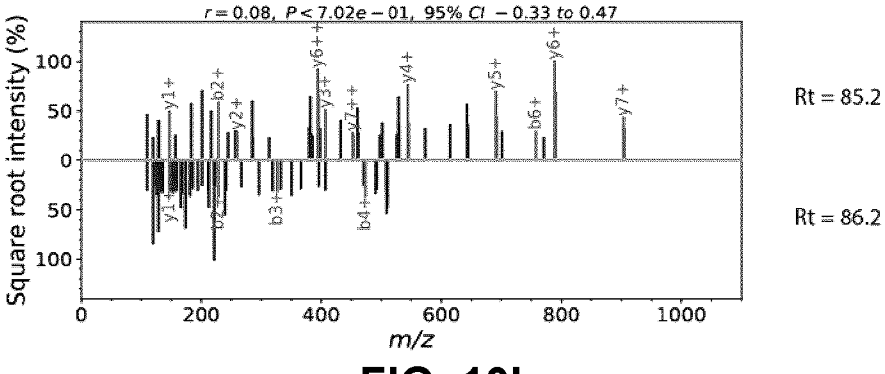

FIG. 10I

LLSLYLVSI / 2+

*SynthPeptides_MHC_200220_6.raw* [25179] (*Synthetic − top*)

100*Mio_BALL_TMT_nonFAIMS_Rep3.raw* [37373] (*Endogenous − bottom*)

$m_{theo}$ = 1243.7791, $m_{endo}$ = 1243.7788(−0.24 *ppm*), $m_{syn}$ = 1243.7764(0.5 *ppm*)

*r* = 0.92, *P* < 2.15e − 09, 95% *CI* 0.82 *to* 0.97

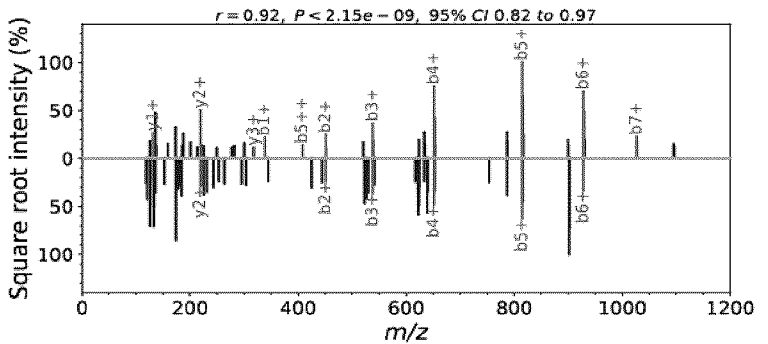

LSQPLPPGFK / 2+

*SynthPeptides_MHC_200220_5.raw* [11071] (*Synthetic − top*)

100*Mio_BALL_native_nonFAIMS_Rep1.raw* [12958] (*Endogenous − bottom*)

$m_{theo}$ = 1082.6124, $m_{endo}$ = 1082.6146(2.03 *ppm*), $m_{syn}$ = 1082.6122(2.6 *ppm*)

*r* = 0.85, *P* < 6.96e − 07, 95% *CI* 0.66 *to* 0.93

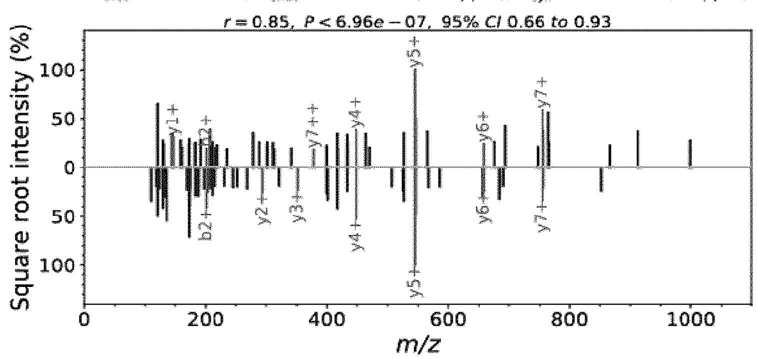

LSSRLPLGK / 3+

*SynthPeptides_MHC_200220_6.raw* [12693] (*Synthetic − top*)

20*Mio_BALL_TMT_nonFAIMS_Rep2.raw* [10651] (*Endogenous − bottom*)

$m_{theo}$ = 1417.9022, $m_{endo}$ = 1417.9036(0.99 *ppm*), $m_{syn}$ = 1417.8976(−0.5 *ppm*)

*r* = 0.62, *P* < 1.43e − 04, 95% *CI* 0.35 *to* 0.80

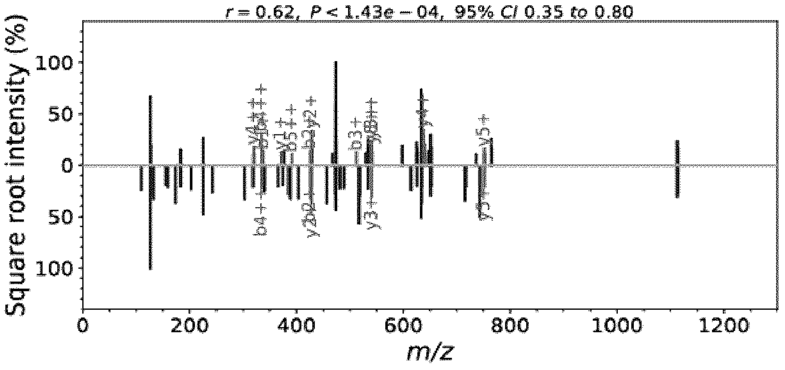

SERDQGTTL / 2+

*SynthPeptides_MHC_200220_3.raw* [2972] (*Synthetic – top*)

*100Mio_BALL_native_nonFAIMS_Rep1.raw* [3588] (*Endogenous – bottom*)

$m_{theo} = 1005.4726, m_{endo} = 1005.4764(3.77\ ppm), m_{syn} = 1005.4790(9.1\ ppm)$ $r = 0.84,\ P < 3.99e-10,\ 95\%\ CI\ 0.70\ to\ 0.91$

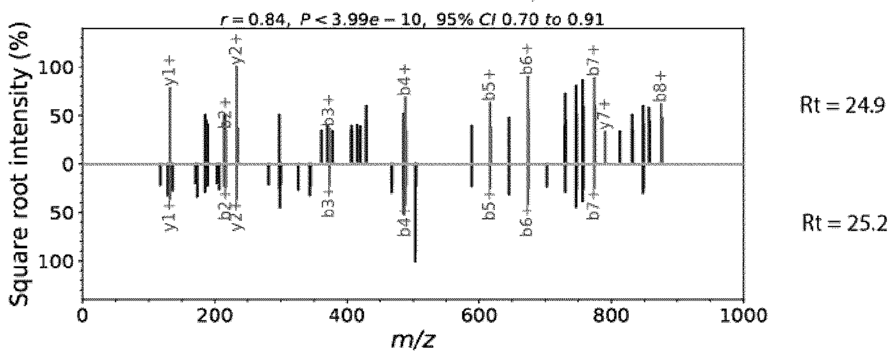

FIG. 10S

SLLGIGLLA / 2+

*SynthPeptides_MHC_200220_6.raw* [21387] (*Synthetic – top*)

*60Mio_BALL_TMT_nonFAIMS_Rep1.raw* [28709] (*Endogenous – bottom*)

$m_{theo} = 1079.6954, m_{endo} = 1079.6966(1.11\ ppm), m_{syn} = 1079.6926(0.2\ ppm)$ $r = 0.92,\ P < 3.63e-10,\ 95\%\ CI\ 0.81\ to\ 0.96$

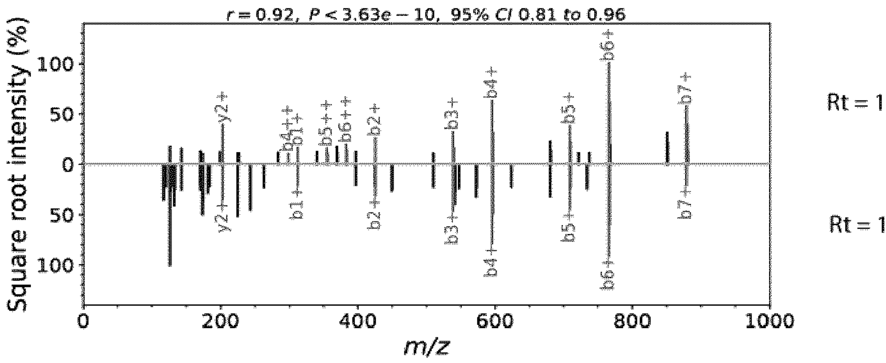

FIG. 10T

SLTALVFHV / 2+

*SynthPeptides_MHC_200220_5.raw* [16037] (*Synthetic – top*)

*20Mio_BALL_TMT_nonFAIMS_Rep3.raw* [20058] (*Endogenous – bottom*)

$m_{theo} = 1209.7121, m_{endo} = 1209.7126(0.43\ ppm), m_{syn} = 1209.7136(4.0\ ppm)$ $r = 0.88,\ P < 1.87e-10,\ 95\%\ CI\ 0.77\ to\ 0.94$

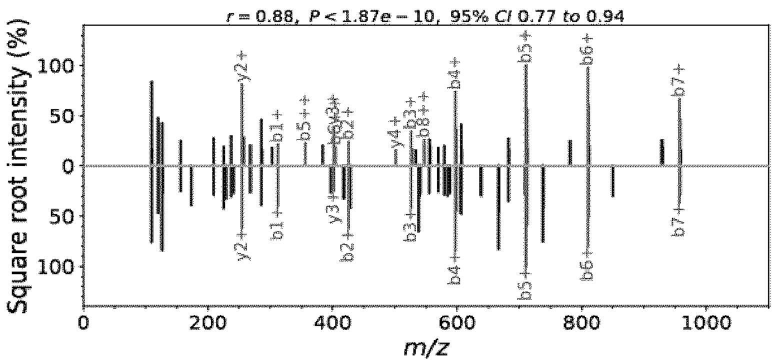

FIG. 10U

METHOD FOR STIMULATING T CELL RESPONSE AGAINST LYMPHOBLASTIC LEUKEMIA WITH LEUKEMIA TUMOR SPECIFIC ANTIGENS

CROSS-REFERENCE TO RELATED APPLICATIONS

This application is a 35 U.S.C § 371 application of International Application No. PCT/CA2021/050471, filed on Apr. 9, 2021, which claims priority to U.S. Provisional Application No. 63/009,796, filed on Apr. 14, 2020. The contents of each of these applications are incorporated by reference herein. The present applicant claims the benefits of U.S. provisional patent application No. 63/009,796 filed on Apr. 14, 2020, which is incorporated herein by reference in its entirety.

TECHNICAL FIELD

The present invention generally relates to cancer, and more specifically to tumor antigens specific for acute lymphoblastic leukemia useful for T-cell-based cancer immunotherapy.

BACKGROUND ART

Acute lymphoblastic leukemia (ALL), a malignant transformation and proliferation of lymphoid progenitor cells in the bone marrow, blood and extramedullary sites, is the second most common acute leukemia in adults. Although most (about 80%) ALL cases occur in children, it represents a devastating disease when it occurs in adults. While dose-intensification strategies have led to a significant improvement in outcomes for pediatric patients, prognosis for the elderly remains very poor, with only 30-40% of adult patients with ALL achieving long-term remission.

The structure of treatment of adult ALL has been adapted from pediatric protocols. Unfortunately, while long-term survival approaches 90% for standard-risk pediatric ALL, the success rate is much more modest in adults. Chemotherapy consists of induction, consolidation and long-term maintenance, with CNS prophylaxis given at intervals throughout therapy. The goal of induction therapy is to achieve complete remission and to restore normal hematopoiesis. The backbone of induction therapy typically includes vincristine, corticosteroids and an anthracycline. After induction, eligible patients may go on to Allo-SCT while all others go on to intensification/consolidation and maintenance.

While 85-90% of patients go into remission after induction therapy, there are subsets that are refractory to induction therapy. In addition, a majority of patients that do achieve CR go on to relapse. Options of salvage therapy for relapsed/refractory (r/r) Ph-negative disease include augmented cytotoxic chemotherapy, reformulated single-agent chemotherapy and novel monoclonal antibodies. In patients with relapsed/refractory Ph-negative B-ALL, a bispecific antibody that targets both CD3 and CD19 has a reported complete remission rate of 67%, but it is also associated with adverse effects such as cytokine release syndrome (CRS), high fever, nausea, headaches, and hepatic and neurologic side effects. A monoclonal antibody against CD22, inotuzumab, is also approved for the treatment of Ph-negative ALL. Genetically engineered T cells expressing a chimeric antigen receptor (CAR-T) targeting CD19 and CD22 present on ALL blasts have generated promising results in children and adults with relapsed and refractory disease. However, these therapies are only effective against $CD19^+$ and/or $CD22^+$ malignancies, and are associated with adverse effects as noted above.

The use of T-cell based immunotherapy targeting tumor antigens could provide an alternative therapeutic option, but the nature of ALL antigens able to elicit protective immune responses remains elusive.

In view of this, there is a pressing need to identify the tumor-specific antigens that can elicit therapeutic immune responses again ALL. Such antigens could be used as vaccines (±immune checkpoint inhibitors) or as targets for T-cell receptor-based approaches (cell therapy, bispecific biologics).

The present description refers to a number of documents, the content of which is herein incorporated by reference in their entirety.

SUMMARY OF THE INVENTION

The present disclosure provides the following items 1 to 72:

1. A leukemia tumor antigen peptide (TAP) comprising one of the following amino acid sequences:

| Sequence | SEQ ID NO: | Sequence | SEQ ID NO: | Sequence | SEQ ID NO: |
|---|---|---|---|---|---|
| NEQTTILY | 1 | LLGLPQPPK | 31 | GEFLVPLSL | 61 |
| ALFSNEVSL | 2 | LSSRLPLGK | 32 | GEVDGAQQAM | 62 |
| FIPDLFTEL | 3 | NLLFSRVFK | 33 | IEEVSQGLL | 63 |
| FLLDHILTI | 4 | STGVLTVLK | 34 | IESEDFGFWSL | 64 |
| FLLESRETL | 5 | SVFDRTNNR | 35 | LENSGFILI | 65 |
| FLLPTSLSL | 6 | SVVPHPLQK | 36 | REPLEILITL | 66 |
| FLLSDELLL | 7 | TTSSIYIRK | 37 | EETDAYKSL | 67 |
| GLATAVWLL | 8 | LYTFIKHEF | 38 | SELQLPVTF | 68 |
| GLLTASIFL | 9 | SYFDPSYSNF | 39 | QEIATSHNI | 69 |
| GTLCLLTFI | 10 | SYLASFLLY | 40 | AQFLLFIA | 70 |
| KLLQPLPIT | 11 | VYSPSPLNF | 41 | FEISSVTTA | 71 |
| LLQNLIVLL | 12 | VYTQVSAF | 42 | KEVGGLRSA | 72 |
| LLSLYLVSI | 13 | YSVLTVTF | 43 | TEFGPVIG | 73 |
| LMLLFVVLL | 14 | NLGLFLSY | 44 | ISLPALEVL | 74 |
| SLANETHTL | 15 | AVGGFRSSW | 45 | LPSPPLPPSL | 75 |
| VLLDFPALL | 16 | SQVQAVLLAW | 46 | LYLPSVVLI | 76 |
| VLLSKILYP | 17 | QTNSGSLAR | 47 | RPPAPLLPVL | 77 |
| WLVEKLSGV | 18 | DVAGVGMPK | 48 | SLHYSVSL | 78 |
| YLFAHSIIL | 19 | DVMASLARV | 49 | SLPDHQGVL | 79 |
| YLGYAVAV | 20 | EVGAVFAVL | 50 | EAVSQGKDF | 80 |
| YLQEISLRL | 21 | VVADILLSV | 51 | YSSYLSIHY | 81 |
| SLLGIGLLA | 22 | SSLSGPVSSL | 52 | ASLGLSLAL | 82 |
| AAMESPIQSK | 23 | AFRVIVAL | 53 | LCHRTPPSL | 83 |

-continued

| Sequence | SEQ ID NO: | Sequence | SEQ ID NO: | Sequence | SEQ ID NO: |
|---|---|---|---|---|---|
| ALFGFVGFPNK | 24 | EHYNKVVVM | 54 | LSISPFQAI | 84 |
| ALFVLTSIK | 25 | VQAQVLEAI | 55 | GWGGSPLYL | 85 |
| ATSLTIQEK | 26 | NNMAIIYSY | 56 | YFDPSYSNF | 86 |
| AVAVPLLPR | 27 | EPSHSINVY | 57 | ISLSSIVSV | 87 |
| GTISGGFFK | 28 | IPVGSGLGYVL | 58 | LSISSLVSV | 88 |
| GVANSLLK | 29 | DHDIGVYSV | 59 | | |
| GVSPVLFLK | 30 | HFEWQPPL | 60 | | |

2. The leukemia TAP of item 1, wherein said leukemia TAP binds to an HLA-A*01:01 molecule and comprises the amino acid sequence of SEQ ID NO: 1.

3. The leukemia TAP of item 1, wherein said leukemia TAP binds to an HLA-A*02:01 molecule and comprises the amino acid sequence of any one of SEQ ID NOs: 2-22.

4. The leukemia tumor antigen peptide of item 1, wherein said leukemia tumor antigen peptide binds to an HLA-A*11:01 molecule and comprises the amino acid sequence of any one of SEQ ID NOs: 23-37.

5. The leukemia TAP of item 1, wherein said leukemia TAP binds to an HLA-24*:02 molecule and comprises the amino acid sequence of any one of SEQ ID NOs: 38-43.

6. The leukemia TAP of item 1, wherein said leukemia TAP binds to an HLA-A*29:02 molecule and comprises the amino acid sequence of SEQ ID NO: 44.

7. The leukemia TAP of item 1, wherein said leukemia TAP binds to an HLA-A*32:01 molecule and comprises the amino acid sequence of SEQ ID NO: 45 or 46.

8. The leukemia TAP of item 1, wherein said leukemia TAP binds to an HLA-A*66:01 molecule and comprises the amino acid sequence of SEQ ID NO: 47.

9. The leukemia TAP of item 1, wherein said leukemia TAP binds to an HLA-A*68:01 molecule and comprises the amino acid sequence of SEQ ID NO: 48.

10. The leukemia TAP of item 1, wherein said leukemia TAP binds to an HLA-A*68:02 molecule and comprises the amino acid sequence of any one of SEQ ID NOs: 49-51.

11. The leukemia TAP of item 1, wherein said leukemia TAP binds to an HLA-B*07:02 molecule and comprises the amino acid sequence of SEQ ID NO: 52.

12. The leukemia TAP of item 1, wherein said leukemia TAP binds to an HLA-B*08:01 molecule and comprises the amino acid sequence of SEQ ID NO:53.

13. The leukemia TAP of item 1, wherein said leukemia TAP binds to an HLA-B*14:02 molecule and comprises the amino acid sequence of SEQ ID NO: 54.

14. The leukemia TAP of item 1, wherein said leukemia TAP binds to an HLA-B*15:10 molecule and comprises the amino acid sequence of SEQ ID NO: 55.

15. The leukemia TAP of item 1, wherein said leukemia TAP binds to an HLA-B*18:01 molecule and comprises the amino acid sequence of SEQ ID NO: 56.

16. The leukemia TAP of item 1, wherein said leukemia TAP binds to an HLA-B*35:01 molecule and comprises the amino acid sequence of SEQ ID NO: 57 or 58.

17. The leukemia TAP of item 1, wherein said leukemia TAP binds to an HLA-B*39:01 molecule and comprises the amino acid sequence of SEQ ID NO: 59 or 60.

18. The leukemia TAP of item 1, wherein said leukemia TAP binds to an HLA-B*40:01 molecule and comprises the amino acid sequence of any one of SEQ ID NOs: 61-66.

19. The leukemia TAP of item 1, wherein said leukemia TAP binds to an HLA-B*44:02 molecule and comprises the amino acid sequence of SEQ ID NO: 67 or 68.

20. The leukemia TAP of item 1, wherein said leukemia TAP binds to an HLA-B*49:01 molecule and comprises the amino acid sequence of SEQ ID NO: 69.

21. The leukemia TAP of item 1, wherein said leukemia TAP binds to an HLA-B*50:01 molecule and comprises the amino acid sequence of any one of SEQ ID NOs: 70-73.

22. The leukemia TAP of item 1, wherein said leukemia TAP binds to an HLA-C*01:02 molecule and comprises the amino acid sequence of any one of SEQ ID NOs: 74-79.

23. The leukemia TAP of item 1, wherein said leukemia TAP binds to an HLA-C*02:02 molecule and comprises the amino acid sequence of SEQ ID NO: 80 or 81.

24. The leukemia TAP of item 1, wherein said leukemia TAP binds to an HLA-C*03:04 molecule and comprises the amino acid sequence of any one of SEQ ID NOs: 82-84.

25. The leukemia TAP of item 1, wherein said leukemia TAP binds to an HLA-C*04:01 molecule and comprises the amino acid sequence of SEQ ID NO: 85 or 86.

26. The leukemia TAP of item 1, wherein said leukemia TAP binds to an HLA-C*15:02 molecule and comprises the amino acid sequence of SEQ ID NO: 87 or 88.

27. The leukemia TAP of any one of items 1-26, which is encoded by a sequence located a non-protein coding region of the genome.

28. The leukemia TAP of item 27, wherein said non-protein coding region of the genome is an untranslated transcribed region (UTR).

29. The leukemia TAP of item 27, wherein said non-protein coding region of the genome is an intron.

30. The leukemia TAP of item 27, wherein said non-protein coding region of the genome is an intergenic region.

31. The leukemia TAP of item 27, wherein said non-protein coding region of the genome is a long non-coding RNAs 32. A combination comprising at least two of the leukemia TAPs defined in any one of items 1-31.

33. A nucleic acid encoding the leukemia TAP of any one of items 1-31 or the combination of item 32.

34. The nucleic acid of item 33, which is an mRNA or a viral vector.

35. A liposome comprising the leukemia TAP of any one of items 1-31, the combination of item 32, or the nucleic acid of item 33 or 34.

36. A composition comprising the leukemia TAP of any one of items 1-31, the combination of item 32, the nucleic acid of item 33 or 34, or the liposomes of item 35, and a pharmaceutically acceptable carrier.

37. A vaccine comprising the leukemia TAP of any one of items 1-31, the combination of item 32, the nucleic acid of item 33 or 34, the liposomes of item 35, or the composition of item 36, and an adjuvant.

38. An isolated major histocompatibility complex (MHC) class I molecule comprising the leukemia TAP of any one of items 1-31 in its peptide binding groove.

39. The isolated MHC class I molecule of item 38, which is in the form of a multimer.

40. The isolated MHC class I molecule of item 39, wherein said multimer is a tetramer.

41. An isolated cell comprising (i) the leukemia TAP of any one of items 1-31, (ii) the combination of item 32 or (iii) a vector comprising a nucleotide sequence encoding TAP of any one of items 1-31 or the combination of item 32.

42. An isolated cell expressing at its surface major histocompatibility complex (MHC) class I molecules comprising the leukemia TAP of any one of items 1-8 or the combination of item 9 in their peptide binding groove.

43. The cell of item 42, which is an antigen-presenting cell (APC).

44. The cell of item 43, wherein said APC is a dendritic cell.

45. A T-cell receptor (TCR) that specifically recognizes the isolated MHC class I molecule of any one of items 38-40 and/or MHC class I molecules expressed at the surface of the cell of any one of items 42-44.

46. An antibody or an antigen-binding fragment thereof that specifically binds to the isolated MHC class I molecule of any one of items 38-40 and/or MHC class I molecules expressed at the surface of the cell of any one of items 42-44.

47. The antibody or antigen-binding fragment thereof according to item 46, which is a bispecific antibody or antigen-binding fragment thereof.

48. The antibody or antigen-binding fragment thereof according to item 47, wherein the bispecific antibody or antigen-binding fragment thereof is a single-chain diabody (scDb).

49. The antibody or antigen-binding fragment thereof according to item 47 or 48, wherein the bispecific antibody or antigen-binding fragment thereof also specifically binds to a T cell signaling molecule.

50. The antibody or antigen-binding fragment thereof according to item 49, wherein the T cell signaling molecule is a CD3 chain.

51. An isolated cell expressing at its cell surface the TCR of item 45.

52. The isolated cell of item 51, which is a $CD8^+$ T lymphocyte.

53. A cell population comprising at least 0.5% of the isolated cell as defined in item 51 or 52.

54. A method of treating lymphoblastic leukemia in a subject comprising administering to the subject an effective amount of:

(i) a leukemia tumor antigen peptide (TAP) comprising one of the following amino acid sequences:

| Sequence | SEQ ID NO: | Sequence | SEQ ID NO: | Sequence | SEQ ID NO: |
|---|---|---|---|---|---|
| NEQTTILY | 1 | LLGLPQPPK | 31 | GEFLVPLSL | 61 |
| ALFSNEVSL | 2 | LSSRLPLGK | 32 | GEVDGAQQAM | 62 |
| FIPDLFTEL | 3 | NLLFSRVFK | 33 | IEEVSQGLL | 63 |
| FLLDHILTI | 4 | STGVLTVLK | 34 | IESEDFGFWSL | 64 |
| FLLESRETL | 5 | SVFDRTNNR | 35 | LENSGFILI | 65 |
| FLLPTSLSL | 6 | SVVPHPLQK | 36 | REPLEILITL | 66 |
| FLLSDELLL | 7 | TTSSIYIRK | 37 | EETDAYKSL | 67 |
| GLATAVWLL | 8 | LYTFIKHEF | 38 | SELQLPVTF | 68 |
| GLLTASIFL | 9 | SYFDPSYSNF | 39 | QEIATSHNI | 69 |
| GTLCLLTFI | 10 | SYLASFLLY | 40 | AQFLLFIA | 70 |
| KLLQPLPIT | 11 | VYSPSPLNF | 41 | FEISSVTTA | 71 |
| LLQNLIVLL | 12 | VYTQVSAF | 42 | KEVGGLRSA | 72 |
| LLSLYLVSI | 13 | YSVLTVTF | 43 | TEFGPVIG | 73 |

-continued

| Sequence | SEQ ID NO: | Sequence | SEQ ID NO: | Sequence | SEQ ID NO: |
|---|---|---|---|---|---|
| LMLLFVVLL | 14 | NLGLFLSY | 44 | ISLPALEVL | 74 |
| SLANETHTL | 15 | AVGGFRSSW | 45 | LPSPPLPPSL | 75 |
| VLLDFPALL | 16 | SQVQAVLLAW | 46 | LYLPSVVLI | 76 |
| VLLSKILYP | 17 | QTNSGSLAR | 47 | RPPAPLLPVL | 77 |
| WLVEKLSGV | 18 | DVAGVGMPK | 48 | SLHYSVSL | 78 |
| YLFAHSIIL | 19 | DVMASLARV | 49 | SLPDHQGVL | 79 |
| YLGYAVAV | 20 | EVGAVFAVL | 50 | EAVSQGKDF | 80 |
| YLQEISLRL | 21 | VVADILLSV | 51 | YSSYLSIHY | 81 |
| SLLGIGLLA | 22 | SSLSGPVSSL | 52 | ASLGLSLAL | 82 |
| AAMESPIQSK | 23 | AFRVIVAL | 53 | LCHRTPPSL | 83 |
| ALFGFVGFPNK | 24 | EHYNKVVVM | 54 | LSISPFQAI | 84 |
| ALFVLTSIK | 25 | VQAQVLEA1 | 55 | GWGGSPLYL | 85 |
| ATSLTIQEK | 26 | NNMAIIYSY | 56 | YFDPSYSNF | 86 |
| AVAVPLLPR | 27 | EPSHSINVY | 57 | ISLSSIVSV | 87 |
| GTISGGFFK | 28 | IPVGSGLGYVL | 58 | LSISSLVSV | 88 |
| GVANSLLK | 29 | DHDIGVYSV | 59 | IPLNPFSSL | 92 |
| GVSPVLFLK | 30 | HFEWQPPL | 60 | | |

(ii) a combination comprising at least two of the leukemia TAP defined in (i);

(iii) one or more nucleic acids encoding the leukemia TAP defined in (i) or the combination defined in (ii);

(iv) a liposome comprising the leukemia TAP defined in (i), the combination defined in (ii);

or the one or more nucleic acids defined in (iii);

(v) a composition comprising the leukemia TAP defined in (i), the combination defined in (ii); the one or more nucleic acids defined in (iii) or the liposomes defined in (iv);

(vi) a vaccine comprising the leukemia TAP defined in (i), the combination defined in (ii); the one or more nucleic acids defined in (iii) the liposomes defined in (iv) or the composition defined in (v); and an adjuvant;

(vii) a cell comprising the leukemia TAP defined in (i), the combination defined in (ii); or the one or more nucleic acids defined in (iii), or expressing at its surface major histocompatibility complex (MHC) class I molecules comprising the leukemia TAP defined in (i) or the combination defined in (ii) in their peptide binding groove;

(viii) a cell or cell population expressing at its surface a TCR that specifically recognizes MHC class I molecules comprising the leukemia TAP defined in (i) or the combination defined in (ii) in their peptide binding groove; or (ix) an antibody or an antigen-binding fragment thereof that specifically recognizes MHC class I molecules comprising the leukemia TAP defined in (i) or the combination defined in (ii) in their peptide binding groove.

55. The method of item 49, wherein the leukemia TAP is as defined in any one of items 1 to 31, the combination is as defined in item 32, the nucleic acid is as defined in item 33 or 34, the liposome is as defined in item 35, the composition is as defined in item 36, the vaccine is as defined in item 37, the cell is as defined in any one of items 41-44, 51 and 52, the cell population is as defined in item 53, and/or the antibody or antigen-binding fragment is as defined in any one of items 46-50.

56. The method of item 54 or 55, wherein said lymphoblastic leukemia is acute lymphoblastic leukemia (ALL).

57. The method of item 56, wherein the ALL is B-ALL.

58. The method of any one of items 54-57, further comprising administering at least one additional antitumor agent or therapy to the subject.

59. The method of item 58, wherein said at least one additional antitumor agent or therapy is a chemotherapeutic agent, immunotherapy, an immune checkpoint inhibitor, radiotherapy or surgery.

60. Use of:

(i) a leukemia tumor antigen peptide (TAP) comprising one of the following amino acid sequences:

| Sequence | SEQ ID NO: | Sequence | SEQ ID NO: | Sequence | SEQ ID NO: |
|---|---|---|---|---|---|
| NEQTTILY | 1 | LLGLPQPPK | 31 | GEFLVPLSL | 61 |
| ALFSNEVSL | 2 | LSSRLPLGK | 32 | GEVDGAQQAM | 62 |
| FIPDLFTEL | 3 | NLLFSRVFK | 33 | IEEVSQGLL | 63 |
| FLLDHILTI | 4 | STGVLTVLK | 34 | IESEDFGFWSL | 64 |
| FLLESRETL | 5 | SVFDRTNNR | 35 | LENSGFILI | 65 |
| FLLPTSLSL | 6 | SVVPHPLQK | 36 | REPLEILITL | 66 |
| FLLSDELLL | 7 | TTSSIYIRK | 37 | EETDAYKSL | 67 |
| GLATAVWLL | 8 | LYTFIKHEF | 38 | SELQLPVTF | 68 |
| GLLTASIFL | 9 | SYFDPSYSNF | 39 | QEIATSHNI | 69 |
| GTLCLLTFI | 10 | SYLASFLLY | 40 | AQFLLFIA | 70 |
| KLLQPLPIT | 11 | VYSPSPLNF | 41 | FEISSVTTA | 71 |
| LLQNLIVLL | 12 | VYTQVSAF | 42 | KEVGGLRSA | 72 |
| LLSLYLVSI | 13 | YSVLTVTF | 43 | TEFGPVIG | 73 |
| LMLLFVVLL | 14 | NLGLFLSY | 44 | ISLPALEVL | 74 |
| SLANETHTL | 15 | AVGGFRSSW | 45 | LPSPPLPPSL | 75 |
| VLLDFPALL | 16 | SQVQAVLLAW | 46 | LYLPSVVLI | 76 |
| VLLSKILYP | 17 | QTNSGSLAR | 47 | RPPAPLLPVL | 77 |
| WLVEKLSGV | 18 | DVAGVGMPK | 48 | SLHYSVSL | 78 |
| YLFAHSIIL | 19 | DVMASLARV | 49 | SLPDHQGVL | 79 |
| YLGYAVAV | 20 | EVGAVFAVL | 50 | EAVSQGKDF | 80 |
| YLQEISLRL | 21 | VVADILLSV | 51 | YSSYLSIHY | 81 |
| SLLGIGLLA | 22 | SSLSGPVSSL | 52 | ASLGLSLAL | 82 |
| AAMESPIQSK | 23 | AFRVIVAL | 53 | LCHRTPPSL | 83 |
| ALFGFVGFPNK | 24 | EHYNKVVVM | 54 | LSISPFQAI | 84 |
| ALFVLTSIK | 25 | VQAQVLEAl | 55 | GWGGSPLYL | 85 |
| ATSLTIQEK | 26 | NNMAIIYSY | 56 | YFDPSYSNF | 86 |
| AVAVPLLPR | 27 | EPSHSINVY | 57 | ISLSSIVSV | 87 |
| GTISGGFFK | 28 | IPVGSGLGYVL | 58 | LSISSLVSV | 88 |
| GVANSLLK | 29 | DHDIGVYSV | 59 | IPLNPFSSL | 92 |
| GVSPVLFLK | 30 | HFEWQPPL | 60 | | |

(ii) a combination comprising at least two of the leukemia TAP defined in (i);

(iii) one or more nucleic acids encoding the leukemia TAP defined in (i) or the combination defined in (ii);

(iv) a liposome comprising the leukemia TAP defined in (i), the combination defined in (ii);

or the one or more nucleic acids defined in (iii);

(v) a composition comprising the leukemia TAP defined in (i), the combination defined in (ii); the one or more nucleic acids defined in (iii) or the liposomes defined in (iv);

(vi) a vaccine comprising the leukemia TAP defined in (i), the combination defined in (ii); the one or more nucleic acids defined in (iii) the liposomes defined in (iv) or the composition defined in (v); and an adjuvant;

(vii) a cell comprising the leukemia TAP defined in (i), the combination defined in (ii); or the one or more nucleic acids defined in (iii), or expressing at its surface major histocompatibility complex (MHC) class I molecules comprising the leukemia TAP defined in (i) or the combination defined in (ii) in their peptide binding groove;

(viii) a cell or cell population expressing at its surface a TCR that specifically recognizes MHC class I molecules comprising the leukemia TAP defined in (i) or the combination defined in (ii) in their peptide binding groove; or (ix) an antibody or an antigen-binding fragment thereof that specifically recognizes MHC class I molecules comprising the leukemia TAP defined in (i) or the combination defined in (ii) in their peptide binding groove;

for treating lymphoblastic lymphoblastic leukemia in a subject.

61. Use of:

(i) a leukemia tumor antigen peptide (TAP) comprising one of the following amino acid sequences:

| Sequence | SEQ ID NO: | Sequence | SEQ ID NO: | Sequence | SEQ ID NO: |
|---|---|---|---|---|---|
| NEQTTILY | 1 | LLGLPQPPK | 31 | GEFLVPLSL | 61 |
| ALFSNEVSL | 2 | LSSRLPLGK | 32 | GEVDGAQQAM | 62 |
| FIPDLFTEL | 3 | NLLFSRVFK | 33 | IEEVSQGLL | 63 |
| FLLDHILTI | 4 | STGVLTVLK | 34 | IESEDFGFWSL | 64 |
| FLLESRETL | 5 | SVFDRTNNR | 35 | LENSGFILI | 65 |
| FLLPTSLSL | 6 | SVVPHPLQK | 36 | REPLEILITL | 66 |
| FLLSDELLL | 7 | TTSSIYIRK | 37 | EETDAYKSL | 67 |

-continued

| Sequence | SEQ ID NO: | Sequence | SEQ ID NO: | Sequence | SEQ ID NO: |
|---|---|---|---|---|---|
| GLATAVWLL | 8 | LYTFIKHEF | 38 | SELQLPVTF | 68 |
| GLLTASIFL | 9 | SYFDPSYSNF | 39 | QEIATSHNI | 69 |
| GTLCLLTFI | 10 | SYLASFLLY | 40 | AQFLLFIA | 70 |
| KLLQPLPIT | 11 | VYSPSPLNF | 41 | FEISSVTTA | 71 |
| LLQNLIVLL | 12 | VYTQVSAF | 42 | KEVGGLRSA | 72 |
| LLSLYLVSI | 13 | YSVLTVTF | 43 | TEFGPVIG | 73 |
| LMLLFVVLL | 14 | NLGLFLSY | 44 | ISLPALEVL | 74 |
| SLANETHTL | 15 | AVGGFRSSW | 45 | LPSPPLPPSL | 75 |
| VLLDFPALL | 16 | SQVQAVLLAW | 46 | LYLPSVVLI | 76 |
| VLLSKILYP | 17 | QTNSGSLAR | 47 | RPPAPLLPVL | 77 |
| WLVEKLSGV | 18 | DVAGVGMPK | 48 | SLHYSVSL | 78 |
| YLFAHSIIL | 19 | DVMASLARV | 49 | SLPDHQGVL | 79 |
| YLGYAVAV | 20 | EVGAVFAVL | 50 | EAVSQGKDF | 80 |
| YLQEISLRL | 21 | VVADILLSV | 51 | YSSYLSIHY | 81 |
| SLLGIGLLA | 22 | SSLSGPVSSL | 52 | ASLGLSLAL | 82 |
| AAMESPIQSK | 23 | AFRVIVAL | 53 | LCHRTPPSL | 83 |
| ALFGFVGFPNK | 24 | EHYNKVVVM | 54 | LSISPFQAI | 84 |
| ALFVLTSIK | 25 | VQAQVLEAl | 55 | GWGGSPLYL | 85 |
| ATSLTIQEK | 26 | NNMAIIYSY | 56 | YFDPSYSNF | 86 |
| AVAVPLLPR | 27 | EPSHSINVY | 57 | ISLSSIVSV | 87 |
| GTISGGFFK | 28 | IPVGSGLGYVL | 58 | LSISSLVSV | 88 |
| GVANSLLK | 29 | DHDIGVYSV | 59 | IPLNPFSSL | 92 |
| GVSPVLFLK | 30 | HFEWQPPL | 60 | | |

(ii) a combination comprising at least two of the leukemia TAP defined in (i);

(iii) one or more nucleic acids encoding the leukemia TAP defined in (i) or the combination defined in (ii);

(iv) a liposome comprising the leukemia TAP defined in (i), the combination defined in (ii); or the one or more nucleic acids defined in (iii);

(v) a composition comprising the leukemia TAP defined in (i), the combination defined in (ii); the one or more nucleic acids defined in (iii) or the liposomes defined in (iv);

(vi) a vaccine comprising the leukemia TAP defined in (i), the combination defined in (ii); the one or more nucleic acids defined in (iii) the liposomes defined in (iv) or the composition defined in (v); and an adjuvant;

(vii) a cell comprising the leukemia TAP defined in (i), the combination defined in (ii); or the one or more nucleic acids defined in (iii), or expressing at its surface major histocompatibility complex (MHC) class I molecules comprising the leukemia TAP defined in (i) or the combination defined in (ii) in their peptide binding groove;

(viii) a cell or cell population expressing at its surface a TCR that specifically recognizes MHC class I molecules comprising the leukemia TAP defined in (i) or the combination defined in (ii) in their peptide binding groove; or (ix) an antibody or an antigen-binding fragment thereof that specifically recognizes MHC class I molecules comprising the leukemia TAP defined in (i) or the combination defined in (ii) in their peptide binding groove;

for the manufacture of a medicament for treating lymphoblastic leukemia in a subject.

62. The use of item 60 or 61, wherein the leukemia TAP is as defined in any one of items 1 to 31, the combination is as defined in item 32, the nucleic acid is as defined in item 33 or 34, the liposome is as defined in item 35, the composition is as defined in item 36, the vaccine is as defined in item 37, the cell is as defined in any one of items 41-44, 51 and 52, the cell population is as defined in item 53, and/or the antibody or antigen-binding fragment is as defined in any one of items 46-50.

63. The use of any one of items 60-62, wherein said lymphoblastic leukemia is acute lymphoblastic leukemia (ALL).

64. The use of item 63, wherein the ALL is B-ALL.

65. The use of any one of items 60-64, further comprising the use of at least one additional antitumor agent or therapy.

66. The use of item 65, wherein said at least one additional antitumor agent or therapy is a chemotherapeutic agent, immunotherapy, an immune checkpoint inhibitor, radiotherapy or surgery.

67. An agent for treating lymphoblastic leukemia in a subject, wherein the agent is:

(i) a leukemia tumor antigen peptide (TAP) comprising one of the following amino acid sequences:

| Sequence | SEQ ID NO: | Sequence | SEQ ID NO: | Sequence | SEQ ID NO: |
|---|---|---|---|---|---|
| NEQTTILY | 1 | LLGLPQPPK | 31 | GEFLVPLSL | 61 |
| ALFSNEVSL | 2 | LSSRLPLGK | 32 | GEVDGAQQAM | 62 |
| FIPDLFTEL | 3 | NLLFSRVFK | 33 | IEEVSQGLL | 63 |
| FLLDHILTI | 4 | STGVLTVLK | 34 | IESEDFGFWSL | 64 |
| FLLESRETL | 5 | SVFDRTNNR | 35 | LENSGFILI | 65 |
| FLLPTSLSL | 6 | SVVPHPLQK | 36 | REPLEILITL | 66 |
| FLLSDELLL | 7 | TTSSIYIRK | 37 | EETDAYKSL | 67 |
| GLATAVWLL | 8 | LYTFIKHEF | 38 | SELQLPVTF | 68 |
| GLLTASIFL | 9 | SYFDPSYSNF | 39 | QEIATSHNI | 69 |
| GTLCLLTFI | 10 | SYLASFLLY | 40 | AQFLLFIA | 70 |
| KLLQPLPIT | 11 | VYSPSPLNF | 41 | FEISSVTTA | 71 |
| LLQNLIVLL | 12 | VYTQVSAF | 42 | KEVGGLRSA | 72 |
| LLSLYLVSI | 13 | YSVLTVTF | 43 | TEFGPVIG | 73 |
| LMLLFVVLL | 14 | NLGLFLSY | 44 | ISLPALEVL | 74 |
| SLANETHTL | 15 | AVGGFRSSW | 45 | LPSPPLPPSL | 75 |
| VLLDFPALL | 16 | SQVQAVLLAW | 46 | LYLPSVVLI | 76 |
| VLLSKILYP | 17 | QTNSGSLAR | 47 | RPPAPLLPVL | 77 |

-continued

| Sequence | SEQ ID NO: | Sequence | SEQ ID NO: | Sequence | SEQ ID NO: |
|---|---|---|---|---|---|
| WLVEKLSGV | 18 | DVAGVGMPK | 48 | SLHYSVSL | 78 |
| YLFAHSIIL | 19 | DVMASLARV | 49 | SLPDHQGVL | 79 |
| YLGYAVAV | 20 | EVGAVFAVL | 50 | EAVSQGKDF | 80 |
| YLQEISLRL | 21 | VVADILLSV | 51 | YSSYLSIHY | 81 |
| SLLGIGLLA | 22 | SSLSGPVSSL | 52 | ASLGLSLAL | 82 |
| AAMESPIQSK | 23 | AFRVIVAL | 53 | LCHRTPPSL | 83 |
| ALFGFVGFPNK | 24 | EHYNKVVVM | 54 | LSISPFQAI | 84 |
| ALFVLTSIK | 25 | VQAQVLEAl | 55 | GWGGSPLYL | 85 |
| ATSLTIQEK | 26 | NNMAIIYSY | 56 | YFDPSYSNF | 86 |
| AVAVPLLPR | 27 | EPSHSINVY | 57 | ISLSSIVSV | 87 |
| GTISGGFFK | 28 | IPVGSGLGYVL | 58 | LSISSLVSV | 88 |
| GVANSLLK | 29 | DHDIGVYSV | 59 | IPLNPFSSL | 92 |
| GVSPVLFLK | 30 | HFEWQPPL | 60 | | |

(ii) a combination comprising at least two of the leukemia TAP defined in (i);

(iii) one or more nucleic acids encoding the leukemia TAP defined in (i) or the combination defined in (ii);

(iv) a liposome comprising the leukemia TAP defined in (i), the combination defined in (ii);

or the one or more nucleic acids defined in (iii);

(v) a composition comprising the leukemia TAP defined in (i), the combination defined in (ii); the one or more nucleic acids defined in (iii) or the liposomes defined in (iv);

(vi) a vaccine comprising the leukemia TAP defined in (i), the combination defined in (ii); the one or more nucleic acids defined in (iii) the liposomes defined in (iv) or the composition defined in (v); and an adjuvant;

(vii) a cell comprising the leukemia TAP defined in (i), the combination defined in (ii); or the one or more nucleic acids defined in (iii), or expressing at its surface major histocompatibility complex (MHC) class I molecules comprising the leukemia TAP defined in (i) or the combination defined in (ii) in their peptide binding groove;

(viii) a cell or cell population expressing at its surface a TCR that specifically recognizes MHC class I molecules comprising the leukemia TAP defined in (i) or the combination defined in (ii) in their peptide binding groove; or (ix) an antibody or an antigen-binding fragment thereof that specifically recognizes MHC class I molecules comprising the leukemia TAP defined in (i) or the combination defined in (ii) in their peptide binding groove.

68. The agent for use according to item 67, wherein the leukemia TAP is as defined in any one of items 1 to 31, the combination is as defined in item 32, the nucleic acid is as defined in item 33 or 34, the liposome is as defined in item 35, the composition is as defined in item 36, the vaccine is as defined in item 37, the cell is as defined in any one of items 41-44, 51 and 52, the cell population is as defined in item 53, and/or the antibody or antigen-binding fragment is as defined in any one of items 46-50.

69. The agent for use according to item 67 or 68, wherein said lymphoblastic leukemia is acute lymphoblastic leukemia (ALL).

70. The agent for use according to item 69, wherein the ALL is B-ALL.

71. The agent for use according to any one of items 67-70, which is for use in combination with at least one additional antitumor agent or therapy.

72. The agent for use according to item 71, wherein said at least one additional antitumor agent or therapy is a chemotherapeutic agent, immunotherapy, an immune checkpoint inhibitor, radiotherapy or surgery.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A shows the workflow for the analysis of native and TMT-labeled MHC I peptides. B-LCL cells were lysed and MHC I peptides purified by immunopurification. Half of the purified peptides were labeled with TMT, and both native and TMT-labeled peptides were analyzed by LC-MS/MS.

FIG. 1B shows the distribution of unique peptides and FIG. 1C shows their corresponding PEAKS scores.

FIG. 1D shows the number of identifications for unique and common peptides according to the charge state. Correlation of retention time (e) and intensity (f) for native and TMT-labeled MHC I peptides.

FIG. 1E shows correlation of retention time for native and TMT-labeled MHC I peptides.

FIG. 1F shows intensity for native and TMT-labeled MHC I peptides.

FIGS. 2A-C show the fragmentation patterns of native and TMT-labeled MHC I peptides. FIG. 2A shows the distribution of sequence ions according to fragment ion types. FIG. 2B shows the identification of MHC I peptides for different HLA allele groups. FIG. 2C shows the average number of a, b, and y-type fragment ions identified for each HLA allele group.

FIG. 5B shows the MiHA expression levels (#molecule/cell) obtained for all three LC-MS/MS approaches. Error bar indicates standard deviation observed on measurements.

FIG. 6A shows a comparison of the number of native and TMT-labeled MHC I peptides identified under different gradient elution conditions.

FIG. 6B depicts Venn diagrams showing the overlap of identified MHC I peptides for different gradient elution conditions.

DISCLOSURE OF INVENTION

Figures 2B, 2C:
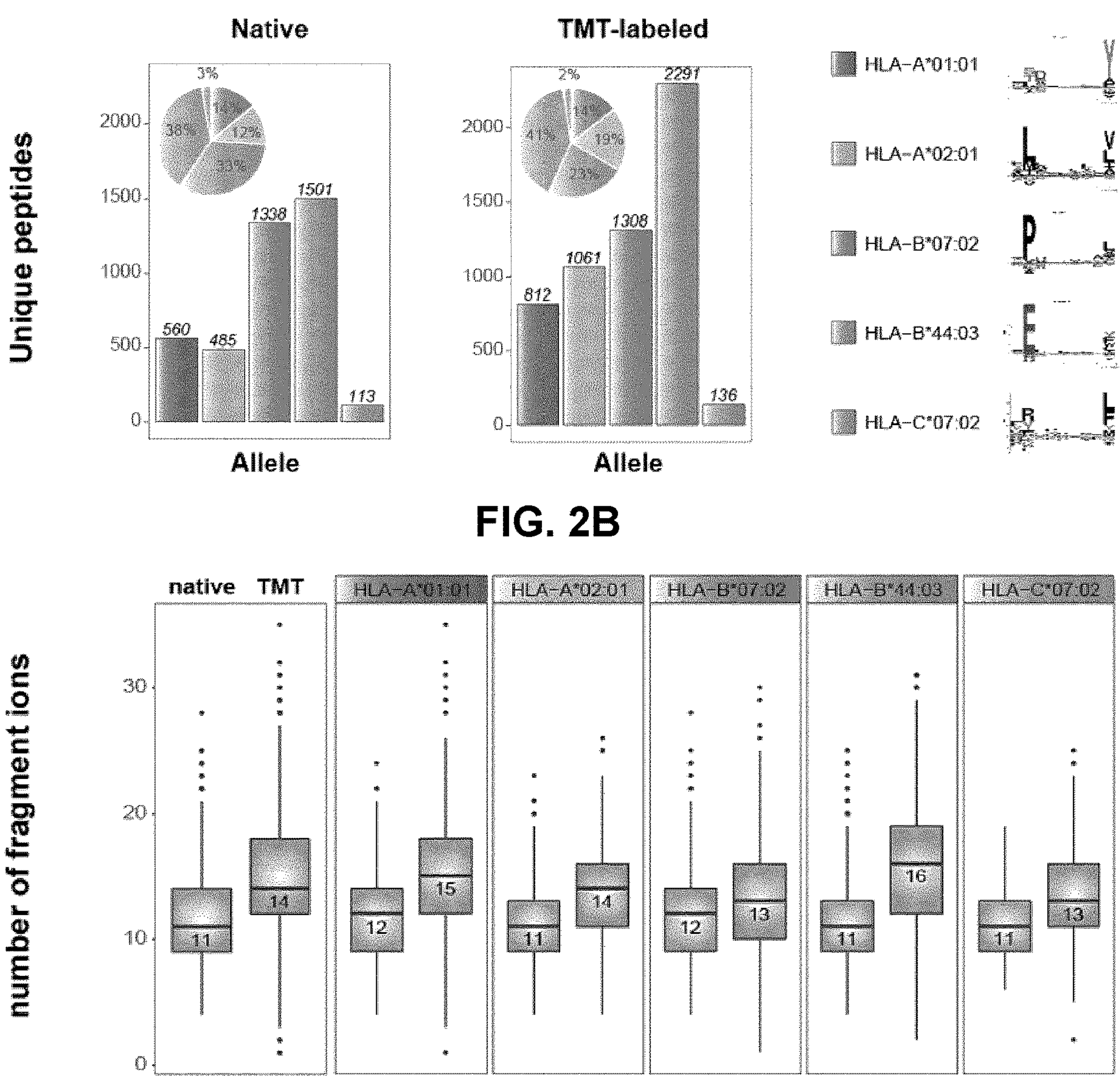

Terms and symbols of genetics, molecular biology, biochemistry and nucleic acid used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All terms are to be understood with their typical meanings established in the relevant art.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illustrate the invention and does not pose a limitation on the scope of the invention unless otherwise claimed.

No language in the specification should be construed as indicating any non-claimed element as essential to the practice of the invention.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

In the studies described herein, the present inventors have identified TSA candidates from an ALL specimen using a proteogenomic-based approach using isobaric peptide labeling with tandem mass tag (TMT). A large fraction of these TSAs derived from aberrantly expressed unmutated genomic sequences which are not expressed in normal tissues, such as non-exonic sequences (e.g., intronic and intergenic sequences). The novel ALL TSA candidates identified herein may be useful, e.g., for leukemia T-cell based immunotherapy.

Accordingly, in an aspect, the present disclosure relates to a leukemia tumor antigen peptide (or leukemia tumor-specific peptide) comprising, or consisting of, one of the following amino acid sequences:

| Sequence | SEQ ID NO: | Sequence | SEQ ID NO: | Sequence | SEQ ID NO: |
|---|---|---|---|---|---|
| NEQTTILY | 1 | LLGLPQPPK | 31 | GEFLVPLSL | 61 |
| ALFSNEVSL | 2 | LSSRLPLGK | 32 | GEVDGAQQAM | 62 |
| FIPDLFTEL | 3 | NLLFSRVFK | 33 | IEEVSQGLL | 63 |
| FLLDHILTI | 4 | STGVLTVLK | 34 | IESEDFGFWSL | 64 |
| FLLESRETL | 5 | SVFDRTNNR | 35 | LENSGFILI | 65 |
| FLLPTSLSL | 6 | SVVPHPLQK | 36 | REPLEILITL | 66 |
| FLLSDELLL | 7 | TTSSIYIRK | 37 | EETDAYKSL | 67 |
| GLATAVWLL | 8 | LYTFIKHEF | 38 | SELQLPVTF | 68 |
| GLLTASIFL | 9 | SYFDPSYSNF | 39 | QEIATSHNI | 69 |
| GTLCLLTFI | 10 | SYLASFLLY | 40 | AQFLLFIA | 70 |
| KLLQPLPIT | 11 | VYSPSPLNF | 41 | FEISSVTTA | 71 |
| LLQNLIVLL | 12 | VYTQVSAF | 42 | KEVGGLRSA | 72 |
| LLSLYLVSI | 13 | YSVLTVTF | 43 | TEFGPVIG | 73 |
| LMLLFVVLL | 14 | NLGLFLSY | 44 | ISLPALEVL | 74 |
| SLANETHTL | 15 | AVGGFRSSW | 45 | LPSPPLPPSL | 75 |
| VLLDFPALL | 16 | SQVQAVLLAW | 46 | LYLPSVVLI | 76 |
| VLLSKILYP | 17 | QTNSGSLAR | 47 | RPPAPLLPVL | 77 |

-continued

| Sequence | SEQ ID NO: | Sequence | SEQ ID NO: | Sequence | SEQ ID NO: |
|---|---|---|---|---|---|
| WLVEKLSGV | 18 | DVAGVGMPK | 48 | SLHYSVSL | 78 |
| YLFAHSIIL | 19 | DVMASLARV | 49 | SLPDHQGVL | 79 |
| YLGYAVAV | 20 | EVGAVFAVL | 50 | EAVSQGKDF | 80 |
| YLQEISLRL | 21 | VVADILLSV | 51 | YSSYLSIHY | 81 |
| SLLGIGLLA | 22 | SSLSGPVSSL | 52 | ASLGLSLAL | 82 |
| AAMESPIQSK | 23 | AFRVIVAL | 53 | LCHRTPPSL | 83 |
| ALFGFVGFPNK | 24 | EHYNKVVVM | 54 | LSISPFQAI | 84 |
| ALFVLTSIK | 25 | VQAQVLEAI | 55 | GWGGSPLYL | 85 |
| ATSLTIQEK | 26 | NNMAIIYSY | 56 | YFDPSYSNF | 86 |
| AVAVPLLPR | 27 | EPSHSINVY | 57 | ISLSSIVSV | 87 |
| GTISGGFFK | 28 | IPVGSGLGYVL | 58 | LSISSLVSV | 88 |
| GVANSLLK | 29 | DHDIGVYSV | 59 | | |
| GVSPVLFLK | 30 | HFEWQPPL | 60 | | |

In general, peptides such as tumor antigen peptides (TAPs) presented in the context of HLA class I vary in length from about 7 or 8 to about 15, or preferably 8 to 14 amino acid residues. In some embodiments of the methods of the disclosure, longer peptides comprising the TAP sequences defined herein are artificially loaded into cells such as antigen presenting cells (APCs), processed by the cells and the TAP is presented by MHC class I molecules at the surface of the APC. In this method, peptides/polypeptides longer than 15 amino acid residues can be loaded into APCs, are processed by proteases in the APC cytosol providing the corresponding TAP as defined herein for presentation. In some embodiments, the precursor peptide/polypeptide that is used to generate the TAP defined herein is for example 1000, 500, 400, 300, 200, 150, 100, 75, 50, 45, 40, 35, 30, 25, 20 or 15 amino acids or less. Thus, all the methods and processes using the TAPs described herein include the use of longer peptides or polypeptides (including the native protein), i.e. tumor antigen precursor peptides/polypeptides, to induce the presentation of the "final" 8-14 TAP following processing by the cell (APCs). In some embodiments, the herein-mentioned TAP is about 8 to 14, 8 to 13, or 8 to 12 amino acids long (e.g., 8, 9, 10, 11, 12 or 13 amino acids long), small enough for a direct fit in an HLA class I molecule. In an embodiment, the TAP comprises 20 amino acids or less, preferably 15 amino acids or less, more preferably 14 amino acids or less. In an embodiment, the TAP comprises at least 7 amino acids, preferably at least 8 amino acids or less, more preferably at least 9 amino acids.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of TAPs. Examples of naturally occurring amino acids are glycine, alanine, valine, leucine, isoleucine, serine, threonine, etc. Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diaminopropionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Hoarg), N-acetyl lysine, 2-amino butyric acid, 2-amino butyric acid, 2,4-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry. In an embodiment, the TAP comprises only naturally-occurring amino acids.

In embodiments, the TAPs described herein include peptides with altered sequences containing substitutions of functionally equivalent amino acid residues, relative to the herein-mentioned sequences. For example, one or more amino acid residues within the sequence can be substituted by another amino acid of a similar polarity (having similar physico-chemical properties) which acts as a functional equivalent, resulting in a silent alteration. Substitution for an amino acid within the sequence may be selected from other members of the class to which the amino acid belongs. For example, positively charged (basic) amino acids include arginine, lysine and histidine (as well as homoarginine and ornithine). Nonpolar (hydrophobic) amino acids include leucine, isoleucine, alanine, phenylalanine, valine, proline, tryptophan and methionine. Uncharged polar amino acids include serine, threonine, cysteine, tyrosine, asparagine and glutamine. Negatively charged (acidic) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. The herein-mentioned TAP may comprise all L-amino acids, all D-amino acids or a mixture of L- and D-amino acids. In an embodiment, the herein-mentioned TAP comprises all L-amino acids.

In an embodiment, in the sequences of the TAPs comprising or consisting of one of sequences of SEQ ID NOs: 1-88, the amino acid residues that do not substantially contribute to interactions with the T-cell receptor may be modified by replacement with other amino acid whose incorporation does not substantially affect T-cell reactivity and does not eliminate binding to the relevant MHC.

The TAP may also be N- and/or C-terminally capped or modified to prevent degradation, increase stability, affinity and/or uptake. Thus, in another aspect, the present disclosure provides a modified TAP of the formula $Z^1$—X—$Z^2$, wherein X is a TAP comprising, or consisting of, one of the amino acid sequences of SEQ ID NOs: 1-88.

In an embodiment, the amino terminal residue (i.e., the free amino group at the N-terminal end) of the TAP is modified (e.g., for protection against degradation), for example by covalent attachment of a moiety/chemical group ($Z^1$). $Z^1$ may be a straight chained or branched alkyl group of one to eight carbons, or an acyl group (R—CO—), wherein R is a hydrophobic moiety (e.g., acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac). In an embodiment, $Z^1$ is absent. The carboxy terminal residue (i.e., the free carboxy group at the C-terminal end of the TAP) of the TAP may be modified (e.g., for protection against degradation), for example by amidation (replacement of the OH group by a $NH_2$ group), thus in such a case $Z^2$ is a $NH_2$ group. In an embodiment, $Z^2$ may be an hydroxamate group, a nitrile group, an amide (primary, secondary or tertiary) group, an aliphatic amine of one to ten carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$. In an embodiment, $Z^2$ is absent. In an embodiment, the TAP comprises one of the amino acid sequences of SEQ ID NOs: 1-88. In an embodiment, the TAP consists of one of the amino acid sequences of SEQ ID NOs: 1-88, i.e. wherein $Z^1$ and $Z^2$ are absent.

In another aspect, the present disclosure provides a leukemia TAP (or tumor-specific peptide), preferably an ALL TAP, binding to an HLA-A*01:01 molecule, comprising or consisting of the sequence of SEQ ID NO: 1.

In another aspect, the present disclosure provides a leukemia TAP (or tumor-specific peptide), preferably an ALL TAP, binding to an HLA-A*02:01 molecule, comprising or consisting of the sequence of SEQ ID NO: 2-22. Because HLA alleles show promiscuity (certain HLA alleles present similar epitopes[43]), the above-identified TAP may further bind to HLA-A*02:05, HLA-A*02:06 and/or HLA-A*02:07 molecules.

In another aspect, the present disclosure provides a leukemia TAP (or tumor-specific peptide), preferably an ALL TAP, binding to an HLA-A*11:01 molecule, comprising or consisting of the sequence of SEQ ID NO: 23-37. Because HLA alleles show promiscuity (certain HLA alleles present similar epitopes), the above-identified TAP may further bind to HLA-A*03:01, HLA-A*31:01 and/or HLA-A*68:01 molecules.

In another aspect, the present disclosure provides a leukemia TAP (or tumor-specific peptide), preferably an ALL TAP, binding to an HLA-A*24:02 molecule, comprising or consisting of the sequence of SEQ ID NO: 38-43. Because HLA alleles show promiscuity (certain HLA alleles present similar epitopes), the above-identified TAP may further bind to HLA-A*23:01 molecules.

In another aspect, the present disclosure provides a leukemia TAP (or tumor-specific peptide), preferably an ALL TAP, binding to an HLA-A*29:02 molecule, comprising or consisting of the sequence of SEQ ID NO: 44. Because HLA alleles show promiscuity (certain HLA alleles present similar epitopes), the above-identified TAP may further bind to HLA-A*30:02 and/or HLA-B*15:02 molecules.

In another aspect, the present disclosure provides a leukemia TAP (or tumor-specific peptide), preferably an ALL TAP, binding to an HLA-A*32:01 molecule, comprising or consisting of the sequence of SEQ ID NO: 45 or 46. Because HLA alleles show promiscuity (certain HLA alleles present similar epitopes), the above-identified TAP may further bind to HLA-B*57:01 and/or HLA-B*58:01 molecules.

In another aspect, the present disclosure provides a leukemia TAP (or tumor-specific peptide), preferably an ALL TAP, binding to an HLA-A*66:01 molecule, comprising or consisting of the sequence of SEQ ID NO: 47. Because HLA alleles show promiscuity (certain HLA alleles present similar epitopes), the above-identified TAP may further bind to HLA-A*25:01 and/or HLA-A*26:01 molecules.

In another aspect, the present disclosure provides a leukemia TAP (or tumor-specific peptide), preferably an ALL TAP, binding to an HLA-A*68:01 molecule, comprising or consisting of the sequence of SEQ ID NO: 48. Because HLA alleles show promiscuity (certain HLA alleles present similar epitopes), the above-identified TAP may further bind to HLA-A*11:01, HLA-A*31:01, HLA-A*33:01 and/or HLA-A*33:03 molecules.

In another aspect, the present disclosure provides a leukemia TAP (or tumor-specific peptide), preferably an ALL TAP, binding to an HLA-A*68:02 molecule, comprising or consisting of the sequence of SEQ ID NO: 49-51.

In another aspect, the present disclosure provides a leukemia TAP (or tumor-specific peptide), preferably an ALL TAP, binding to an HLA-B*07:02 molecule, comprising or consisting of the sequence of SEQ ID NO: 52. Because HLA alleles show promiscuity (certain HLA alleles present similar epitopes), the above-identified TAP may further bind to HLA-B*35:02, HLA-B*35:03, HLA-B*55:01 and/or HLA-B*56:01 molecules.

In another aspect, the present disclosure provides a leukemia TAP (or tumor-specific peptide), preferably an ALL TAP, binding to an HLA-B*08:01 molecule, comprising or consisting of the sequence of SEQ ID NO: 53.

In another aspect, the present disclosure provides a leukemia TAP (or tumor-specific peptide), preferably an ALL TAP, binding to an HLA-B*14:02 molecule, comprising or consisting of the sequence of SEQ ID NO: 54. Because HLA alleles show promiscuity (certain HLA alleles present similar epitopes), the above-identified TAP may further bind to HLA-B*39:01 molecules.

In another aspect, the present disclosure provides a leukemia TAP (or tumor-specific peptide), preferably an ALL TAP, binding to an HLA-B*15:10 molecule, comprising or consisting of the sequence of SEQ ID NO: 55.

In another aspect, the present disclosure provides a leukemia TAP (or tumor-specific peptide), preferably an ALL TAP, binding to an HLA-B*18:01 molecule, comprising or consisting of the sequence of SEQ ID NO: 56. Because HLA alleles show promiscuity (certain HLA alleles present similar epitopes), the above-identified TAP may further bind to HLA-B*40:01, HLA-B*44:02, HLA-B*44:03 and/or HLA-B*45:01 molecules.

In another aspect, the present disclosure provides a leukemia TAP (or tumor-specific peptide), preferably an ALL TAP, binding to an HLA-B*35:01 molecule, comprising or consisting of the sequence of SEQ ID NO: 57 or 58. Because HLA alleles show promiscuity (certain HLA alleles present similar epitopes), the above-identified TAP may further bind to HLA-B*15:02, HLA-B*35:02, HLA-B*35:03 and/or HLA-B*53:01 molecules.

In another aspect, the present disclosure provides a leukemia TAP (or tumor-specific peptide), preferably an ALL TAP, binding to an HLA-B*39:01 molecule, comprising or consisting of the sequence of SEQ ID NO: 59 or 60. Because HLA alleles show promiscuity (certain HLA alleles present similar epitopes), the above-identified TAP may further bind to HLA-B*14:02 and/or HLA-B*38:01 molecules.

In another aspect, the present disclosure provides a leukemia TAP (or tumor-specific peptide), preferably an ALL TAP, binding to an HLA-B*40:01 molecule, comprising or consisting of the sequence of SEQ ID NO: 61-66. Because HLA alleles show promiscuity (certain HLA alleles present similar epitopes), the above-identified TAP may further bind to HLA-B*18:01, HLA-B*40:02, HLA-B*41:02, HLA-B*44:02, HLA-B*44:03 and/or HLA-B*45:01 molecules.

In another aspect, the present disclosure provides a leukemia TAP (or tumor-specific peptide), preferably an ALL TAP, binding to an HLA-B*44:02 molecule, comprising or consisting of the sequence of SEQ ID NO: 67 or 68. Because HLA alleles show promiscuity (certain HLA alleles present similar epitopes), the above-identified TAP may further bind to HLA-B*18:01, HLA-B*40:01, HLA-B*40:02, HLA-B*41:02, HLA-B*44:03 and/or HLA-B*45:01 molecules.

In another aspect, the present disclosure provides a leukemia TAP (or tumor-specific peptide), preferably an ALL TAP, binding to an HLA-B*49:01 molecule, comprising or consisting of the sequence of SEQ ID NO: 69.

In another aspect, the present disclosure provides a leukemia TAP (or tumor-specific peptide), preferably an ALL TAP, binding to an HLA-B*50:01 molecule, comprising or consisting of the sequence of SEQ ID NO: 70-73.

In another aspect, the present disclosure provides a leukemia TAP (or tumor-specific peptide), preferably an ALL TAP, binding to an HLA-C*01:02 molecule, comprising or consisting of the sequence of SEQ ID NO: 74-79.

In another aspect, the present disclosure provides a leukemia TAP (or tumor-specific peptide), preferably an ALL TAP, binding to an HLA-C*02:02 molecule, comprising or consisting of the sequence of SEQ ID NO: 80 or 81.

In another aspect, the present disclosure provides a leukemia TAP (or tumor-specific peptide), preferably an ALL TAP, binding to an HLA-C*03:04 molecule, comprising or consisting of the sequence of SEQ ID NO: 82-84. Because HLA alleles show promiscuity (certain HLA alleles present similar epitopes), the above-identified TAP may further bind to HLA-B*46:01, HLA-C*03:02, HLA-C*03:04, HLA-C*08:01, HLA-C*08:02, HLA-C*12:02, HLA-C*12:03, HLA-C*15:02 and/or HLA-C*16:01 molecules.

In another aspect, the present disclosure provides a leukemia TAP (or tumor-specific peptide), preferably an ALL TAP, binding to an HLA-C*04:01 molecule, comprising or consisting of the sequence of SEQ ID NO: 85 or 86. Because HLA alleles show promiscuity (certain HLA alleles present similar epitopes), the above-identified TAP may further bind to HLA-C*07:02 and/or HLA-C*14:02 molecules.

In another aspect, the present disclosure provides a leukemia TAP (or tumor-specific peptide), preferably an ALL TAP, binding to an HLA-C*15:02 molecule, comprising or consisting of the sequence of SEQ ID NO: 87 or 88. Because HLA alleles show promiscuity (certain HLA alleles present similar epitopes), the above-identified TAP may further bind to HLA-C*03:03, HLA-C*03:04, HLA-C*08:01, HLA-C*08:02, HLA-C*12:02 and/or HLA-C*12:03 molecules.

In an embodiment, the TAP is encoded by a sequence located a non-protein coding region of the genome. In an embodiment, the TAP is encoded by a sequence located in an untranslated transcribed region (UTR), i.e. a 3'-UTR or 5'-UTR region. In another embodiment, the TAP is encoded by a sequence located in an intron. In another embodiment, the TAP is encoded by a sequence located in an intergenic region. In another embodiment, the TAP is encoded by a sequence located in an exon and originates from a frameshift.

The TAPs of the disclosure may be produced by expression in a host cell comprising a nucleic acid encoding the TAPs (recombinant expression) or by chemical synthesis (e.g., solid-phase peptide synthesis). Peptides can be readily synthesized by manual and/or automated solid phase procedures well known in the art. Suitable syntheses can be performed for example by utilizing "T-boc" or "Fmoc" procedures. Techniques and procedures for solid phase synthesis are described in for example Solid Phase Peptide Synthesis: A Practical Approach, by E. Atherton and R. C. Sheppard, published by IRL, Oxford University Press, 1989. Alternatively, the MiHA peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the TAPs are described in Nakagawa et al., *J. Am. Chem. Soc.* 107: 7087-7092, 1985. In an embodiment, the TAP is chemically synthesized (synthetic peptide). Another embodiment of the present disclosure relates to a non-naturally occurring peptide wherein said peptide consists or consists essentially of an amino acid sequences defined herein and has been synthetically produced (e.g. synthesized) as a pharmaceutically acceptable salt. The salts of the TAPs according to the present disclosure differ substantially from the peptides in their state(s) in vivo, as the peptides as generated in vivo are no salts. The non-natural salt form of the peptide may modulate the solubility of the peptide, in particular in the context of pharmaceutical compositions comprising the peptides, e.g. the peptide vaccines as disclosed herein. Preferably, the salts are pharmaceutically acceptable salts of the peptides.

In an embodiment, the herein-mentioned TAP is substantially pure. A compound is "substantially pure" when it is separated from the components that naturally accompany it. Typically, a compound is substantially pure when it is at least 60%, more generally 75%, 80% or 85%, preferably over 90% and more preferably over 95%, by weight, of the total material in a sample. Thus, for example, a polypeptide that is chemically synthesized or produced by recombinant technology will generally be substantially free from its naturally associated components, e.g. components of its source macromolecule. A nucleic acid molecule is substantially pure when it is not immediately contiguous with (i.e., covalently linked to) the coding sequences with which it is normally contiguous in the naturally occurring genome of the organism from which the nucleic acid is derived. A substantially pure compound can be obtained, for example, by extraction from a natural source; by expression of a recombinant nucleic acid molecule encoding a peptide compound; or by chemical synthesis. Purity can be measured using any appropriate method such as column chromatography, gel electrophoresis, HPLC, etc. In an embodiment, the TAP is in solution. In another embodiment, the TAP is in solid form, e.g., lyophilized.

In another aspect, the disclosure further provides a nucleic acid (isolated) encoding the herein-mentioned TAPs or a tumor antigen precursor-peptide. In an embodiment, the nucleic acid comprises from about 21 nucleotides to about 45 nucleotides, from about 24 to about 45 nucleotides, for example 24, 27, 30, 33, 36, 39, 42 or 45 nucleotides. "Isolated", as used herein, refers to a peptide or nucleic molecule separated from other components that are present in the natural environment of the molecule or a naturally occurring source macromolecule (e.g., including other nucleic acids, proteins, lipids, sugars, etc.). "Synthetic", as used herein, refers to a peptide or nucleic molecule that is not isolated from its natural sources, e.g., which is produced through recombinant technology or using chemical synthesis. In an embodiment, the nucleic acid (DNA, RNA)

encoding the TAP of the disclosure comprises any one of the sequences defined in SEQ ID NOs: 93-180 or a corresponding RNA sequence. In an embodiment, the nucleic acid encoding the TAP is an mRNA molecule.

A nucleic acid of the disclosure may be used for recombinant expression of the TAP of the disclosure, and may be included in a vector or plasmid, such as a cloning vector or an expression vector, which may be transfected into a host cell. In an embodiment, the disclosure provides a cloning, expression or viral vector or plasmid comprising a nucleic acid sequence encoding the TAP of the disclosure. Alternatively, a nucleic acid encoding a TAP of the disclosure may be incorporated into the genome of the host cell. In either case, the host cell expresses the TAP or protein encoded by the nucleic acid. The term "host cell" as used herein refers not only to the particular subject cell, but to the progeny or potential progeny of such a cell. A host cell can be any prokaryotic (e.g., *E. coli*) or eukaryotic cell (e.g., insect cells, yeast or mammalian cells) capable of expressing the TAPs described herein. The vector or plasmid contains the necessary elements for the transcription and translation of the inserted coding sequence, and may contain other components such as resistance genes, cloning sites, etc. Methods that are well known to those skilled in the art may be used to construct expression vectors containing sequences encoding peptides or polypeptides and appropriate transcriptional and translational control/regulatory elements operably linked thereto. These methods include in vitro recombinant DNA techniques, synthetic techniques, and in vivo genetic recombination. Such techniques are described in Sambrook. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y. "Operably linked" refers to a juxtaposition of components, particularly nucleotide sequences, such that the normal function of the components can be performed. Thus, a coding sequence that is operably linked to regulatory sequences refers to a configuration of nucleotide sequences wherein the coding sequences can be expressed under the regulatory control, that is, transcriptional and/or translational control, of the regulatory sequences. "Regulatory/control region" or "regulatory/control sequence", as used herein, refers to the non-coding nucleotide sequences that are involved in the regulation of the expression of a coding nucleic acid. Thus, the term regulatory region includes promoter sequences, regulatory protein binding sites, upstream activator sequences, and the like. The vector (e.g., expression vector) may have the necessary 5' upstream and 3' downstream regulatory elements such as promoter sequences such as CMV, PGK and EFIa promoters, ribosome recognition and binding TATA box, and 3' UTR AAUAAA transcription termination sequence for the efficient gene transcription and translation in its respective host cell. Other suitable promoters include the constitutive promoter of simian vims 40 (SV40) early promoter, mouse mammary tumor virus (MMTV), HIV LTR promoter, MoMuLV promoter, avian leukemia virus promoter, EBV immediate early promoter, and Rous sarcoma vims promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing the TAP. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontrch), pCIneo vectors (Promega) for expression in mammalian cells; pLenti4A/5-DEST™, pLenti6/V5-DEST™, and pLenti6.2N5-GW/lacZ (Invitrogen) for lentivirus-mediated gene transfer and expression in mammalian cells. The coding sequences of the TAPs disclosed herein can be ligated into such expression vectors for the expression of the TAP in mammalian cells.

In certain embodiments, the nucleic acids encoding the TAP of the present disclosure are provided in a viral vector. A viral vector can be those derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for the various proteins described herein in place of nonessential viral genes. The vector and/or particle can be utilized for the purpose of transferring DNA, RNA or other nucleic acids into cells either in vitro or in vivo. Numerous forms of viral vectors are known in the art.

In embodiment, the nucleic acid (DNA, RNA) encoding the TAP of the disclosure is comprised within a liposome or any other suitable vehicle.

In another aspect, the present disclosure provides an MHC class I molecule comprising (i.e. presenting or bound to) one or more of the TAP of SEQ ID NOs: 1-88. In an embodiment, the MHC class I molecule is an HLA-A1 molecule, in a further embodiment an HLA-A*01:01 molecule. In an embodiment, the MHC class I molecule is an HLA-A2 molecule, in a further embodiment an HLA-A*02:01 molecule. In another embodiment, the MHC class I molecule is an HLA-A11 molecule, in a further embodiment an HLA-A*11:01 molecule. In an embodiment, the MHC class I molecule is an HLA-A24 molecule, in a further embodiment an HLA-A*24:02 molecule. In an embodiment, the MHC class I molecule is an HLA-A29 molecule, in a further embodiment an HLA-A*29:02 molecule. In an embodiment, the MHC class I molecule is an HLA-A32 molecule, in a further embodiment an HLA-A*32:01 molecule. In an embodiment, the MHC class I molecule is an HLA-A66 molecule, in a further embodiment an HLA-A*66:01 molecule. In an embodiment, the MHC class I molecule is an HLA-A68 molecule, in a further embodiment an HLA-A*68:01 or HLA-A*68:02 molecule. In another embodiment, the MHC class I molecule is an HLA-B07 molecule, in a further embodiment an HLA-B*07:02 molecule. In another embodiment, the MHC class I molecule is an HLA-B08 molecule, in a further embodiment an HLA-B*08:01 molecule. In another embodiment, the MHC class I molecule is an HLA-B14 molecule, in a further embodiment an HLA-B*14:02 molecule. In another embodiment, the MHC class I molecule is an HLA-B15 molecule, in a further embodiment an HLA-B*15:10 molecule. In another embodiment, the MHC class I molecule is an HLA-B18 molecule, in a further embodiment an HLA-B*18:01 molecule. In another embodiment, the MHC class I molecule is an HLA-B35 molecule, in a further embodiment an HLA-B*35:01 molecule. In another embodiment, the MHC class I molecule is an HLA-B39 molecule, in a further embodiment an HLA-B*39:01 molecule. In another embodiment, the MHC class I molecule is an HLA-B40 molecule, in a further embodiment an HLA-B*40:01 molecule. In another embodiment, the MHC class I molecule is an HLA-B44 molecule, in a further embodiment an HLA-B*44:02 molecule. In another embodiment, the MHC class I molecule is an HLA-B49 molecule, in a further embodiment an HLA-B*49:01 molecule. In another embodiment, the MHC class I molecule is an HLA-B50 molecule, in a further embodiment an HLA-B*50:01 molecule. In another embodiment, the MHC class I molecule is an HLA-001 molecule, in a further embodiment an HLA-C*01:02 molecule. In another embodiment, the MHC class I molecule is an HLA-C02 molecule, in a further embodiment an HLA-C*02:02 molecule. In another embodiment, the MHC class I molecule is an HLA-C03 molecule, in a further embodiment an HLA-C*03:04 molecule. In another embodiment, the MHC class I molecule is an HLA-004 molecule, in a further embodiment an HLA-C*04:01 molecule. In another embodiment, the MHC class I molecule is an HLA-C15 molecule, in a further embodiment an HLA-C*15:02 molecule.

In an embodiment, the TAP (e.g., SEQ ID NOs: 1-88) is non-covalently bound to the MHC class I molecule (i.e., the TAP is loaded into, or non-covalently bound to the peptide binding groove/pocket of the MHC class I molecule). In another embodiment, the TAP is covalently attached/bound to the MHC class I molecule (alpha chain). In such a construct, the TAP and the MHC class I molecule (alpha chain) are produced as a synthetic fusion protein, typically with a short (e.g., 5 to 20 residues, preferably about 8-12, e.g., 10) flexible linker or spacer (e.g., a polyglycine linker). In another aspect, the disclosure provides a nucleic acid encoding a fusion protein comprising a TAP defined herein fused to a MHC class I molecule (alpha chain). In an embodiment, the MHC class I molecule (alpha chain)—peptide complex is multimerized. Accordingly, in another aspect, the present disclosure provides a multimer of MHC class I molecule loaded (covalently or not) with the herein-mentioned TAP. Such multimers may be attached to a tag, for example a fluorescent tag, which allows the detection of the multimers. A great number of strategies have been developed for the production of MHC multimers, including MHC dimers, tetramers, pentamers, octamers, etc. (reviewed in Bakker and Schumacher, *Current Opinion in Immunology* 2005, 17:428-433). MHC multimers are useful, for example, for the detection and purification of antigen-specific T cells. Thus, in another aspect, the present disclosure provides a method for detecting or purifying (isolating, enriching) $CD8^+$ T lymphocytes specific for a TAP defined herein, the method comprising contacting a cell population with a multimer of MHC class I molecule loaded (covalently or not) with the TAP; and detecting or isolating the $CD8^+$ T lymphocytes bound by the MHC class I multimers. $CD8^+$ T lymphocytes bound by the MHC class I multimers may be isolated using known methods, for example fluorescence activated cell sorting (FACS) or magnetic activated cell sorting (MACS).

In yet another aspect, the present disclosure provides a cell (e.g., a host cell), in an embodiment an isolated cell, comprising the herein-mentioned nucleic acid, vector or plasmid of the disclosure, i.e. a nucleic acid or vector encoding one or more TAPs. In another aspect, the present disclosure provides a cell expressing at its surface an MHC class I molecule (e.g., an MHC class I molecule of one of the alleles disclosed above) bound to or presenting a TAP according to the disclosure. In one embodiment, the host cell is a eukaryotic cell, such as a mammalian cell, preferably a human cell. a cell line or an immortalized cell. In another embodiment, the cell is an antigen-presenting cell (APC). In one embodiment, the host cell is a primary cell, a cell line or an immortalized cell. In another embodiment, the cell is an antigen-presenting cell (APC). Nucleic acids and vectors can be introduced into cells via conventional transformation or transfection techniques. The terms “transformation” and “transfection” refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing nucleic acids into mammalian cells in vivo are also known, and may be used to deliver the vector or plasmid of the disclosure to a subject for gene therapy.

Cells such as APCs can be loaded with one or more TAPs using a variety of methods known in the art. As used herein “loading a cell” with a TAP means that RNA or DNA encoding the TAP, or the TAP, is transfected into the cells or alternatively that the APC is transformed with a nucleic acid encoding the TAP. The cell can also be loaded by contacting the cell with exogenous TAPs that can bind directly to MHC class I molecule present at the cell surface (e.g., peptide-pulsed cells). The TAPs may also be fused to a domain or motif that facilitates its presentation by MHC class I molecules, for example to an endoplasmic reticulum (ER) retrieval signal, a C-terminal Lys-Asp-Glu-Leu sequence (see Wang et al., *Eur J Immunol.* 2004 December; 34(12): 3582-94).

In another aspect, the present disclosure provides a composition or peptide combination/pool comprising any one of, or any combination of, the TAPs defined herein (or a nucleic acid encoding said peptide(s)). In an embodiment, the composition comprises any combination of the TAPs defined herein (any combination of 2, 3, 4, 5, 6, 7, 8, 9, 10 or more TAPs), or a combination of nucleic acids encoding said TAPs). Compositions comprising any combination/sub-combination of the TAPs defined herein are encompassed by the present disclosure. In another embodiment, the combination or pool may comprise one or more known tumor antigens.

Thus, in another aspect, the present disclosure provides a composition comprising any one of, or any combination of, the TAPs defined herein (e.g., SEQ ID NOs: 1-88) and a cell expressing a MHC class I molecule (e.g., a MHC class I molecule of one of the alleles disclosed above). APC for use in the present disclosure are not limited to a particular type of cell and include professional APCs such as dendritic cells (DCs), Langerhans cells, macrophages and B cells, which are known to present proteinaceous antigens on their cell surface so as to be recognized by $CD8^+$ T lymphocytes. For example, an APC can be obtained by inducing DCs from peripheral blood monocytes and then contacting (stimulating) the TAPs, either in vitro, ex vivo or in vivo. APC can also be activated to present a TAP in vivo where one or more of the TAPs of the disclosure are administered to a subject and APCs that present a TAP are induced in the body of the subject. The phrase “inducing an APC” or “stimulating an APC" includes contacting or loading a cell with one or more TAPs, or nucleic acids encoding the TAPs such that the TAPs are presented at its surface by MHC class I molecules. As noted herein, according to the present disclosure, the TAPs may be loaded indirectly for example using longer peptides/polypeptides comprising the sequence of the TAPs (including the native protein), which is then processed (e.g., by proteases) inside the APCs to generate the TAP/MHC class I complexes at the surface of the cells. After loading APCs with TAPs and allowing the APCs to present the TAPs, the APCs can be administered to a subject as a vaccine. For example, the ex vivo administration can include the steps of: (a) collecting APCs from a first subject, (b) contacting/loading the APCs of step (a) with a TAP to form MHC class I/TAP complexes at the surface of the APCs; and (c) administering the peptide-loaded APCs to a second subject in need for treatment.

The first subject and the second subject may be the same subject (e.g., autologous vaccine), or may be different subjects (e.g., allogeneic vaccine). Alternatively, according to the present disclosure, use of a TAP described herein (or a combination thereof) for manufacturing a composition (e.g., a pharmaceutical composition) for inducing antigen-presenting cells is provided. In addition, the present disclosure provides a method or process for manufacturing a pharmaceutical composition for inducing antigen-presenting cells, wherein the method or the process includes the step of admixing or formulating the TAP, or a combination thereof, with a pharmaceutically acceptable carrier. Cells such as APCs expressing a MHC class I molecule (e.g., any of the above-noted HLA molecules) loaded with any one of, or any combination of, the TAPs defined herein, may be used for stimulating/amplifying $CD8^+$ T lymphocytes, for example autologous $CD8^+$ T lymphocytes. Accordingly, in another aspect, the present disclosure provides a composition comprising any one of, or any combination of, the TAPs defined herein (or a nucleic acid or vector encoding same); a cell expressing an MHC class I molecule and a T lymphocyte, more specifically a $CD8^+$ T lymphocyte (e.g., a population of cells comprising $CD8^+$ T lymphocytes).

In an embodiment, the composition further comprises a buffer, an excipient, a carrier, a diluent and/or a medium (e.g., a culture medium). In a further embodiment, the buffer, excipient, carrier, diluent and/or medium is/are pharmaceutically acceptable buffer(s), excipient(s), carrier(s), diluent(s) and/or medium (media). As used herein "pharmaceutically acceptable buffer, excipient, carrier, diluent and/or medium" includes any and all solvents, buffers, binders, lubricants, fillers, thickening agents, disintegrants, plasticizers, coatings, barrier layer formulations, lubricants, stabilizing agent, release-delaying agents, dispersion media, coatings, antibacterial and antifungal agents, isotonic agents, and the like that are physiologically compatible, do not interfere with effectiveness of the biological activity of the active ingredient(s) and that are not toxic to the subject. The use of such media and agents for pharmaceutically active substances is well known in the art (Rowe et al., Handbook of pharmaceutical excipients, 2003, $4^{th}$ edition, Pharmaceutical Press, London UK). Except insofar as any conventional media or agent is incompatible with the active compound (peptides, cells), use thereof in the compositions of the disclosure is contemplated. In an embodiment, the buffer, excipient, carrier and/or medium is a non-naturally occurring buffer, excipient, carrier and/or medium. In an embodiment, one or more of the TAPs defined herein, or the nucleic acids (e.g., mRNAs) encoding said one or more TAPs, are comprised within or complexed to a liposome, e.g., a cationic liposome (see, e.g., Vitor M T et al., *Recent Pat Drug Deliv Formul.* 2013 August; 7(2):99-110) or suitable other carriers.

In another aspect, the present disclosure provides a composition comprising one of more of the any one of, or any combination of, the TAPs defined herein (e.g., SEQ ID NOs: 1-88) (or a nucleic acid encoding said peptide(s)), and a buffer, an excipient, a carrier, a diluent and/or a medium. For compositions comprising cells (e.g., APCs, T lymphocytes), the composition comprises a suitable medium that allows the maintenance of viable cells. Representative examples of such media include saline solution, Earl's Balanced Salt Solution (Life Technologies®) or PlasmaLyte® (Baxter Internationale). In an embodiment, the composition (e.g., pharmaceutical composition) is an "immunogenic composition", "vaccine composition" or "vaccine". The term "Immunogenic composition", "vaccine composition" or "vaccine" as used herein refers to a composition or formulation comprising one or more TAPs or vaccine vector and which is capable of inducing an immune response against the one or more TAPs present therein when administered to a subject. Vaccination methods for inducing an immune response in a mammal comprise use of a vaccine or vaccine vector to be administered by any conventional route known in the vaccine field, e.g., via a mucosal (e.g., ocular, intranasal, pulmonary, oral, gastric, intestinal, rectal, vaginal, or urinary tract) surface, via a parenteral (e.g., subcutaneous, intradermal, intramuscular, intravenous, or intraperitoneal) route, or topical administration (e.g., via a transdermal delivery system such as a patch). In an embodiment, the TAP (or a combination thereof) is conjugated to a carrier protein (conjugate vaccine) to increase the immunogenicity of the TAP(s). The present disclosure thus provides a composition (conjugate) comprising a TAP (or a combination thereof), or a nucleic acid encoding the TAP or combination thereof, and a carrier protein. For example, the TAP(s) or nucleic acid(s) may be conjugated or complexed to a Toll-like receptor (TLR) ligand (see, e.g., Zom et al., *Adv Immunol.* 2012, 114: 177-201) or polymers/dendrimers (see, e.g., Liu et al., *Biomacromolecules.* 2013 Aug. 12; 14(8):2798-806). In an embodiment, the immunogenic composition or vaccine further comprises an adjuvant. "Adjuvant" refers to a substance which, when added to an immunogenic agent such as an antigen (TAPs, nucleic acids and/or cells according to the present disclosure), nonspecifically enhances or potentiates an immune response to the agent in the host upon exposure to the mixture. Examples of adjuvants currently used in the field of vaccines include (1) mineral salts (aluminum salts such as aluminum phosphate and aluminum hydroxide, calcium phosphate gels), squalene, (2) oil-based adjuvants such as oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), (3) particulate adjuvants, e.g., virosomes (unilamellar liposomal vehicles incorporating influenza haemagglutinin), AS04 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles, and the like.

In an embodiment, the TAP(s) (e.g., SEQ ID NOs: 1-88) or composition comprising same is/are in lyophilized form. In another embodiment, the TAP(s) or composition comprising same is/are in a liquid composition. In a further embodiment, the TAP(s) is/are at a concentration of about 0.01 μg/mL to about 100 μg/mL in the composition. In further embodiments, the TAP(s) is/are at a concentration of about 0.2 μg/mL to about 50 μg/mL, about 0.5 μg/mL to about 10, 20, 30, 40 or 50 μg/mL, about 1 μg/mL to about 10 μg/mL, or about 2 μg/mL, in the composition.

As noted herein, cells such as APCs that express an MHC class I molecule loaded with or bound to any one of, or any combination of, the TAPs defined herein, may be used for stimulating/amplifying $CD8^+$ T lymphocytes in vivo or ex vivo. Accordingly, in another aspect, the present disclosure provides T cell receptor (TCR) molecules capable of interacting with or binding the herein-mentioned MHC class I molecule/TAP complex, and nucleic acid molecules encoding such TCR molecules, and vectors comprising such nucleic acid molecules. A TCR according to the present disclosure is capable of specifically interacting with or binding a TAP loaded on, or presented by, an MHC class I molecule, preferably at the surface of a living cell in vitro or in vivo.

The term TCR as used herein refers to an immunoglobulin superfamily member having a variable binding domain, a constant domain, a transmembrane region, and a short cytoplasmic tail; see, e.g., Janeway et al, Immunobiology: The Immune System in Health and Disease, 3rd Ed., Current Biology Publications, p. 4:33, 1997) capable of specifically binding to an antigen peptide bound to a MHC receptor. A TCR can be found on the surface of a cell and generally is comprised of a heterodimer having α and β chains (also known as TCRα and TCRβ, respectively). Like immunoglobulins, the extracellular portion of TCR chains (e.g., α-chain, β-chain) contain two immunoglobulin regions, a variable region (e.g., TCR variable α region or Vα and TCR variable β region or Vβ; typically amino acids 1 to 116 based on Rabat numbering at the N-terminus), and one constant region (e.g., TCR constant domain α or Cα and typically amino acids 117 to 259 based on Rabat, TCR constant domain β or Cβ, typically amino acids 117 to 295 based on Rabat) adjacent to the cell membrane. Also, like immunoglobulins, the variable domains contain complementary determining regions (CDRs. 3 in each chain) separated by framework regions (FRs). In certain embodiments, a TCR is found on the surface of T cells (or T lymphocytes) and associates with the CD3 complex.

A TCR and in particular nucleic acids encoding a TCR of the disclosure may for instance be applied to genetically transform/modify T lymphocytes (e.g., $CD8^+$ T lymphocytes) or other types of lymphocytes generating new T lymphocyte clones that specifically recognize an MHC class I/TAP complex. In a particular embodiment, T lymphocytes (e.g., $CD8^+$ T lymphocytes) obtained from a patient are transformed to express one or more TCRs that recognize a TAP and the transformed cells are administered to the patient (autologous cell transfusion). In a particular embodiment, T lymphocytes (e.g., $CD8^+$ T lymphocytes) obtained from a donor are transformed to express one or more TCRs that recognize a TAP and the transformed cells are administered to a recipient (allogenic cell transfusion). In another embodiment, the disclosure provides a T lymphocyte e.g., a $CD8^+$ T lymphocyte transformed/transfected by a vector or plasmid encoding a TAP-specific TCR. In a further embodiment the disclosure provides a method of treating a patient with autologous or allogenic cells transformed with a TAP-specific TCR. In certain embodiments, TCRs are expressed in primary T cells (e.g., cytotoxic T cells) by replacing an endogenous locus, e.g., an endogenous TRAC and/or TRBC locus, using, e.g., CRISPR, TALEN, zinc finger, or other targeted disruption systems.

In another embodiment, the present disclosure provides a nucleic acid encoding the above-noted TCR. In a further embodiment, the nucleic acid is present in a vector, such as the vectors described above.

In yet a further embodiment the use of a tumor antigen-specific TCR in the manufacture of autologous or allogenic cells for the treating of cancer (e.g., lymphoblastic leukemia, such as ALL) is provided.

In some embodiments, patients treated with the compositions (e.g., pharmaceutical compositions) of the disclosure are treated prior to or following treatment with allogenic stem cell transplant (ASCL), allogenic lymphocyte infusion or autologous lymphocyte infusion. Compositions of the disclosure include: allogenic T lymphocytes (e.g., $CD8^+$ T lymphocyte) activated ex vivo against a TAP; allogenic or autologous APC vaccines loaded with a TAP; TAP vaccines and allogenic or autologous T lymphocytes (e.g., $CD8^+$ T lymphocyte) or lymphocytes transformed with a tumor antigen-specific TCR. The method to provide T lymphocyte clones capable of recognizing a TAP according to the disclosure may be generated for and can be specifically targeted to tumor cells expressing the TAP in a subject (e.g., graft recipient), for example an ASCT and/or donor lymphocyte infusion (DLI) recipient. Hence the disclosure provides a $CD8^+$ T lymphocyte encoding and expressing a T cell receptor capable of specifically recognizing or binding a TAP/MHC class I molecule complex. Said T lymphocyte (e.g., $CD8^+$ T lymphocyte) may be a recombinant (engineered) or a naturally selected T lymphocyte. This specification thus provides at least two methods for producing $CD8^+$ T lymphocytes of the disclosure, comprising the step of bringing undifferentiated lymphocytes into contact with a TAP/MHC class I molecule complex (typically expressed at the surface of cells, such as APCs) under conditions conducive of triggering T cell activation and expansion, which may be done in vitro or in vivo (i.e. in a patient administered with a APC vaccine wherein the APC is loaded with a TAP or in a patient treated with a TAP vaccine). Using a combination or pool of TAPs bound to MHC class I molecules, it is possible to generate a population $CD8^+$ T lymphocytes capable of recognizing a plurality of TAPs. Alternatively, tumor antigen-specific or targeted T lymphocytes may be produced/generated in vitro or ex vivo by cloning one or more nucleic acids (genes) encoding a TCR (more specifically the alpha and beta chains) that specifically binds to a MHC class I molecule/TAP complex (i.e. engineered or recombinant $CD8^+$ T lymphocytes). Nucleic acids encoding a TAP-specific TCR of the disclosure, may be obtained using methods known in the art from a T lymphocyte activated against a TAP ex vivo (e.g., with an APC loaded with a TAP); or from an individual exhibiting an immune response against peptide/MHC molecule complex. TAP-specific TCRs of the disclosure may be recombinantly expressed in a host cell and/or a host lymphocyte obtained from a graft recipient or graft donor, and optionally differentiated in vitro to provide cytotoxic T lymphocytes (CTLs). The nucleic acid(s) (transgene(s)) encoding the TCR alpha and beta chains may be introduced into a T cells (e.g., from a subject to be treated or another individual) using any suitable methods such as transfection (e.g., electroporation) or transduction (e.g., using viral vector). The engineered $CD8^+$ T lymphocytes expressing a TCR specific for a TAP may be expanded in vitro using well known culturing methods.

The present disclosure provides methods for making the immune effector cells which express the TCRs as described herein. In one embodiment, the method comprises transfecting or transducing immune effector cells, e.g., immune effector cells isolated from a subject, such as a subject having a leukemia (e.g., ALL), such that the immune effector cells express one or more TCR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a TCR. In this regard, the immune effector cells may be cultured before or after being genetically modified (i.e., transduced or transfected to express a TCR as described herein).

Prior to in vitro manipulation or genetic modification of the immune effector cells described herein, the source of cells may be obtained from a subject. In particular, the immune effector cells for use with the TCRs as described herein comprise T cells. T cells can be obtained from a number of sources, including peripheral blood mononuclear cells (PBMCs), bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL™ separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium and may lack magnesium or may lack many if not all divalent cations. As would be appreciated by those of ordinary skill in the art, a washing step may be accomplished by methods known to those in the art, such as by using a semi-automated flow-through centrifuge. After washing, the cells may be resuspended in a variety of biocompatible buffers or other saline solution with or without buffer. In certain embodiments, the undesirable components of the apheresis sample may be removed in the cell directly resuspended culture media. In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD8+ cells by negative selection, a monoclonal antibody cocktail typically includes antibodies to CD14, CD20, CD11 b, CD16, HLA-DR, and CD4. Flow cytometry and cell sorting may also be used to isolate cell populations of interest for use in the present disclosure. PBMC may be used directly for genetic modification with the TCRs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion.

The present disclosure provides isolated immune cells such as $CD8^+$ T lymphocytes that are specifically induced, activated and/or amplified (expanded) by a TAP (i.e., a TAP bound to MHC class I molecules expressed at the surface of cell), or a combination of TAPs. The present disclosure also provides a composition comprising $CD8^+$ T lymphocytes capable of recognizing a TAP, or a combination thereof, according to the disclosure (i.e., one or more TAPs bound to MHC class I molecules) and said TAP(s). In another aspect, the present disclosure provides a cell population or cell culture (e.g., a $CD8^+$ T lymphocyte population) enriched in $CD8^+$ T lymphocytes that specifically recognize one or more MHC class I molecule/TAP complex(es) as described herein. Such enriched population may be obtained by performing an ex vivo expansion of specific T lymphocytes using cells such as APCs that express MHC class I molecules loaded with (e.g. presenting) one or more of the TAPs disclosed herein. "Enriched" as used herein means that the proportion of tumor antigen-specific $CD8^+$ T lymphocytes in the population is significantly higher relative to a native population of cells, i.e. which has not been subjected to a step of ex vivo-expansion of specific T lymphocytes. In a further embodiment, the proportion of TAP-specific $CD8^+$ T lymphocytes in the cell population is at least about 0.5%, for example at least about 1%, 1.5%, 2% or 3%. In some embodiments, the proportion of TAP-specific $CD8^+$ T lymphocytes in the cell population is about 0.5 to about 10%, about 0.5 to about 8%, about 0.5 to about 5%, about 0.5 to about 4%, about 0.5 to about 3%, about 1% to about 5%, about 1% to about 4%, about 1% to about 3%, about 2% to about 5%, about 2% to about 4%, about 2% to about 3%, about 3% to about 5% or about 3% to about 4%. Such cell population or culture (e.g., a $CD8^+$ T lymphocyte population) enriched in $CD8^+$ T lymphocytes that specifically recognizes one or more MHC class I molecule/peptide (TAP) complex(es) of interest may be used in tumor antigen-based cancer immunotherapy, as detailed below. In some embodiments, the population of TAP-specific $CD8^+$ T lymphocytes is further enriched, for example using affinity-based systems such as multimers of MHC class I molecule loaded (covalently or not) with the TAP(s) defined herein. Thus, the present disclosure provides a purified or isolated population of TAP-specific $CD8^+$ T lymphocytes, e.g., in which the proportion of TAP-specific $CD8^+$ T lymphocytes is at least about 50%, 60%, 70%, 80%, 85%, 90%, 95%, 96%, 97%, 98%, 99% or 100%.

In another aspect, the present disclosure provides an antibody or an antigen-binding fragment thereof that specifically binds to a complex comprising a TAP as described herein bound to an HLA molecule, such as the HLA molecules defined herein. Such antibodies are commonly referred to as TCR-like antibodies. The term "antibody or antigen-binding fragment thereof" as used herein refers to any type of antibody/antibody fragment including monoclonal antibodies (including full-length monoclonal antibodies), polyclonal antibodies, multispecific antibodies, humanized antibodies, CDR-grafted antibodies, chimeric antibodies and antibody fragments so long as they exhibit the desired antigenic specificity/binding activity. Antibody fragments comprise a portion of a full-length antibody, generally an antigen binding or variable region thereof. Examples of antibody fragments include Fab, Fab', $F(ab')_2$, and Fv fragments, diabodies, linear antibodies, single-chain antibody molecules (e.g., single-chain Fv, scFv), single domain antibodies (e.g., from camelids), shark NAR single domain antibodies, and multispecific antibodies formed from antibody fragments, single-chain diabodies (scDbs), bispecific T cell engagers (BiTEs), dual affinity retargeting molecules (DARTs), bivalent scFv-Fcs, and trivalent scFv-Fcs. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies. In an embodiment, the antibody or antigen-binding fragment thereof is a single-chain antibody, preferably a single-chain Fv (scFv). In an embodiment, the antibody or antigen-binding fragment thereof comprises at least one constant domain, e.g., a constant domain of a light and/or heavy chain, or a fragment thereof. In a further embodiment, the antibody or antigen-binding fragment thereof comprises a Fragment crystallizable (Fc) fragment of the constant heavy chain of an antibody. In an embodiment, the antibody or antigen-binding fragment is a scFv comprising a Fc fragment (scFV-Fc). In an embodiment, the scFv component is connected to the Fc fragment by a linker, for example a hinge. The presence of an Fc region is useful to induce a Complement-dependent cytotoxicity (CDC) or antibody-dependent cellular cytotoxicity (ADCC) response against a tumor cell.

In an embodiment, the antibody or antigen-binding fragment thereof is a multispecific antibody or an antigen-binding fragment thereof, such as a bispecific antibody or an antigen-binding fragment thereof, wherein at least one of the antigen-binding domains of the multispecific antibody or antibody fragment recognize(s) a complex comprising a TAP as described herein bound to an HLA molecule. In an embodiment, at least one of the antigen-binding domains of the multispecific antibody or antibody fragment recognize(s) an immune cell effector molecule. The term "immune cell effector molecule" refers to a molecule (e.g., protein) expressed by an immune cell and whose engagement by the multispecific antibody or antibody fragment leads to activation of the immune cells. Examples of immune cell effector molecules include the CD3 signaling complex in T cells such as CD8 T cells and the various activating receptors on NK cells (NKG2D, KIR2DS, NKp44, etc.). In a further embodiment, at least one of the antigen-binding domains of the multispecific antibody or antibody fragment recognize(s) and engage(s) the CD3 signaling complex in T cells (e.g., anti-CD3). In a further embodiment, the multispecific antibody or antibody fragment is a single-chain diabody (scDb). In a further embodiment, the scDb comprises a first antibody fragment (e.g., scFv) that binds to a complex comprising a TAP as described herein bound to an HLA molecule and a second antibody fragment (e.g., scFv) that binds to and engages an immune cell effector molecule, such as the CD3 signaling complex in T cells (e.g., anti-CD3 scFv). Such constructs may be used for example to induce the cytotoxic T cell-mediated killing of tumor cells expressing the tumor antigen/MHC complex recognized by the multispecific antibody or antibody fragment[44-46]. Antibodies or antigen-binding fragments thereof may also be used as a chimeric antigen receptor (CAR) to produce CAR T cells, CAR NK cells, etc. CAR combines a ligand-binding domain (e.g. antibody or antibody fragment) that provides specificity for a desired antigen (e.g., MHC/TAP complex) with an activating intracellular domain (or signal transducing domain) portion, such as a T cell or NK cell activating domain, providing a primary activation signal. Antigen-binding fragments of antibodies, and more particularly scFv, capable of binding to molecules expressed by tumor cells are commonly used as ligand-binding domains in CAR. Thus, in another aspect, the present disclosure provides a host cell, preferably an immune cell such as a T cell or NK cell, expressing the antibody or antibody fragment (e.g., scFv) described herein.

The present disclosure further relates to a pharmaceutical composition or vaccine comprising the above-noted immune cell ($CD8^+$ T lymphocytes, CART cell) or population of TAP-specific $CD8^+$ T lymphocytes. Such pharmaceutical composition or vaccine may comprise one or more pharmaceutically acceptable excipients and/or adjuvants, as described above.

The present disclosure further relates to the use of any TAP (e.g., SEQ ID NOs: 1-88, 92), nucleic acid, expression vector, T cell receptor, antibody/antibody fragment, cell (e.g., T lymphocyte, APC, CAR T cell), and/or composition according to the present disclosure, or any combination thereof, as a medicament or in the manufacture of a medicament. In an embodiment, the medicament is for the treatment of cancer, e.g., cancer vaccine. The present disclosure relates to any TAP, nucleic acid, expression vector, T cell receptor, antibody/antibody fragment, cell (e.g., T lymphocyte, APC), and/or composition (e.g., vaccine composition) according to the present disclosure, or any combination thereof, for use in the treatment of cancer e.g., as a cancer vaccine. The TAP sequences identified herein may be used for the production of synthetic peptides to be used i) for in vitro priming and expansion of tumor antigen-specific T cells to be injected into tumor patients and/or ii) as vaccines to induce or boost the anti-tumor T cell response in cancer patients, such as ALL patients.

In another aspect, the present disclosure provides the use of a TAP described herein (e.g., SEQ ID NOs: 1-88 and 92), or a combination thereof (e.g. a peptide pool), as a vaccine for treating cancer, such as a lymphoblastic leukemia, in a subject. The present disclosure also provides the TAP described herein, or a combination thereof (e.g. a peptide pool), for use as a vaccine for treating cancer, such as a lymphoblastic leukemia, in a subject. In an embodiment, the subject is a recipient of TAP-specific $CD8^+$ T lymphocytes. Accordingly, in another aspect, the present disclosure provides a method of treating cancer (e.g., of reducing the number of tumor cells, killing tumor cells), said method comprising administering (infusing) to a subject in need thereof an effective amount of $CD8^+$ T lymphocytes recognizing (i.e. expressing a TCR that binds) one or more MHC class I molecule/TAP complexes (expressed at the surface of a cell such as an APC). In an embodiment, the method further comprises administering an effective amount of the TAP, or a combination thereof, and/or a cell (e.g., an APC such as a dendritic cell) expressing MHC class I molecule(s) loaded with the TAP(s), to said subject after administration/infusion of said $CD8^+$ T lymphocytes. In yet a further embodiment, the method comprises administering to a subject in need thereof a therapeutically effective amount of a dendritic cell loaded with one or more TAPs. In yet a further embodiment the method comprises administering to a patient in need thereof a therapeutically effective amount of an allogenic or autologous cell that expresses a recombinant TCR that binds to a TAP presented by an MHC class I molecule.

In another aspect, the present disclosure provides the use of CD8+ T lymphocytes that recognize one or more MHC class I molecules loaded with (presenting) a TAP, or a combination thereof, for treating cancer (e.g., of reducing the number of tumor cells, killing tumor cells) in a subject. In another aspect, the present disclosure provides the use of CD8+ T lymphocytes that recognize one or more MHC class I molecules loaded with (presenting) a TAP, or a combination thereof, for the preparation/manufacture of a medicament for treating cancer (e.g., for reducing the number of tumor cells, killing tumor cells), such as a lymphoblastic leukemia, in a subject. In another aspect, the present disclosure provides CD8+ T lymphocytes (cytotoxic T lymphocytes) that recognize one or more MHC class I molecule(s) loaded with (presenting) a TAP, or a combination thereof, for use in the treatment of cancer (e.g., for reducing the number of tumor cells, killing tumor cells), such as a lymphoblastic leukemia, in a subject. In a further embodiment, the use further comprises the use of an effective amount of a TAP (or a combination thereof), and/or of a cell (e.g., an APC) that expresses one or more MHC class I molecule(s) loaded with (presenting) a TAP, after the use of said TAP-specific CD8+ T lymphocytes.

The present disclosure also provides a method of generating an immune response against tumor cells (leukemic cells, ALL cells) expressing human class I MHC molecules loaded with any of the TAP disclosed herein (e.g., SEQ ID NOs: 1-88 and 92) or combination thereof in a subject, the method comprising administering cytotoxic T lymphocytes that specifically recognizes the class I MHC molecules loaded with the TAP or combination of TAPs. The present disclosure also provides the use of cytotoxic T lymphocytes that specifically recognizes class I MHC molecules loaded with any of the TAP or combination of TAPs disclosed herein for generating an immune response against tumor cells expressing the human class I MHC molecules loaded with the TAP or combination thereof.

In an embodiment, the methods or uses described herein further comprise determining the HLA class I alleles expressed by the patient prior to the treatment/use, and administering or using TAPs that bind to one or more of the HLA class I alleles expressed by the patient. For example, if it is determined that the patient expresses HLA-A2*01 and HLA-B40*01, any combinations of the TAPs of SEQ ID NO: 2-22 (that bind to HLA-A2*01), and/or of the TAPs of SEQ ID NO: 61-66 (that bind to HLA-B40*01) may be administered or used in the patient.

In an embodiment, the cancer is a blood cancer, preferably leukemia such as acute lymphoblastic (or lymphocytic) leukemia (ALL), acute myeloid leukemia (AML), chronic myeloid leukemia (CML), hairy cell leukemia (HCL), myelodysplastic syndromes (MDS) and mixed lineage acute leukemias. In an embodiment, the leukemia is a lymphoblastic leukemia, in a further embodiment ALL (B-ALL or T-ALL), and preferably B-ALL. The ALL treated by the methods and uses described herein may be of any type or subtype (e.g., low-, intermediate- or high-risk ALL), such B lymphoblastic leukemia/lymphoma, not otherwise specified, B lymphoblastic leukemia/lymphoma with recurrent cytogenetic abnormalities (e.g., with t(9; 22) (Philadelphia chromosome), with t(1;19)(q23;p13), with t(12;21), with t(4;11) (q21;q23), with t(8;14)(q24;q32), with t(11;14)(p13;q11), with t(5;14), with hyperdiploidy (more than 50 chromosomes), with hypodiploidy (less than 50 chromosomes), or mixed lineage acute leukemias.

In an embodiment, the TAP, nucleic acid, expression vector, T cell receptor, antibody/antibody fragment, cell (e.g., T lymphocyte, CART or NK cell, APC), and/or composition according to the present disclosure, or any combination thereof, may be used in combination with one or more additional active agents or therapies to treat cancer, such as chemotherapy (e.g., *vinca* alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), transitional metal complexes, proteasome inhibitors, antimetabolites (such as nucleoside analogs), alkylating agents, platinum-based agents, anthracycline antibiotics, topoisomerase inhibitors, macrolides, retinoids (such as all-trans retinoic acids or a derivatives thereof), geldanamycin or a derivative thereof (such as 17-AAG), surgery, immune checkpoint inhibitors or immunotherapeutic agents (e.g., PD-1/PD-L1 inhibitors such as anti-PD-1/PD-L1 antibodies, CTLA-4 inhibitors such as anti-CTLA-4 antibodies, B7-1/B7-2 inhibitors such as anti-B7-1/B7-2 antibodies, TIM3 inhibitors such as anti-TIM3 antibodies, BTLA inhibitors such as anti-BTLA antibodies, CD47 inhibitors such as anti-CD47 antibodies, GITR inhibitors such as anti-GITR antibodies), antibodies against tumor antigens (e.g., anti-CD19, anti-CD22 antibodies), cell-based therapies (e.g., CAR T cells, CAR NK cells), and cytokines such as IL-2, IL-7, IL-21, and IL-15. In an embodiment, the TAP, nucleic acid, expression vector, T cell receptor, cell (e.g., T lymphocyte, APC), and/or composition according to the present disclosure is administered/used in combination with an immune checkpoint inhibitor. In an embodiment, the TAP, nucleic acid, expression vector, T cell receptor, cell (e.g., T lymphocyte, APC), and/or composition according to the present disclosure is administered/used in combination one or more chemotherapeutic drugs used for the treatment of ALL (e.g., vincristine, dexamethasone, prednisone, doxorubicin (Adriamycin), daunorubicin, cyclophosphamide, L-asparaginase (or pegaspargase), and/or high doses of methotrexate or cytarabine (ara-C), imatinib (Gleevec) or dasatinib (Sprycel), or in combination with another ALL therapy, for example stem cell/bone marrow transplantation.

The additional therapy may be administered prior to, concurrent with, or after the administration of the TAP, nucleic acid, expression vector, T cell receptor, antibody/antibody fragment, cell (e.g., T lymphocyte, CAR T or NK cell, APC), and/or composition according to the present disclosure.

MODE(S) FOR CARRYING OUT THE INVENTION

The present invention is illustrated in further details by the following non-limiting examples.

Example 1: Materials and Methods

Cell Culture

The Epstein-Barr virus (EBV)-transformed B-lymphoblastoid cell line (B-LCL) was derived from peripheral blood mononuclear cells as described previously[27]. Cells were grown in RPM11640 containing HEPES and supplemented with 10% heat-inactivated fetal bovine serum, penicillin/streptomycin, and L-glutamine and expanded in roller bottles. The cells were then collected, washed with PBS and either used fresh or stored at −80° C.

Cell Transplantation in Mice

The ALL specimens used in this study were collected and cryopreserved at the Leukemia Cell Bank of Quebec at Maisonneuve-Rosemont Hospital, Montreal. The project was approved by the Research Ethics Boards of Maisonneuve-Rosemont Hospital and of the Université de Montréal. For 10H080 sample, B-ALL cells were expanded in vivo after transplantation in mice as follows. NOD Cg-Prkdc$^{scid}$Il2rg$^{tm1Wjl}$/SzJ (NSG) mice were purchased from Jackson Laboratory and bred in a specific pathogen-free animal facility. All animal procedures were approved by the Deontology Committee on Animal Experimentation at the Université de Montréal. B-ALL cells were thawed at 37° C., washed and resuspended in RPMI (Life Technologies). A total of 1-2×$10^6$ B-ALL cells were transplanted via the tail vein into 8-12-week-old sub-lethally irradiated (250 cGy, 137Cs-gamma source) NSG mice. Mice were sacrificed 30-60 days post-injection when showing signs of disease. Spleens were mechanically dissociated and leukemic cells were isolated by Ficoll™ gradient. The purity and viability of the samples (usually >90%) were then assessed by flow cytometry. B-ALL cells were identified as human $CD45^+$ $CD19^+$. For 16 additional ALL samples, one hundred million cells were thawed (1 min in 37° C. water bath) and resuspended in 48 ml of 4° C. PBS. Two million cells (1 ml) were pelleted and resuspended in 1 ml Trizol™ for RNA-Sequencing while the remaining 98 million were pelleted and snap-frozen in liquid nitrogen for mass spectrometry analyses.

Immunoprecipitation of MHC I

The W6/32 antibodies (BioXcell) were incubated in PBS for 60 min at room temperature with PureProteome protein A magnetic beads (Millipore) at a ratio of 1 mg of antibody per mL of slurry. Antibodies were covalently cross-linked to magnetic beads using dimethylpimelidate as described previously[11]. The beads were stored at 4° C. in PBS pH 7.2 and 0.02% $NaN_3$. Biological replicates of cell pellets were resuspended in 1 mL PBS pH 7.2 and solubilized by adding 1 mL of detergent buffer containing PBS pH 7.2, 1% (w/v) CHAPS (Sigma) supplemented with Protease inhibitor cocktail (Sigma). After 60 min incubation with tumbling at 4° C., samples were spun at 16,000 g for 30 min at 4° C. Supernatants were transferred into new tubes containing magnetic beads coupled to W6/32 antibodies at a ratio of 10 □g of W6/32 antibody per 1×$10^6$ cells. Samples were incubated with tumbling for 180 min at 4° C. and placed on a magnet to recover bound MHC I complexes to magnetic beads. Magnetic beads were first washed with 8×1 mL PBS, then with 1×1 mL of 0.1×PBS and finally with 1×1 mL of water. MHC I complexes were eluted from the magnetic beads by acidic treatment using 0.2% formic acid (FA). To remove any residual magnetic beads, eluates were transferred into 2 mL Costar mL Spin-X centrifuge tube filters (0.45 μm, Corning) and spun 2 min at 855 g. Filtrates containing peptides were separated from MHC I subunits (HLA molecules and β-2 macroglobulin) using home-made stage tips packed with twenty 1 mm diameter octadecyl (C-18) solid-phase extraction disks (EMPORE). Stage tips were pre-washed first with methanol then with 80% acetonitrile (ACN) in 0.1% trifluoroacetic acid (TFA) and finally with 0.1% FA. Samples were loaded onto the stage tips and the peptides were retained on the stage tips while the HLA molecules and β-2 macroglobulin were found in the flow through. Stage tips were washed with 0.1% FA and peptides were eluted with 30% ACN in 0.1% TFA. The peptides were dried using vacuum centrifugation and then stored at −20° C. until MS analysis.

TMT Labeling

Samples were reconstituted in 100 μL of 200 mM HEPES buffer, pH 8.2. The TMT reagents (Thermo Fisher Scientific) were dissolved in 40 μL of anhydrous ACN (Sigma-Aldrich) and added to the peptides. The solution was gently mixed and incubated for 90 min without agitation at RT before the reaction was quenched by hydroxylamine (Thermo Fisher Scientific). Samples were desalted on Silica C18 UltraMicroSpin Column (The Nest Group), dried down and reconstituted in 4% FA (EMD Millipore). Benchmark evaluation was typically performed from MHC I peptide extracts corresponding to 2×$10^6$ B-LCL cells/injection. For extracts of less than 100×$10^6$ B-LCL cells, peptides were dissolved in 20 μL 200 mM HEPES buffer, pH 8.2 and mixed with 5 μL of 0.02 mg/μL of $TMT_0$126. For larger cell amounts up to 2,000×$10^6$ BLCL, 0.8 mg of $TMT_0$126 label was used, and the reaction volume was scaled accordingly. Note that TMT labeling efficiency can vary significantly, and label concentration should be adjusted to maximize yield[28].

For absolute quantification of MiHAs, synthetic peptides of concentration ranging from 0.75-192 fmoles were labeled with TMT-127N, TMT-128N, TMT-128C, TMT-129N, TMT-129C, TMT-130N, TMT-130C and TMT-131 while MHC I peptide extracts from 20×$10^6$ B-LCL cells were labeled with TMT-126. Note that the channel TMT-127C was unused to determine the extent of interfering fragment ions.

Faims

The FAIMS Pro (Thermo Fisher Scientific) inner and outer electrodes were separated by a 1.5 mm gap and heated to a temperature of 100° C. For this study, the inner and outer electrodes were heated to a common temperature of 100° C. to maximize ion transmission. Nitrogen ($N_2$) was used as a carrier gas with a temperature control gas flow rate of 5 L/min and a user carrier gas of 1.6 L/min. The dispersion voltage (DV) was set to −5000 V with a 3 MHz frequency for the high electric field. The FAIMS transit time was 40 ms. The compensation voltage (CV) for optimal transmission of target peptide ions in LC-FAIMS-MS/MS experiments was determined by infusing synthetic peptides and using CV Scan Tool in the Tune User Interface Software.

Mass Spectrometry

Vacuum dried peptides were resuspended 4% FA and analyzed by LC-MS/MS using an Easy nLC1000 coupled to a Tribrid Orbitrap Fusion mass spectrometer (Thermo Fisher Scientific). Peptides were separated on a custom C18 reversed-phase column (150 μm i.d.×200 mm, Jupiter Proteo 4 μm, 300 Å, Phenomenex) using a flow rate of 600 nL/min and a linear gradient of 5-40% ACN (0.2% FA) in 150 min, followed by 15 min at 70% ACN (0.2% FA) and 15 min re-equilibration at 5% ACN (0.2% FA). Survey scan (MS1) were acquired with the Orbitrap at a resolving power of 120,000 (at m/z 200) over a scan range of 300-1100 m/z with a target values of 5×$10^5$ with a maximum injection time of 100 ms. MS/MS spectra were acquired at higher energy collisional dissociation with a normalized collision energy of 35, and an exclusion time of 45 s. Up to twenty precursor ions were accumulated with a precursor isolation window of 1.6 m/z, an advanced gain control (AGC) of 2×$10^4$ with a maximum injection time of 500 ms and fragment ions were transferred to the Orbitrap analyzer operating at a resolution of 50,000 at m/z 200. For the TMT 10-plex analysis with FAIMS, the MS2 approach described above was used with minor modifications. The linear gradient was shortened to 60 min, followed by 15 min re-equilibration at 5% ACN (0.2% FA), and targeted LC-MS/MS used a list of selected precursor ions. The MS1 maximum injection time was set to 50 ms, and the isolation window for MS2 was 1 Th with an offset of 0.3 Th. For the SPS-MS3 method, the parameters for the MS scan were the same as for the FAIMS MS2 method (scan range m/z 300-1,100, Orbitrap resolution 120,000, AGC $5\times10^5$ and maximum injection time 50 ms) followed by a 3 sec top speed approach for MS2 in the ion trap (Isolation window 0.7 Th, CID at 35% collision energy, normal scan rate mode, AGC $2\times10^4$ with maximal injection time of 50 ms) followed by the selection of synchronous precursor ions for MS3 acquisition (scan range m/z 100-500, Orbitrap resolution of 50,000, AGC of $1\times10^5$, maximum injection time of 300 ms, 4 notches, isolation window of 2.0 Th and a collision energy of up to 65%).

Peptide Identification and TMT Quantification

Database searches were performed using PEAKS X (Bioinformatics Solutions Inc.) Mass tolerances for precursor and fragment ions were set to 10 ppm and 0.02 Da, respectively. Searches were performed without enzyme specificity and with variable modifications for deamidation (N, Q) and oxidation (M). MAPDP was used to generate subject-specific protein sequence databases[29]. Protein entries are derived from the Ensembl reference genome release 75 (GRCh37.p13) and 88 (GRCh38.p10) respectively for B-LCL and B-ALL[30]. Single amino-acid polymorphism derived from RNA-Seq data sets available in the NCBI Bioproject database: B-BCL: PRJNA286122, B-ALL: PRJNA454807[31,32] were incorporated in the protein entries. Polymorphisms were called by Casava (Illumina) for B-LCL and FreeBayes 1.0.2[33] for B-ALL. Only SNV with a quality score above 20 were included. Additionally, only expressed transcripts quantified by Kallisto v0.43.0 were retained for B-ALL[34].

Bioinformatic Analyses

PEAKS results were loaded into MAPDP and the MHC I peptide selection was achieved using the following criteria: peptide false discovery rate was limited to 5%, peptide length between 8-15 residues, and a threshold of top 2% ranked predicted sequences according to NetMHC 4.0. MiHAs were selected using MAPDP based on dbSNP human b151 GRCh37p13 and gnomAD exomes r2.1.1 annotations and the following criteria: the peptide sequence must not be present in another protein (single genetic origin), must not derive from HLA or IgG genes, and the minor allele frequency (MAF) must be higher or equal to 0.05. MS/MS of MiHA were manually validated (4 consecutives fragment above background required). Peak areas for MiHA peptides were extracted from PEAKS label-free quantification to compare the detection between experimental methods and cell amounts.

Identification and Validation of Tumor Specific Antigens (TSAs)

Tumor specific antigens were identified from ALL samples according to the method previously described[31]. To assign a genomic location to TSA candidates, reads containing MHC peptide-coding sequences were mapped on the reference genome (GRCh38.88) using BLAT (tool from the UCSC genome browser). For TSA candidates with a clear genomic location, IGV (integrative genome browser) was used to visualize expression of MHC peptide-coding sequences in ALL vs. mTECs RNA sequencing data and to exclude sequences originating from a hypervariable region (MHC, Ig or TCR genes) or for which the mutation overlaps a germline polymorphism reported in dbSNP build 149. Finally, expression of TSA candidates in normal cells was assessed using RNA sequencing data from two sources as described[31]: i) human mTECs (GEO GSE127825 and GSE127826) and ii) 28 adult human tissues (~50 donors per tissue), which had been sequenced by the GTEx consortium and downloaded from the GTEx Portal.

Example 2: Isobaric Peptide Labeling Using Tandem Mass Tag Increased Immunopeptidome Coverage To enhance the detection of MHC I peptides, chemical labeling of free amino groups was first investigated using of tandem mass tag (TMT)[35]. This modification enables the parallel quantification of different samples by monitoring reporter fragment ions originating from isobaric precursor ions. The number of identifications for the native and TMT-modified peptides purified from immunoisolated MHC I complex of an Epstein-Barr virus (EBV) transformed B-LCL obtained from normal peripheral mononuclear cells was compared (FIG. 1A). These immortalized cells expressed approximately $3\times10^6$ MHC I molecules/cell based on flow cytometry analyses[11]. High-resolution HLA genotyping revealed that these cells possessed five HLA class I alleles: A*01:01, A*02:01, B*07:02, B*44:03 and C*07:02.

Figure 6C:
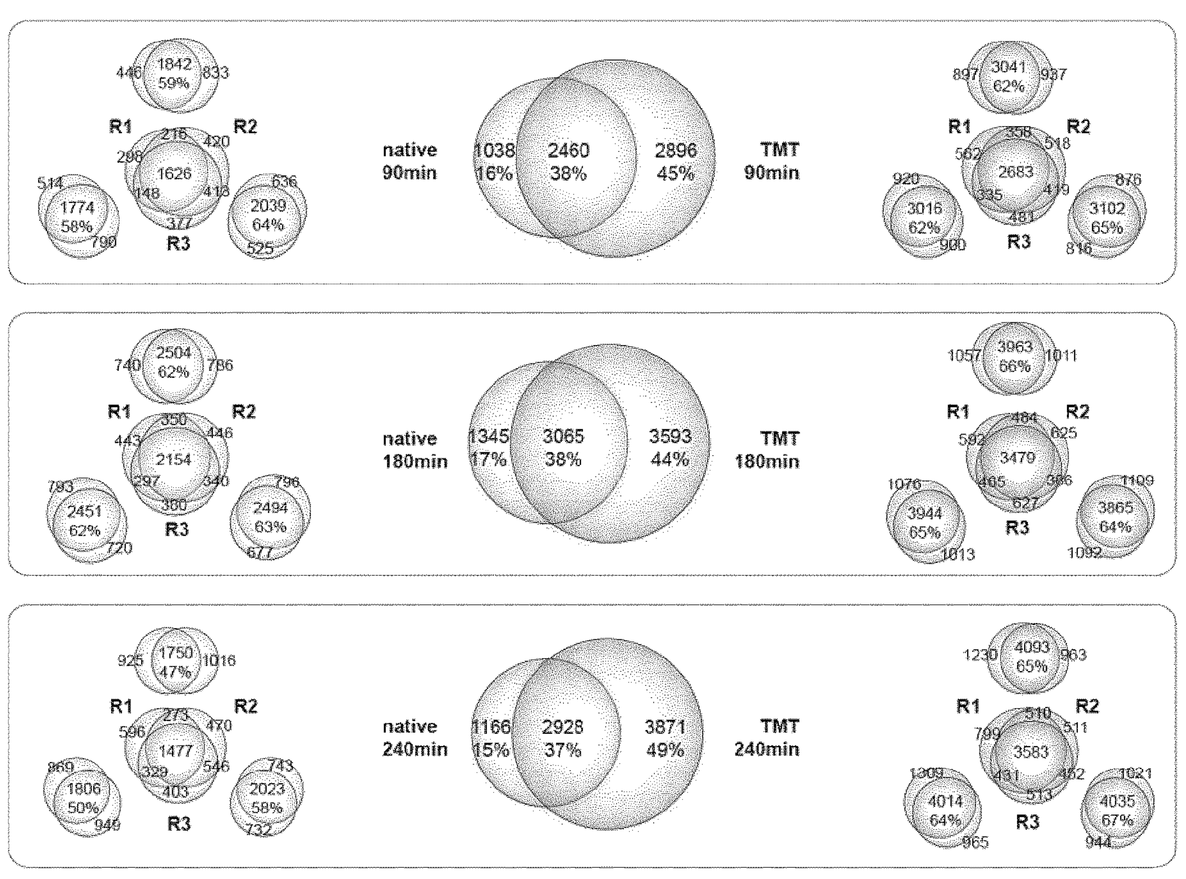
FIG. 6C shows the overlap in the number of identifications for native and TMT-labeled MHC I peptides across replicate injections.
Figures 7A, 7B, 7C:
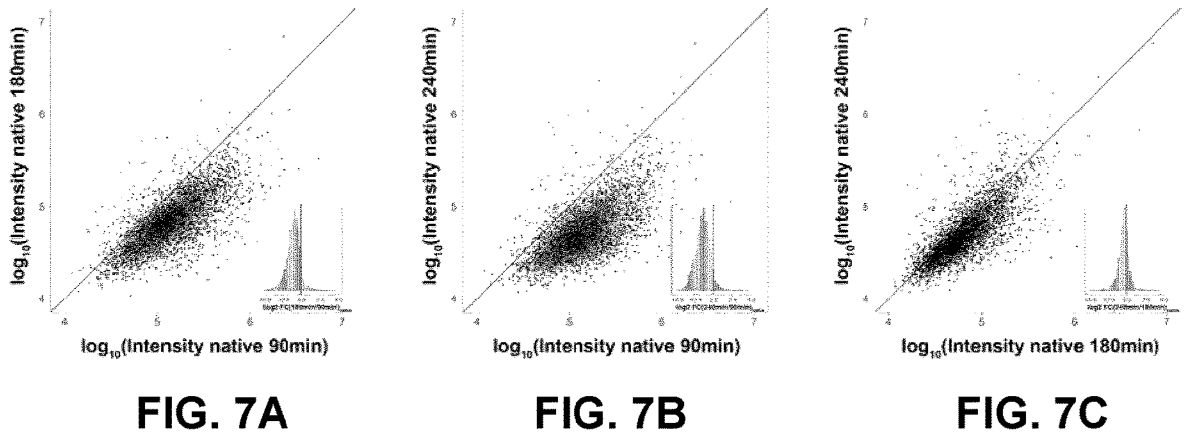
FIGS. 7A-F show comparison of MHC I peptide intensities obtained between different gradient elution conditions. Native MHC I peptides intensities at 90 and 180 min (FIG. 7A) 90 and 240 min (FIG. 7B) and 180 and 240 min (FIG. 7C) gradient elution. TMT-labeled MHC I peptides intensities at 90 and 180 min (FIG. 7D) 90 and 240 min (FIG. 7E) and 180 and 240 min (FIG. 7F) gradient elution.
Figures 7D, 7E, 7F:
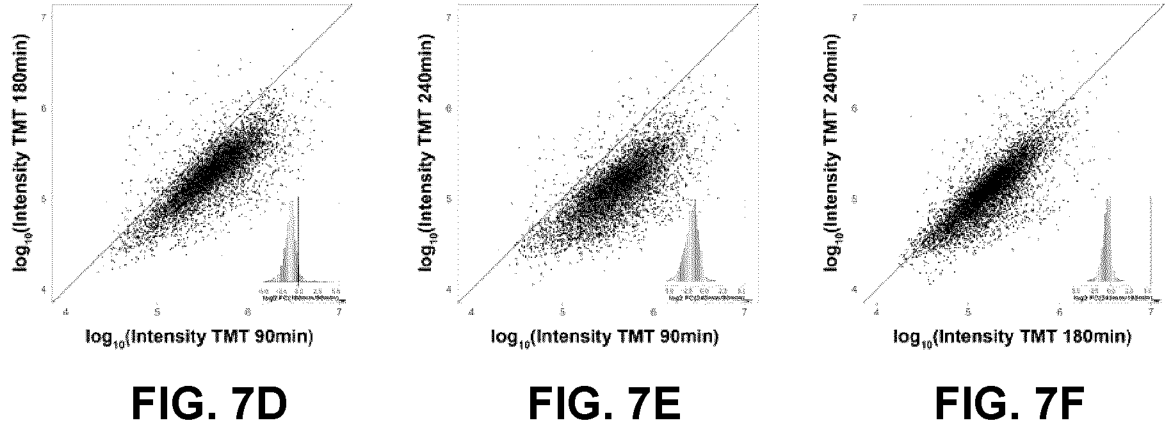

Triplicate LC-MS/MS analyses of native and TMT-derivatized MHC I peptides from $2\times10^6$ B-LCL cells for gradient elution of 90, 180, and 240 min was performed (FIGS. 6A-C). For native peptides, an optimal number of identifications was observed for the 180 min gradient resulting in 3,235 unique peptides per run on average. TMT labeling of the corresponding samples enabled the identification of 4,984 unique peptides on average per run for the same gradient length, and only a 5% increase in identification was observed for the 240 min gradient. It is noteworthy that shorter gradient led to more intense peptide signals, though a lower number of identifications were typically observed for both native and TMT-labeled peptides (FIGS. 7A-F). Gradient elution extending beyond 180 min did not lead to significant improvement in the number identification possibly due to peak broadening and reduced peak intensity. More than 62% overlap in peptide identification was obtained between replicates of each gradient length for both sets of samples. Altogether, a total of 6,658 unique TMT-modified MHC I peptides was identified in the 180 min LC-MS/MS runs, of which 3,065 peptides were common with their native counterparts (FIG. 1B). On average, TMT labeling improved the number of identified MHC I peptides by 50%, and the corresponding peptides displayed 10% higher identification scores than native peptides (FIG. 1C). Interestingly, these analyses also enabled the identification of 9 MiHAs, several of which were not identified in the native MHC I peptides.

Next, the changes in physicochemical characteristics of native and derivatized MHC I peptides in terms of hydrophobicity, MS signal and charge state distribution was examined. TMT-labeling generally enhanced the formation of multi-protonated peptide ions, and a larger proportion of TMT-labeled peptides were observed as doubly- and triply-protonated ions (FIG. 1D). The conversion of the primary amine of native peptides into a moiety containing a dimethyl piperidine enhanced their proton affinity and partly explained the propensity of TMT-labeled peptides to form higher charge state peptide ions. It was also noted that TMT derivatization renders MHC I peptides more hydrophobic as reflected by their increased retention times (FIG. 1E). This feature was advantageously exploited recently to improve the detection of hydrophilic phosphopeptides that can be underrepresented in large-scale phosphoproteomic experiments[36]. The systematic analysis also revealed that TMT labeling improved the MS signal compared to the corresponding native peptides, and increased the detection of low abundance peptides (FIG. 1F). However, it is unclear if the enhanced MS signal observed for TMT-labeled peptides is associated with the higher proportion of organic solvent at which peptides eluted or the enhanced formation of multiply-charged ions. Nonetheless, TMT-labeling of MHC I peptides favored their detection and increased the immunopeptidome coverage.

Figure 8:
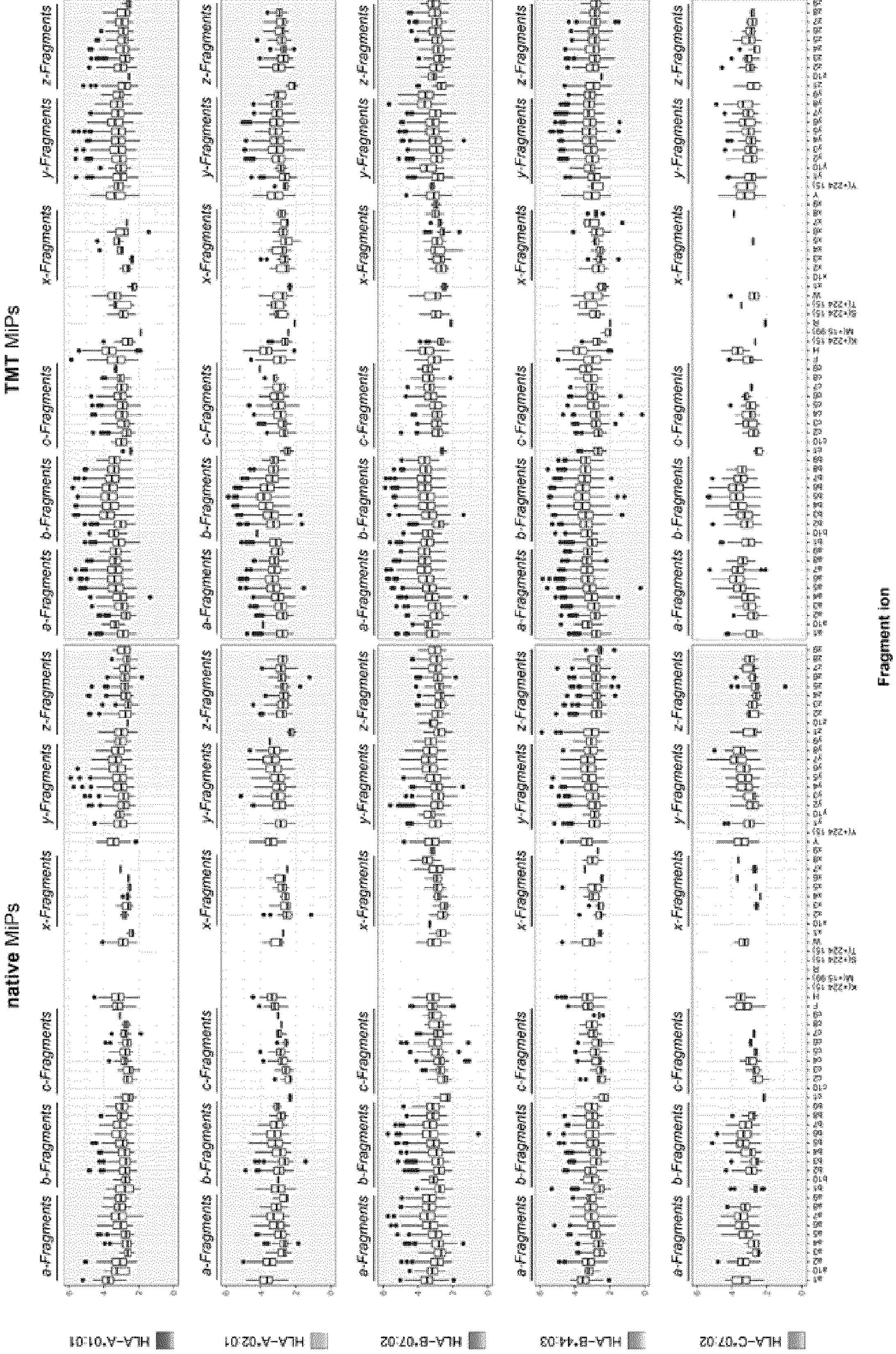
FIG. 8 shows the distribution of fragment ions for native and TMT-labeled MHC I peptides from B-LCL cells.

To determine if TMT labeling had an impact on MS/MS fragmentation of MHC I peptides or the HLA allele groups detected, the distribution of identified peptides and their fragment ions were analyzed. Generally, it was found that N-terminus peptide labeling with TMT favored the formation of b-type fragment ions compared to native MHC I peptides where y-type fragments were more prominent (FIG. 2A). it was also noted that a-, b-, and y-type fragment ions were observed for both native and TMT-labeled peptides with a significantly lower occurrence of other types of fragment ions (FIG. 8). The b1 ion appeared to be highly abundant in TMT-labeled peptides but not in native peptides, and former peptides tend to have more and stronger b-type ions than their native counterparts irrespective of their HLA allele groups. The intensity of y ions in TMT-labeled peptides decreased appreciably with the length of the y-type ion series.

These observations indicate that TMT-labeling changed the distribution and pattern of peptide fragmentation. Interestingly, these changes favored the identification of TMT-labeled peptides of underrepresented HLA allele groups, most notably A*01:01, A*02:01 and B*44:03 (FIG. 2B). While the relative distribution of peptides for each corresponding allele groups remained similar between native and TMT-labeled peptides, an increase of 45-118% in the number of unique peptides for these three groups was observed. For HLA allele groups B*07:02 and C*07:02, a change of −2% and 23%, respectively, was observed. It was also noted that the number of a-, b- and y-type fragment ions observed was higher upon TMT labeling compared to native peptides (14 vs. 11 fragment ions), and that allele groups A*01:01, A*02:01 and B*44:03 displayed the highest number of fragment ions (FIG. 2C). The fact that HLA allele groups display different response upon TMT labeling possibly reflect the variability in N-termini reactivity towards the N-hydroxysuccinimide ester and the influence of neighboring amino acids. Taken together, these results indicate that TMT labeling of MHC I peptides enhanced the comprehensiveness of peptide analyses and favored the identification of HLA allele groups such as A*01:01, A*02:01 and B*44:03 that were underrepresented in the native immunopeptidome of B-LCL cells.

Figure 3A:
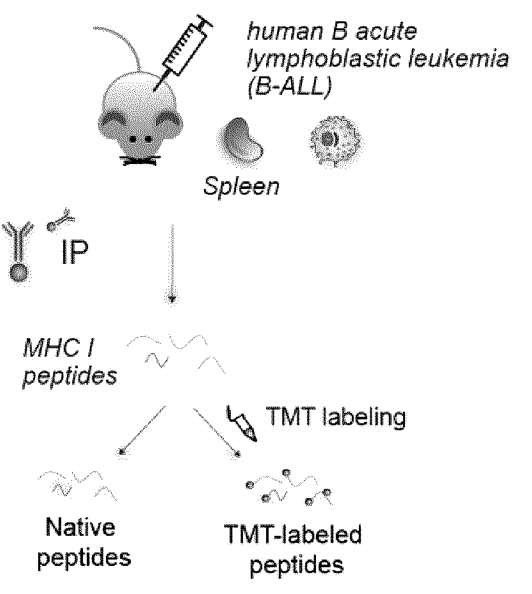
FIG. 3A is a schematic of workflow for the analysis of native and TMT-labeled MHC I peptides. Human B-ALL cells (10H080) were transplanted into NSG mice, spleen was excised 30-60 d post-injection, and leukemic cells isolated by density gradient. B-ALL cells were lysed and MHC I peptides isolated by immunoaffinity purification. Half of the purified peptides were subjected to TMT labeling prior to LC-MS/MS analyses of both native and TMT-labeled peptides.

Example 3: Immunopeptidome Analyses of B-ALL Cells Uncovers New Tumor-Specific Antigens The impact of TMT-labeling on a second cell model derived from human B-ALL cells from a leukemic patient was evaluated. These cells were expanded in vivo by transplanting them in mice, and harvesting the spleen of injected animals after 30-60 d (FIG. 3A). B-ALL cells express a lower number of MHC I molecules at the cell surface than B-LCL ($5\times10^5$ molecules/cell)[11]. Preliminary experiments were performed on 100 million B-ALL cells isolated from mice using Ficoll™ density gradient. Cells were lysed and MHC I peptides extracted following immunoaffinity purification. Purified peptides were either kept in their native forms or derivatized with TMT prior to LC-MS/MS analyses. To uncover peptide variants that are not present in reference proteome databases, a proteogenomic strategy where a customized database from the RNA sequencing of the tumor sample was built, and the repertoire of MHC I peptides coded by all genomic regions was comprehensively mapped[31], was used.

Figure 3B:
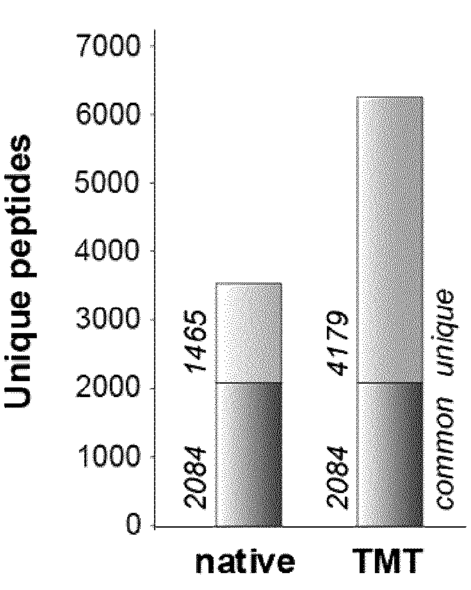
FIG. 3B shows the distribution of unique identification for native and TMT-labeled peptides.
Figure 3C:
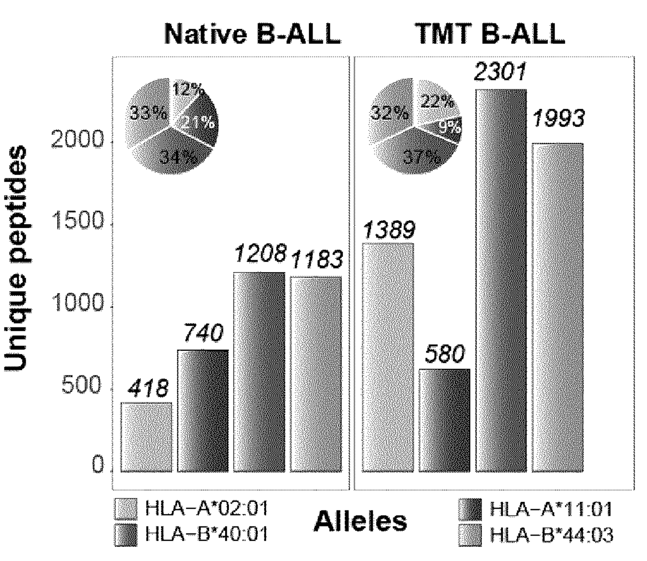
FIG. 3C shows the identification of MHC I peptides for different HLA allele groups.

A total of 7,728 unique MHC I peptides, of which 2,084 peptides were common to both native and TMT-labeled peptides (FIG. 3B), was identified. It was observed that TMT-labeling enhanced the number of identified MHC I peptides by 76%, and enabled the identification of an additional 4,179 peptides compared to 1,465 peptides for their native counterparts. From the 3,549 and 6,263 MHC I peptides identified in the native and TMT-labeled extracts of B-ALL cells, 12-22%, 9-21%, 34-37%, and 32-33% were presented by allele groups A*02:01, A*11:01, B*40:01 and B*44:03, respectively (FIG. 3C). The relative distribution of allelic products of native and TMT-labeled MHC I peptides was similar except for A*11:01 where a reduced number of identifications was observed upon TMT labeling. This allele group is characterized by a Lys residue at position 9, and variable labeling of this site and the amino group of the N-terminus could account for the lower number of identified TMT peptides. Peptides corresponding to the other three alleles showed significant gains in identification following TMT-labeling, especially A*02:01 where a 3-fold increase in the number of identified peptides was obtained. These results confirmed earlier findings observed for B-LCL cells where TMT labeling enhanced the number of identified MHC I peptides.

Figure 3D:
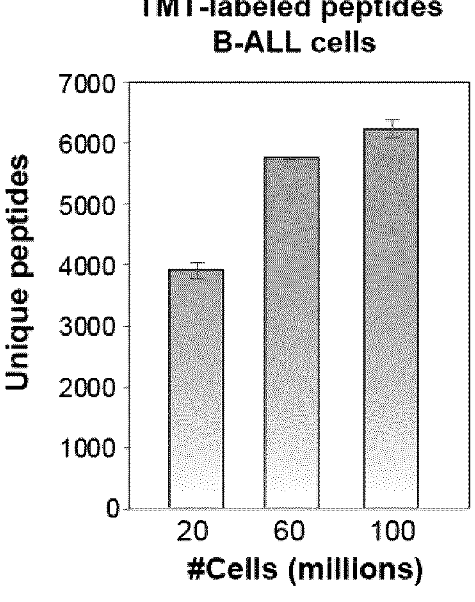
FIG. 3D shows the number of TMT-labeled peptides identified from an increasing amount of isolated B-ALL cells.
Figure 9A:
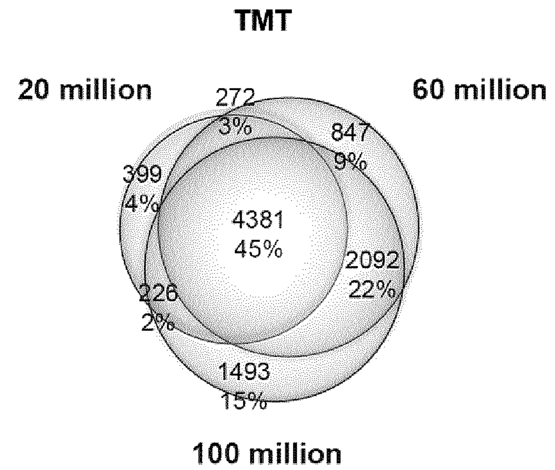
FIG. 9A depicts a Venn diagram showing the number of identified MHC I peptides for 20, 60 and 100 million B-ALL cells (triplicate injection).
Figure 9B:
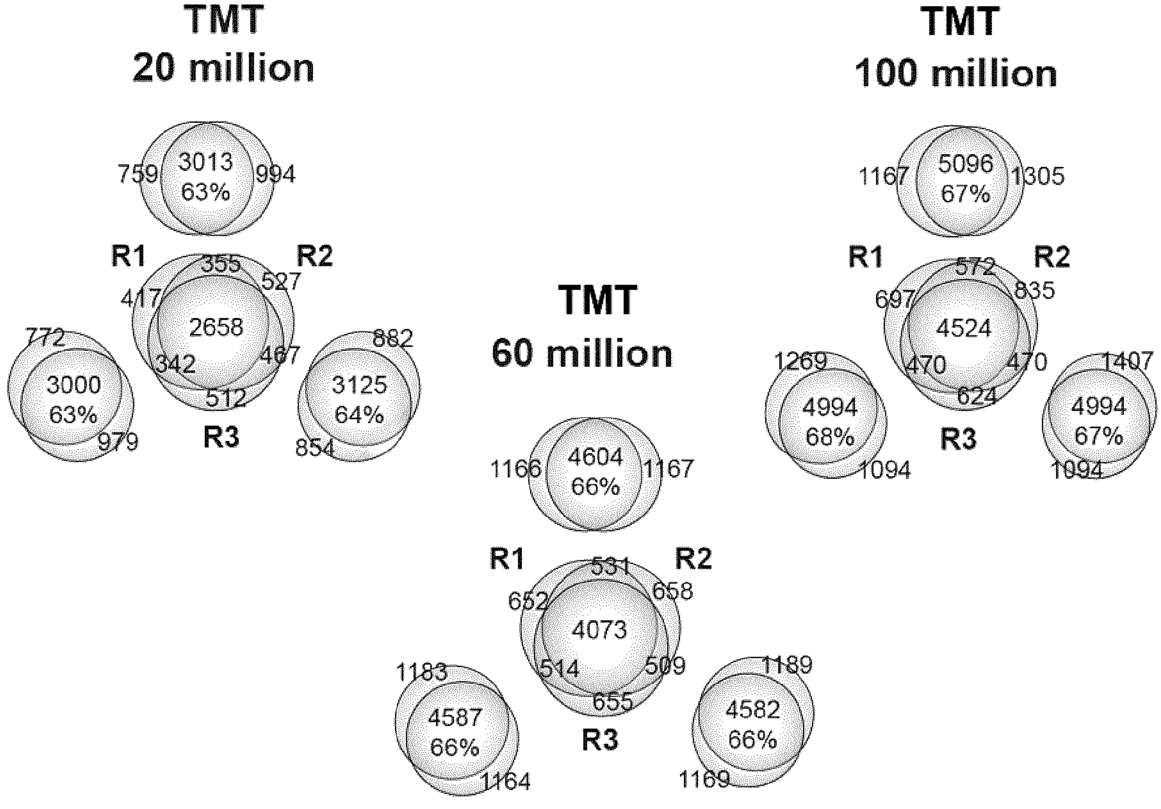
FIG. 9B shows the overlap of peptide identification across triplicate injection.

To evaluate the scalability of this approach, triplicate analyses of TMT-labeled peptides from 20, 60, and 100 million cells were conducted (FIG. 3D). Reproducible numbers of identification were observed for each sample set, and more than 60% of identified peptides were shared across replicates (FIGS. 9A-B). A progressive increase in the number of identified MHC I peptides ranging from 3,919 to 6,251 for extracts of 20 to 100 million cells was observed. The relatively modest increase in identification from 60 to 100 million cells possibly reflects the limited dynamic range of peptide sequencing and the stochastic sampling of MS/MS spectra in an increasing sample complexity.

The improved immunopeptidome coverage obtained using TMT labeling enabled the identification of low abundance peptides and variants that were not typically observed in native MHC I peptides. Altogether, the detailed analysis of TMT-labeled peptides identified a total of 6,971 unique MHC I peptides found in at least two replicates (FIG. 9A). Among these, 81 MiHAs with a MAF≥0.05 were identified, a level that corresponded to a balanced genetic polymorphism among the human population[37]. In the context of leukemia immunotherapy, MiHAs found on the surface of malignant cells can trigger a strong graft versus tumor effect[38]. Previous investigations on transplanted B-ALL cells enabled the identification of only 5 MiHAs from native MHC I peptides[11]. Clearly, TMT labeling facilitated the comprehensive profiling of the immunopeptidome of leukemic cells to identify minor antigens of relevance for allogeneic hematopoietic cell transplantation.

Building upon the improved sensitivity of the TMT labeling approach for immunopeptidome analyses, the subpopulation of MHC I peptides representing putative TSAs was next determined in 10H080 sample as well as 16 additional primary ALL samples. In this category, mTSAs that derived from polymorphic DNA sequences originating from either exonic or non-exonic regions, and aberrantly expressed TSAs (aeTSAs) that result from the deregulated expression of unmutated transcripts not expressed in normal somatic cells, including medullary epithelial cells (mTECs), were regrouped. To select cancer-specific TSAs, only peptide candidates for which no transcript was detected in mTEC cells of human thymi were considered, as they express most known genes and play a central role in immune tolerance[31,39]. Accordingly, a total of 92 TSAs was identified in the immunopeptidome of 17 primary ALL samples, of which 88 TSAs are novel, 3 (RIFGFRLWK, SLTALVFHV, TSFAETWMK) were previously identified in human B-ALL samples[31], and 1 (IPLNPFSSL) was previously identified in human AML sample[42]. All TSA peptide candidates corresponded to aeTSAs and no mTSA were detected. To ensure that the expression of aeTSA candidates was cancer-specific, their RNA expression in 27 human peripheral tissues downloaded from the Genotype-Tissue Expression (GTEx) was analyzed. Peptide candidates whose coding RNA sequence was expressed at levels <10 reads per hundred million (rphm) in any peripheral tissue other than those with low expression of MHC (e.g., brain, nerve, testis) were thus selected. Out of the 92 aeTSA candidates, two were expressed in the testis, indicating that some cancer germline antigens (CGAs) driven by epigenetic alterations are aeTSAs but that most aeTSAs are not CGAs.

Figure 4A:
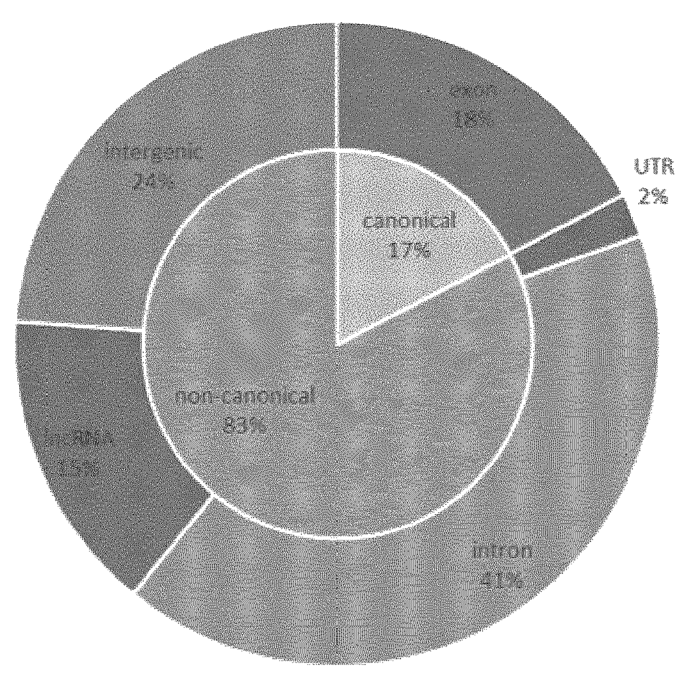
FIG. 4A depicts a pie chart showing the translational reading frame (inner circle) and the detailed genomic origin (outer circle) of TSAs (n=92) identified from a total of 17 ALL samples.

Features of all aeTSAs are reported in Table 1. It is noteworthy that the proteogenomic approach may underestimate the total number of aeTSAs resulting from atypical translation (5'UTR, 3'UTR, intergenic, frameshift). Indeed, to minimize the number of false positives in the TSA list, aeTSAs for which their RNA was expressed in some normal tissues, not knowing which reading frame could be translated, were excluded. It was found that the majority of TSAs identified herein corresponded to noncanonical translation events (FIG. 4A). Interestingly, a large proportion of aeTSAs originated from intronic (41%) and intergenic (24%) regions, while other TSAs were assigned to UTRs (6%), noncoding RNA (15%) and exonic regions (18%).

TABLE 1

Features of the aeTSA identified in the studies described herein

| Sequence (SEQ ID NO:) | Status | Genomic Position | Origin | Ensembi Transcript id | Gene |
|---|---|---|---|---|---|
| NEQTTILY (1) | Novel | chr9: 2037127-2037150 | intron | ENST00000382203 | SMARCA2 |
| ALFSNEVSL (2) | Novel | chr18: 13509916-13509942 | intron | ENST00000587905 | LDLRAD4 |
| FIPDLFTEL(3) | Novel | chr7: 30 255 455-30 255 481 | intergenic | N/A | N/A |
| FLLDHILTI (4) | Novel | chr1: 158481592-158481618 | IncRNA | ENST00000535880 | AL365440.2 |
| FLLESRETL(5) | Novel | chr11: 4060859-4060885 | intron | ENST00000532919 | STIM1 |
| FLLPTSLSL (6) | Novel | chr2:58 187 587-58 187 613 | intron | ENST00000403295 | FANCL |
| FLLSDELLL (7) | Novel | chr19: 12436696-12436722 | intron | ENST00000301547 | ZNF443 |
| GLATAVWLL (8) | Novel | chr10: 45 303 916-45 303 942 | exon | ENST00000553795 | OR13A1 |
| GLLTASIFL (9) | Novel | chr12: 10054315-10054341 | exon | ENST00000355819 | CLEG9A |
| GTLCLLTFI (10) | Novel | chr2: 157 333 520-157 333 546 | intergenic | N/A | N/A |
| KLLQPLPIT (11) | Novel | chr12: 46715090-46715116 | IncRNA | ENST00000611243 | AC008014.1 |
| LLQNLIVLL (12) | Novel | chr7: 158786203-158786229 | intron | ENST00000251527 | ESYT2 |
| LLSLYLVSI (13) | Novel | chr21: 15528085-15528109 | intergenic | N/A | N/A |
| LMLLFVVLL (14) | Novel | chr7: 961442-961468 | intron | ENST00000457254 | COX19 |
| SLANETHTL (15) | Novel | chr17: 3729513-3729539 | exon | ENST00000263087 | ITGAE |
| VLLDFPALL (16) | Novel | chr21: 42683073-42683099 | intergenic | N/A | N/A |
| VLLSKILYP (17) | Novel | chr5: 102751630-102751656 | intergenic | N/A | N/A |
| WLVEKLSGV (18) | Novel | chrX: 148221715-148221741 | intergenic | N/A | N/A |
| YLFAHSIIL (19) | Novel | chr1: 198738082-198738108 | intergenic | N/A | N/A |
| YLGYAVAV (20) | Novel | chr17: 3753909-3755123 | exon | ENST00000263087 | ITGAE |
| YLQEISLRL (21) | Novel | chr10: 128316002-128316028 | IncRNA | ENST00000630252 | LINC01163 |
| SLLGIGLLA (22) | Novel | chr8: 17237977-17238003 | intron | ENST00000523917 | CNOT7 |
| AAMESPIQSK (23) | Novel | chr2: 1800191-1800220 | IncRNA | ENST00000638628 | AC093390.2 |
| ALFGFVGFPNK (24) | Novel | chr7: 27151832-27151864 | IncRNA | ENST00000518451 | HOXA3 |
| ALFVLTSIK (25) | Novel | chr6: 110184721-110184747 | intron | ENST00000307731 | CD40 |

TABLE 1-continued

| Features of the aeTSA identified in the studies described herein | | | | | |
|---|---|---|---|---|---|
| ATSLTIQEK (26) | Novel | chr2: 123839904-123839930 | intergenic | N/A | N/A |
| AVAVPLLPR (27) | Novel | chr2: 123839872-123839898 | intergenic | N/A | N/A |
| GTISGGFFK (28) | Novel | chr12: 68333644-68333664; chr12: 68442064-68442069 | IncRNA | ENST00000546086 | LINC02384 |
| GVANSLLK (29) | Novel | chr6: 156 112 915-156 112 938 | intergenic | N/A | N/A |
| GVSPVLFLK (30) | Novel | chr19: 36 684 826-36 684 852 | intergenic | N/A | N/A |
| LLGLPQPPK (31) | Novel | chrY: 19072786-19072812 | IncRNA | ENST00000331787 | TTTY14 |
| LSSRLPLGK (32) | Novel | chr9: 96 398 754-96 398 780 | intron | ENST00000375256 | ZNF367 |
| NLLFSRVFK (33) | Novel | chr2: 143159367-143159393 | intron | ENST00000295095 | ARHGAP1 5 |
| STGVLTVLK (34) | Novel | chr2: 1810045-1810071 | IncRNA | ENST00000638628 | AC093390.2 |
| SVFDRTNNR (35) | Novel | chr1: 110491121-110491147 | intergenic | N/A | N/A |
| SVVPHPLQK (36) | Novel | chr14: 22322773-22322799 | intergenic | N/A | N/A |
| TTSSIYIRK (37) | Novel | chr3: 66781042-66781068 | intergenic | N/A | N/A |
| LYTFIKHEF (38) | Novel | chr4: 174495485-174495511 | exon | ENST00000510835 | HPGD |
| SYFDPSYSNF (39) | Novel | chr7: 92658800-92658829 | intergenic | N/A | N/A |
| SYLASFLLY (40) | Novel | chr9: 105513917-105513943 | intron | ENST00000394926 | FSD1L |
| VYSPSPLNF (41) | Novel | chr2: 1782377-1782403 | intergenic | N/A | LTR48B |
| VYTQVSAF (42) | Novel | chr19: 685806-685829 | exon | ENST00000613411 | PRSS57 |
| YSVLTVTF (43) | Novel | chr3: 42559254-42559277 | intron | ENST00000451653 | SEC22C |
| NLGLFLSY (44) | Novel | chr1: 107730876-107730899 | intron | ENST00000370056 | VAV3 |
| AVGGFRSSW (45) | Novel | chr17: 4448248-4448274 | exon | ENST00000575194 | SPNS3 |
| SQVQAVLLAW (46) | Novel | chr1: 113944573-113944602 | intron | ENST00000369558 | HIPK1 |
| QTNSGSLAR (47) | Novel | chr6: 144045542-144045568 | intron | ENST00000628069 | PLAGN1 |
| DVAGVGMPK (48) | Novel | chr1: 98044989-98045015 | IncRNA | ENST00000634594 | MIR137HG |
| DVMASLARV (49) | Novel | chr17: 3759461-3759487 | exon | ENST00000263087 | ITGAE |
| EVGAVFAVL (50) | Novel | chr3: 151369504-151369530 | exon | ENST00000474524 | MED12L |
| VVADILLSV (51) | Novel | chr17: 4478617-4486233 | exon | ENST00000355530 | SPNS3 |
| SSLSGPVSSL (52) | Novel | chr14: 99265648-99265677 | intergenic | N/A | N/A |
| AFRVIVAL (53) | Novel | chr10: 11556133-11556156 | intron | ENST00000379237 | USP6NL |
| EHYNKVVVM (54) | Novel | chr14: 106465542-106465568 | intergenic | N/A | N/A |
| VQAQVLEAI (55) | Novel | chr3: 45886725-45886751 | intron | ENST00000483279 | LZTFL1 |
| NNMAIIYSY (56) | Novel | chr9: 112611600-112611626 | intron | ENST00000374244 | KIAA1958 |
| EPSHSINVY (57) | Novel | chr7: 38316972-38316998 | intergenic | N/A | N/A |
| IPVGSGLGYVL (58) | Novel | chr17: 4446186-4446914 | exon | ENST00000355530 | SPNS3 |
| DHDIGVYSV (59) | Novel | chr22: 22245035-22245061 | exon | ENST00000403807 | VPREB1 |
| HFEWQPPL (60) | Novel | chr11: 36574859-36574882 | exon | ENST00000299440 | RAG1 |
| GEFLVPLSL (61) | Novel | chr11: 64490401-64490427 | intergenic | N/A | N/A |
| GEVDGAQQAM (62) | Novel | chr11: 61880352-61880381 | intron | ENST00000278829 | FADS3 |
| IEEVSQGLL (63) | Novel | chr19: 11155732-11155758 | exon | ENST00000592540 | SPC24 |

TABLE 1-continued

Features of the aeTSA identified in the studies described herein

| | | | | | |
|---|---|---|---|---|---|
| IESEDFGFWSL (64) | Novel | chr7: 136 177 375-136 177 407 | IncRNA | ENST00000445293 | AC078845.1 |
| LENSGFILI (65) | Novel | chr5: 134 948 472-134 948 498 | intron | ENST00000254908 | PCBD2 |
| REPLEILITL (66) | Novel | chr19: 41456461-41456487 | IncRNA | ENST00000588495 | PCAT19 |
| EETDAYKSL (67) | Novel | chrX: 131734445-131734471 | IncRNA | ENST00000637577 | FIRRE |
| SELQLPVTF (68) | Novel | chr7: 76349523-76349549 | intron | ENST00000307630 | YWHAG |
| QEIATSHNI (69) | Novel | chr15: 40622254-40622280 | exon | ENST00000399668 | KNL1 |
| AQFLLFIA (70) | Novel | chr7: 19703301-19703324 | intron | ENST00000222567 | TWISTNB |
| FEISSVTTA (71) | Novel | chr17: 3747932-3747958 | exon | ENST00000263087 | ITGAE |
| KEVGGLRSA (72) | Novel | chr17: 80770839-80770865 | intergenic | N/A | N/A |
| TEFGPVIG (73) | Novel | chrX: 38573320-38573343 | intron | ENST00000378482 | TSPAN7 |
| ISLPALEVL (74) | Novel | chr2: 47706606-47706632 | intron | ENST00000606499 | MSH6 |
| LPSPPLPPSL (75) | Novel | chr1: 167630182-167630211 | 5′UTR | ENST00000367854 | RCSD1 |
| LYLPSVVLI (76) | Novel | chr7: 39957700-39957726 | intron | ENST00000611390 | CDK13 |
| RPPAPLLPVL (77) | Novel | chr5: 43095886-43095915 | intron | ENST00000514169 | ZNF131 |
| SLHYSVSL (78) | Novel | chr4: 2846794-2846817 | intron | ENST00000264758 | ADD1 |
| SLPDHQGVL (79) | Novel | chr10: 96295027-96295053 | IncRNA | ENST00000454484 | AL136181.1 |
| EAVSQGKDF (80) | Novel | chr12: 104494469-104494495 | intron | ENST00000303694 | CHST11 |
| YSSYLSIHY (81) | Novel | chr2: 113187675-113187701 | intron | ENST00000245796 | PDS4 |
| ASLGLSLAL (82) | Novel | chr3: 183977404-183977430 | intron | ENST00000334444 | ABCC5 |
| LCHRTPPSL (83) | Novel | chr5: 179764917-179764943 | intron | ENST00000292599 | MAML1 |
| LSISPFQAI (84) | Novel | chr14: 106198472-106198498 | intergenic | N/A | N/A |
| GWGGSPLYL (85) | Novel | chr9: 27441807-27441833 | intron | ENST00000262244 | MOB3B |
| YFDPSYSNF (86) | Novel | chr7: 92658803-92658829 | intron | ENST00000265734 | CDK6 |
| ISLSSIVSV (87) | Novel | chr6: 31755981-31756007 | intron | ENST00000468136 | MSH5 |
| LSISSLVSV (88) | Novel | chrX: 136719927-136719953 | intron | ENST00000370620 | ARHGEF6 |
| SLTALVFHV (89) | Prev. reported in B-ALL | chr14: 95710553-95710559 | 3′UTR | ENST00000554012 | TCL1A |
| RIFGFRLWK (90) | Prev. reported in B-ALL | chr1: 80641339-80641365 | IncRNA | ENST00000418041 | LINC01781 |
| TSFAETWMK (91) | Prev. reported in B-ALL | chr7: 43947484-43947510 | Intron | ENST00000415051 | POLR2J4 |
| IPLNPFSSL (92) | Prev. reported in AML | chr16: 20709861-20709887 | intron | ENST00000501740 | ACSM3 |

| Sequence (SEQ ID NO:) | HLA allele | Percentile Rank | Nucleotide sequence (SEQ ID NO:) | Tumor Sample |
|---|---|---|---|---|
| NEQTTILY (1) | HLA-A*01:01 | 1.94 | AATGAACAGACTACCATTTTGTAC (93) | 11H099 |
| ALFSNEVSL (2) | HLA-A*02:01 | 0.3 | GCACTTTTTAGCAATGAAGTGTCTTTG (94) | 10H080 |
| FIPDLFTEL(3) | HLA-A*02:01 | 0.25 | TTCATCCCAGATCTATTTACAGAATTA (95) | 10H080 |
| FLLDHILTI (4) | HLA-A*02:01 | 0.001 | TTTCTTTTGGATCACATATTGACCATT (96) | 05H129 |
| FLLESRETL (5) | HLA-A*02:01 | 0.023 | TTCCTATTGGAGTCCAGGGAAACTTTA (97) | 17H112 |
| FLLPTSLSL (6) | HLA-A*02:01 | 0.03 | TTCTTGCTTCCAACTTCACTTTCTTTG (98) | 10H080 |

TABLE 1-continued

| Features of the aeTSA identified in the studies described herein | | | | |
|---|---|---|---|---|
| FLLSDELLL (7) | HLA-A*02:01 | 0.026 | TTTCTTCTCTCTGATGAACTTCTTTTA (99) | 17H017 |
| GLATAVWLL (8) | HLA-A*02:01 | 0.08 | GGGCTGGCCACAGCCGTGTGGCTGCTC (100) | 10H080 |
| GLLTASIFL (9) | HLA-A*02:01 | 0.115 | GGATTATTAACGGCATCCATTTTCTTG (101) | 17H112 |
| GTLCLLTFI (10) | HLA-A*02:01 | 1.5 | GGTACCTTGTGCCTATTAACTTTCATT (102) | 10H080 |
| KLLQPLPIT (11) | HLA-A*02:01 | 0.822 | AAACTCCTCCAACCTCTGCCCATTACC (103) | 17H112 |
| LLQNLIVLL(12) | HLA-A*02:01 | 0.6 | CTTCTTCAAAATTTAATAGTGCTGTTA (104) | 10H080 |
| LLSLYLVSI (13) | HLA-A*02:01 | 0.4 | CTCTTAAGTTTGTATTTAGTAAGTATA (105) | 10H080 |
| LMLLFVVLL (14) | HLA-A*02:01 | 1.755 | TTAATGTTACTCTTTGTCGTATTACTA (106) | 08H028 |
| SLANETHTL (15) | HLA-A*02:01 | 0.033 | TCTTTGGCCAACGAGACCCACACCCTT (107) | 16H116 |
| VLLDFPALL (16) | HLA-A*02:01 | 0.025 | GTACTGTTGGACTTTCCGGCTCTGTTA (108) | 16H116 |
| VLLSKILYP (17) | HLA-A*02:01 | 1.666 | GTTTTACTTTCAAAAATACTATATCCA (109) | 17H017 |
| WLVEKLSGV (18) | HLA-A*02:01 | 0.086 | TGGTTGGTGGAGAAGCTCAGTGGTGTG (110) | 17H017 |
| YLFAHSIIL (19) | HLA-A*02:01 | 0.03 | TACTTGTTTGCACATTCCATTATCTTA (111) | 16H133 |
| YLGYAVAV (20) | HLA-A*02:01 | 1.305 | TACCTGGGTTACGCTGTGGCCGTG (112) | 16H116 |
| YLQEISLRL (21) | HLA-A*02:01 | 0.005 | TATCTGCAAGAAATATCATTAAGATTA (113) | 17H112 |
| SLLGIGLLA (22) | HLA-A*02:01 | 1.2 | AGTCTTTTAGGAATAGGATTGTTGGCA (114) | 10H080 |
| AAMESPIQSK (23) | HLA-A*11:01 | 0.014 | GCAGCCATGGAGTCTCCTATACAGTCCAAG (115) | 14H148 |
| ALFGFVGFPNK (24) | HLA-A*11:01 | 0.399 | GCCCTATTTGGTTTTGTTGGATTCCCCAACAAG (116) | 17H112 |
| ALFVLTSIK (25) | HLA-A*11:01 | 0.441 | GCACTGTTTGTGTTAACATCAATAAAA (117) | 14H148 |
| ATSLTIQEK (26) | HLA-A*11:01 | 0.014 | GCTACAAGTCTCACCATCCAGGAAAAA (118) | 17H112 |
| AVAVPLLPR (27) | HLA-A*11:01 | 0.053 | GCTGTAGCAGTTCCCCTCCTGCCTAGG (119) | 17H112 |
| GTISGGFFK (28) | HLA-A*11:01 | 0.006 | GGAACTATATCAGGTGGCTTCTTCAAA (120) | 17H112 |
| GVANSLLK (29) | HLA-A*11:01 | 1.6 | GGTGTGGCCAATAGTCTTTTAAAA (121) | 10H080 |
| GVSPVLFLK (30) | HLA-A*11:01 | 0.01 | GGCGTCTCTCCTGTGTTATTTCTAAAG (122) | 10H080 |
| LLGLPQPPK (31) | HLA-A*11:01 | 0.76 | CTTCTGGGCTTGCCTCAGCCTCCTAAA (123) | 17H112 |
| LSSRLPLGK (32) | HLA-A*11:01 | 0.4 | CTGTCTTCAAGACTGCCACTGGGGAAG (124) | 10H080 |
| NLLFSRVFK (33) | HLA-A*11:01 | 0.513 | AACCTTCTGTTTAGTAGAGTTTTTAAG (125) | 17H112 |
| STGVLTVLK (34) | HLA-A*11:01 | 0.029 | TCAACTGGAGTCCTCACTGTGCTAAAG (126) | 14H148 |
| SVFDRTNNR (35) | HLA-A*11:01 | 0.037 | AGTGTCTTTGACAGGACCAATAACCGT (127) | 14H148 |
| SVVPHPLQK (36) | HLA-A*11:01 | 0.001 | TCAGTAGTGCCTCATCCCCTTCAAAAG (128) | 14H148 |
| TTSSIYIRK (37) | HLA-A*11:01 | 0.007 | ACAACCAGTTCAATCTACATAAGAAAG (129) | 16H133 |
| LYTFIKHEF (38) | HLA-A*24:02 | 0.012 | TTGTACACATTTATAAAACATGAATTC (130) | 14H025 |
| SYFDPSYSNF (39) | HLA-A*24:02 | 0.008 | TCCTACTTTGATCCTTCGTACAGCAATTTT (131) | 05H080_ 14H025 |
| SYLASFLLY (40) | HLA-A*24:02 | 0.228 | TCATACCTGGCATCTTTCTTGTTGTAC (132) | 05H175 |
| VYSPSPLNF (41) | HLA-A*24:02 | 0.001 | GTATATTCTCCAAGCCCATTGAATTTC (133) | 14H025 |
| VYTQVSAF (42) | HLA-A*24:02 | 0.348 | GTGTACACGCAGGTGTCCGCCTTT (134) | 10H013 |
| YSVLTVTF (43) | HLA-A*24:02 | 0.518 | TATTCTGTTCTAACAGTAACTTTT (135) | 14H025 |
| NLGLFLSY (44) | HLA-A*29:02 | 1.223 | AATCTGGGGCTTTTTCTCTCATAC (136) | 17H017 |
| AVGGFRSSW (45) | HLA-A*32:01 | 0.03 | GCCGTGGGAGGCTTCAGGAGCAGCTGG (137) | 15H042_ 14H025 |

TABLE 1-continued

| Features of the aeTSA identified in the studies described herein | | | | |
|---|---|---|---|---|
| SQVQAVLLAW (46) | HLA-A*32:01 | 0.356 | TCACAGGTTCAAGCAGTTCTCCTAGCTTGG (138) | 14H025 |
| QTNSGSLAR (47) | HLA-A*66:01 | 0.123 | CAGACAAACAGTGGATCTCTCGCCAGA (139) | 10H013 |
| DVAGVGMPK (48) | HLA-A*68:01 | 0.054 | GACGTGGCAGGAGTTGGCATGCCCAAG (140) | 05H080 |
| DVMASLARV (49) | HLA-A*68:02 | 0.02 | GATGTGATGGCCTCCCTCGCCAGAGTC (141) | 16H116 |
| EVGAVFAVL (50) | HLA-A*68:02 | 0.151 | GAAGTGGGAGCCGTGTTTGCTGTCTTA (142) | 16H116_ 13H051 |
| VVADILLSV (51) | HLA-A*68:02 | 0.014 | GTGGTTGCCGACATCCTGCTGTCTGTG (143) | 16H116 |
| SSLSGPVSSL (52) | HLA-B*07:02 | 1.838 | TCATCTCTGAGTGGTCCAGTGAGCTCGCTG (144) | 15H042 |
| AFRVIVAL (53) | HLA-B*08:01 | 1.451 | GCCTTTAGGGTTATTGTTGCTTTA (145) | 17H112 |
| EHYNKVVVM (54) | HLA-B*14:02 | 0.003 | GAACACTACAATAAAGTAGTGGTAATG (146) | 13H051 |
| VQAQVLEAI (55) | HLA-B*15:10 | 1.145 | GTGCAAGCCCAGGTTTTAGAAGCCATC (147) | 13H051 |
| NNMAIIYSY (56) | HLA-B*18:01 | 0.269 | AACAATATGGCAATAATCTATTCTTAT (148) | 05H148 |
| EPSHSINVY (57) | HLA-B*35:01 | 0.033 | GAGCOATCCCATTOAATAAATGTTTAT (149) | 11H099 |
| IPVGSGLGYVL (58) | HLA-B*35:01 | 0.945 | ATCCCCGTTGGAAGTGGTCTGGGCTACGTGCTG (150) | 11H099 |
| DHDIGVYSV (59) | HLA-B*39:01 | 0.016 | GACCATGACATCGGTGTGTACAGCGTC (151) | 17H017 |
| HFEWQPPL (60) | HLA-B*39:01 | 0.923 | CACTTTGAGTGGCAGCCACCTCTG (152) | 17H017 |
| GEFLVPLSL (61) | HLA-B*40:01 | 0.012 | GGGGAGTTCCTTGTTCCTCTGTCCCTC (153) | 08H125 |
| GEVDGAQQAM (62) | HLA-B*40:01 | 0.2 | GGTGAAGTGGATGGGGCACAGCAGGCAATG (154) | 10H080 |
| IEEVSQGLL (63) | HLA-B*40:01 | 0.26 | ATAGAGGAGGTGAGCCAGGGGCTGCTC (155) | 08H125 |
| IESEDFGFWSL (64) | HLA-B*40:01 | 0.5 | ATAGAGTCAGAAGACTTTGGATTTTGGAGTCTG (156) | 10H080 |
| LENSGFILI (65) | HLA-B*40:01 | 0.15 | CTGGAGAATAGTGGATTTATATTAATA (157) | 10H080 |
| REPLEILITL (66) | HLA-B*40:01 | 0.12 | AGAGAACCATTGGAGATACTCATTACTCTT (158) | 10H080 |
| EETDAYKSL (67) | HLA-B*44:02 | 0.112 | GAAGAGACAGATGCCTACAAAAGCCTC (159) | 16H116 |
| SELQLPVTF (68) | HLA-B*44:02 | 0.009 | AGTGAATTACAACTACCTGTTACTTTC (160) | 05H129 |
| QEIATSHNI (69) | HLA-B*49:01 | 0.012 | CAGGAGATAGCAACAAGCCATAATATA (161) | 14H025 |
| AQFLLFIA (70) | HLA-B*50:01 | 1.912 | GCCCAATTCCTTCTCTTTATTGCA (162) | 17H112 |
| FEISSVTTA (71) | HLA-B*50:01 | 0.007 | TTTGAAATCAGCTCTGTAACCACAGCC (163) | 17H112_ 14H025 |
| KEVGGLRSA (72) | HLA-B*50:01 | 0.007 | AAAGAGGTGGGTGGGCTTAGGTCAGCT (164) | 14H025 |
| TEFGPVIG (73) | HLA-B*50:01 | 1.67 | ACTGAGTTTGGTCCTGTCATTGGG (165) | 14H025 |
| ISLPALEVL (74) | HLA-0*01:02 | 0.603 | ATATCCCTTCCTGCTCTAGAGGTTCTG (166) | 17H017 |
| LPSPPLPPSL (75) | HLA-0*01:02 | 0.147 | CTCCCCTCCCCTCCCCTTCCTCCCTCCCTC (167) | 17H017 |
| LYLPSVVLI (76) | HLA-0*01:02 | 1.886 | TTATATTTGCCCTCTGTTGTGCTGATC (168) | 17H017 |
| RPPAPLLPVL (77) | HLA-0*01:02 | 0.525 | CGGCCACCAGCTCCTCTGCTCCCTGTCCTT (169) | 16H133 |
| SLHYSVSL (78) | HLA-0*01:02 | 1.051 | TCACTGCACTACTCTGTCTCTTTA (170) | 17H017 |
| SLPDHQGVL (79) | HLA-0*01:02 | 0.01 | AGTCTCCCAGATCACCAGGGTGTCTTA (171) | 17H017 |
| EAVSQGKDF (80) | HLA-0*02:02 | 1.779 | GAGGCAGTTTCCCAGGGGAAGGATTTT (172) | 16H116 |
| YSSYLSIHY (81) | HLA-0*02:02 | 0.052 | TATTCTAGTTATTTAAGCATTCATTAT (173) | 08H125 |
| ASLGLSLAL (82) | HLA-0*03:04 | 0.331 | GCCTCACTGGGCTTAAGCTTGGCTTTG (174) | 08H125 |
| LCHRTPPSL (83) | HLA-0*03:04 | 1.511 | TTGTGCCACCGCACTCCACCCAGCCTG (175) | 13H051 |
| LSISPFQAI (84) | HLA-0*03:04 | 0.207 | TTATCTATTTCTCCTTTTCAGGCTATC (176) | 13H051 |

TABLE 1-continued

| Features of the aeTSA identified in the studies described herein | | | | |
|---|---|---|---|---|
| GWGGSPLYL (85) | HLA-0*04:01 | 0.879 | GGGTGGGGAGGGAGTCCTTTGTACCTA (177) | 11H099 |
| YFDPSYSNF (86) | HLA-0*04:01 | 0.001 | TACTTTGATCCTTCGTACAGCAATTTT (178) | 08H028_14H148 |
| ISLSSIVSV (87) | HLA-0*15:02 | 0.038 | ATTTCTCTCTCTTCTATAGTTTCTGTA (179) | 16H133 |
| LSISSLVSV (88) | HLA-0*15:02 | 0.097 | TTATCTATTTCTTCTCTTGTGAGTGTT (180) | 16H133 |
| SLTALVFHV (89) | HLA-A*02:01 | 0.06 | TCCCTCACAGCACTAGTATTTCATGTT (181) | 10H080 |
| RIFGFRLWK (90) | HLA-A*11:01 | 0.01 | AGGATTTTTGGCTTTCGGCTCTGGAAA (182) | 10H080 |
| TSFAETWMK (91) | HLA-A*11:01 | 0.01 | ACATCCTTTGCAGAGACATGGATGAAA (183) | 10H080 |
| IPLNPFSSL (92) | HLA-B*35:01 | 0.172 | ATACCTTTGAATCCTTTCAGTTCTTTG (184) | 11H099 |

Figure 4B:
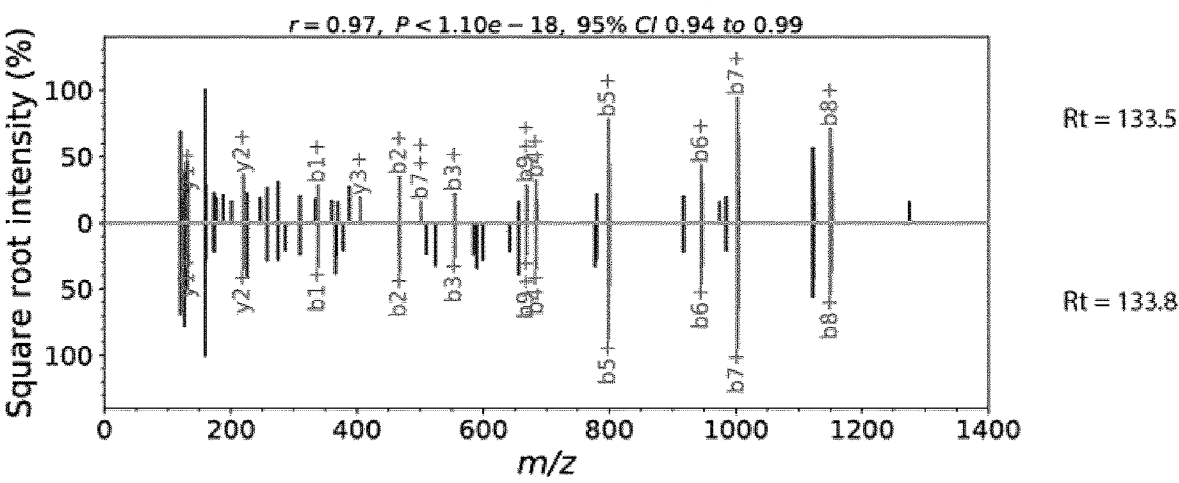
FIG. 4B shows a mirror plot of IESEDFGFWSL for TMT-labeled endogenous TSA (bottom) and its corresponding synthetic peptides (top). Retention time and Pearson correlation coefficient are shown.
Figure 10J:
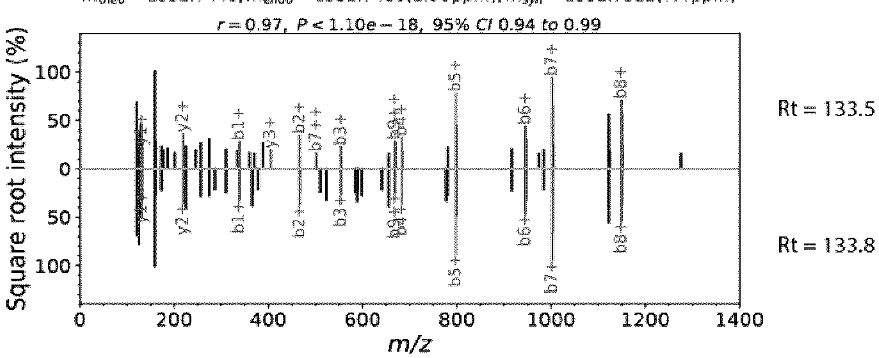
FIGS. 10A-V show mirror plots of all TMT-labeled aeTSA peptides identified from 10H080 sample and their synthetic counterparts.
Figure 10K:
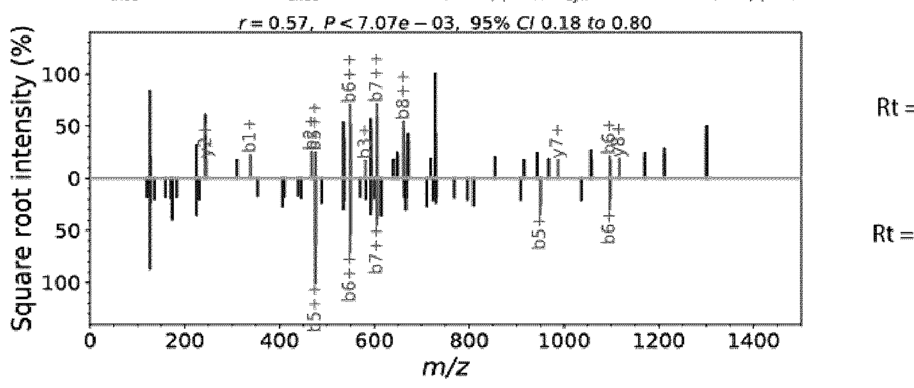
Figure 10L:
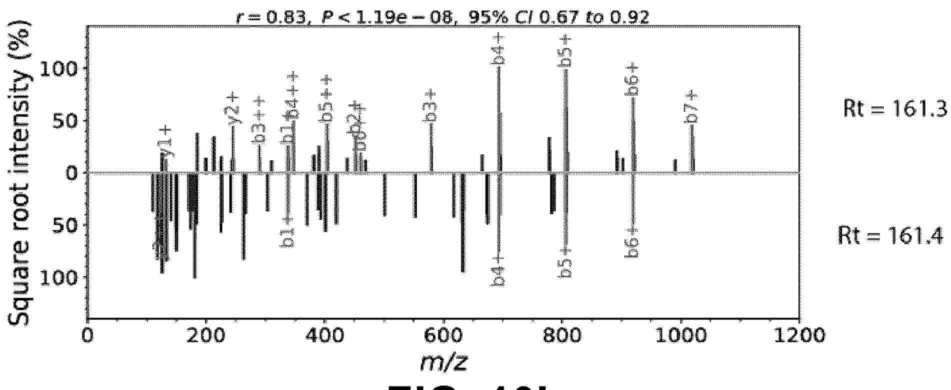
Figure 10P:
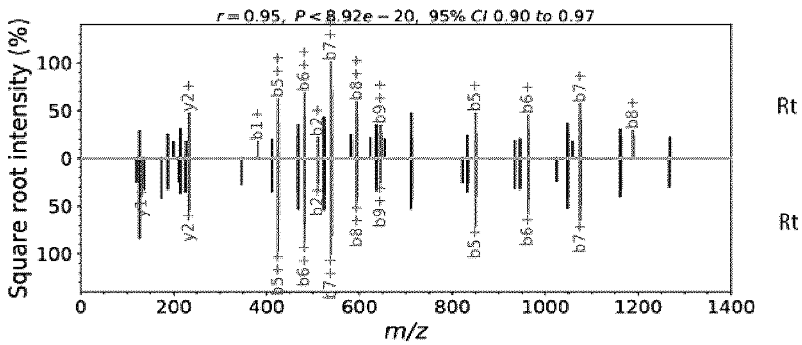
Figure 10Q:
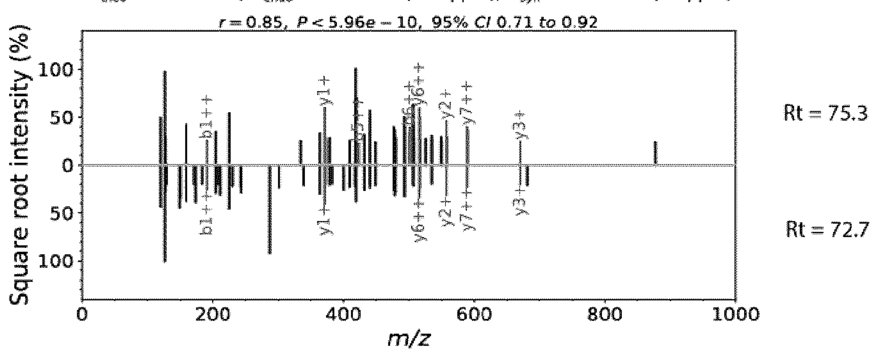
Figure 10R:
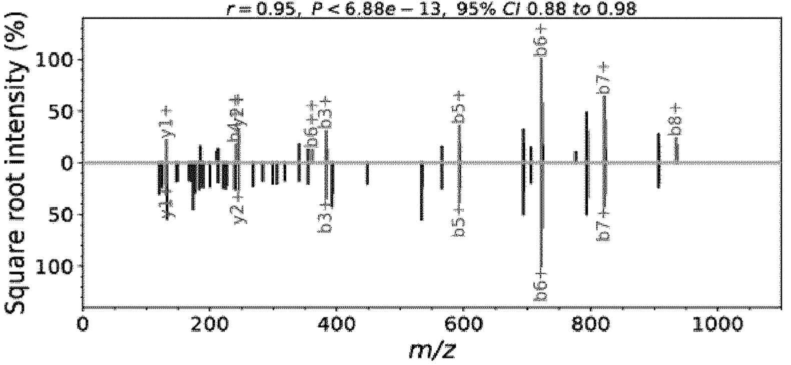
Figure 10V:
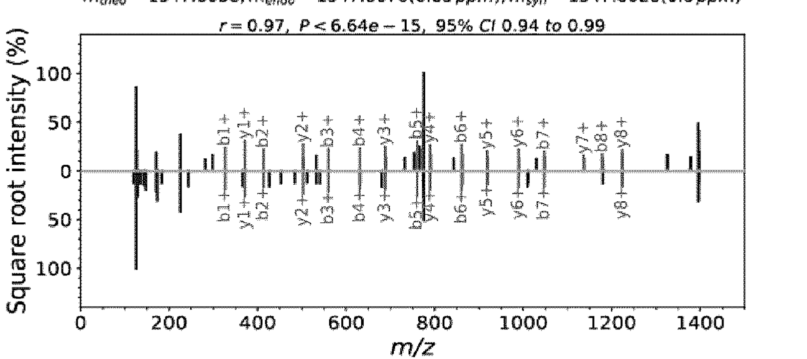

TSA candidates identified from 10H080 sample (SEQ ID NO: 2, 3, 6, 8, 10, 13, 14, 22, 29, 30, 32, 62, 64, 65 and 66) were validated with their corresponding synthetic peptides (FIGS. 10A-10*y*). An example is shown in FIG. 4B where the MS/MS spectra of the TMT-labeled peptide IESEDFGFWSL obtained from the endogenous B-ALL sample and its synthetic counterpart was compared. Validation of TSA candidates relied on the correlation of fragment ions and retention time between native and synthetic peptides. MS/MS spectra were correlated with Pearson coefficient >0.75 and retention time of synthetic peptides was within +/−2 min of their native counterparts. The genomic location of each aeTSA was identified and the corresponding transcripts were confirmed to be expressed only in the B-ALL sample. All TSAs identified here derived from non-mutated yet aberrantly expressed transcripts that could be shared by multiple leukemic specimens. This, in addition to the low expression of TSA transcripts across a panel of human tissues, and mTECs make them attractive candidates for leukemia vaccine development.

Example 4: Determination of Antigen Expression Using Isobaric Peptide Labeling

The prioritization of antigens for TSA immunization or for optimal graft versus tumor effects using MiHAs partly relies on the abundance of the corresponding antigens. While the antigen discovery approach described herein typically uses shotgun mass spectrometry, the limited dynamic range of peptide identification may preferentially select the most abundant antigens, and can underestimate the extent of antigens shared across different patients. To determine the expression of antigens presented at the cell surface by MHC I molecules, the capability of targeted LC-MS/MS assays was evaluated using isobaric peptide labeling. Accordingly, 27 MiHAs previously identified in B-lymphoblastoid cells from a cohort of 13 subjects where the corresponding peptides were found to share optimal features for immunotherapy of hematologic cancers were selected[38]. The B-LCL cells described in the previous section were obtained from a different subject and shared alleles A*02:01 and B*44:03 though only 9 of the 27 optimal MiHAs were identified in the samples upon TMT labeling. It is noteworthy that all transcripts of the corresponding genes were expressed in the selected B-LCL cells. It was surmised that several of the undetected MiHAs from the B-LCL cells could be identified and quantified using targeted LC-MS/MS analyses. To determine the abundance of MiHAs presented by MHC I molecules, LC-MS/MS with synchronous precursor selection (SPS)[40] was performed, quantitative measurements were compared with those obtained using LC-MS/MS with and without FAIMS.

Figure 5A:
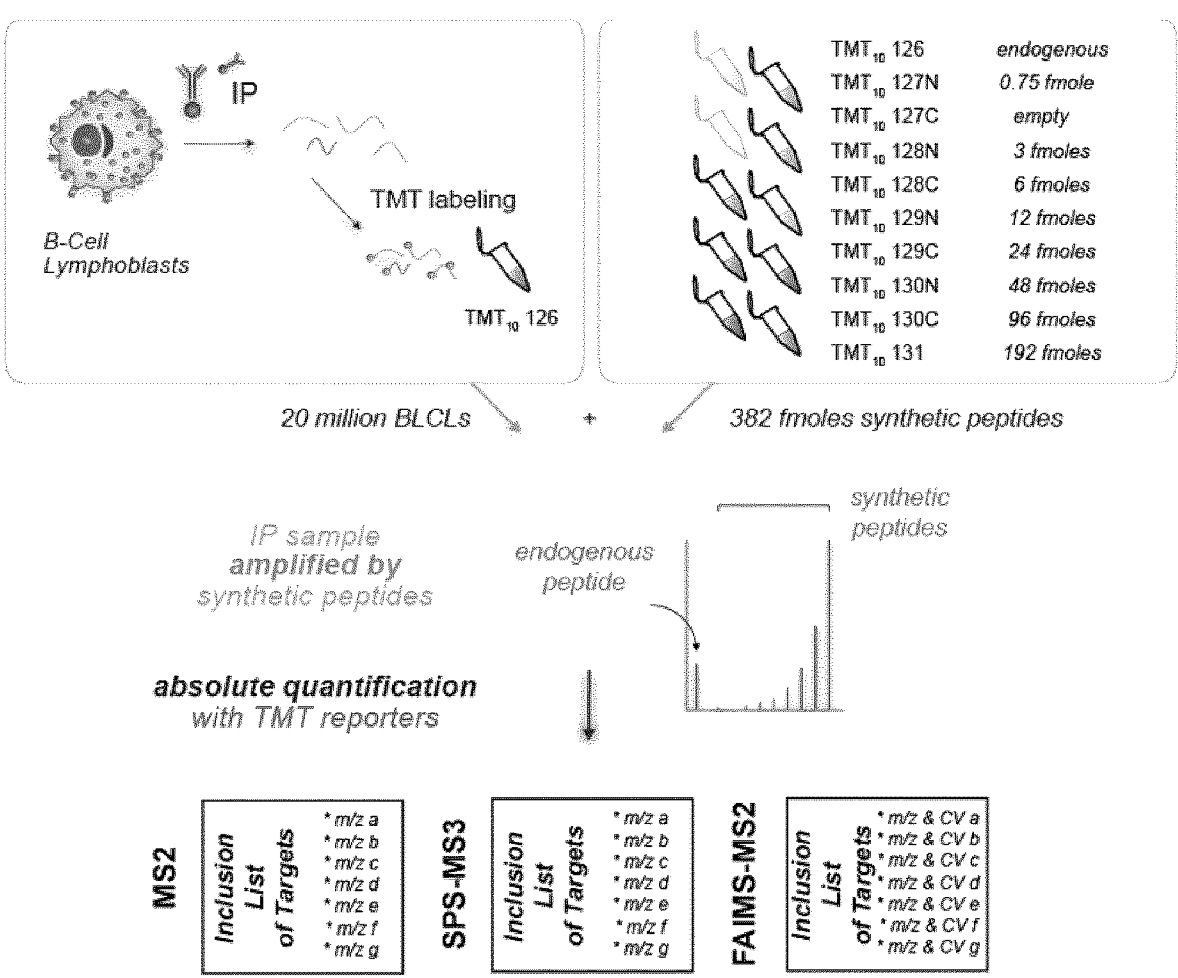
FIG. 5A depicts an experimental workflow showing the TMT labeling scheme for the endogenous MHC I peptides (TMT-126) and the synthetic peptides of increasing amounts (TMT127C-TMT131). Note that TMT 127C is left empty to determine the extent of interfering ions. Samples are analyzed in triplicates using LC-MS/MS with SPS, FAIMS, and MS2 only.

Immunopurified MHC I peptide extracts from 20 million B-LCL cells were labeled with TMT-126 while synthetic peptides of different amounts ranging from 0.75 to 192 fmoles were labeled with TMT-127 to TMT-131 (FIG. 5A). The TMT-127C channel was left empty to determine the extent of interfering ions. Triplicate LC-MS/MS analyses with and without FAIMS were performed on the corresponding peptide extracts, precursor ion tolerance was set to 5 ppm, and only MS/MS spectra acquired within ±30 s of the expected retention time of each MiHA peptide were considered for quantitative measurements. To minimize the contribution of interfering signals, only MS-MS spectra where no signal was detected in the TMT-127C channel or when the intensity of the endogenous peptide ion (TMT-126) was above that of the TMT-128C were selected. For absolute quantification, the occurrence of at least 7 consecutive reporter ions with a linear correlation coefficient, $r \geq 0.9$, was relied upon. In total, 25 of the 27 MiHAs selected were quantified, the remaining 2 MiHAs were below the limit of quantification. The abundance of endogenous MiHAs obtained from all three LC-MS/MS approaches ranged from 2.3 to 18.6 fmoles. From these analyses, it was estimated that MiHA expression varied from 70 to 560 molecules/cell assuming quantitative peptide recoveries from immunoaffinity purification (FIG. 5B). Each method provided reproducible measurements with relative standard deviation (RSD) ranging from 24-34%, on average. It was noted that MiHA expression levels determined by LC-MS/MS and SPS were comparable to those achieved when using FAIMS, and measurements were typically within 18% of each other. However, when comparing SPS with LC-MS/MS, larger variations with values overestimated by 31%, on average, were found. This overestimation is associated with the co-selection of precursor ions in LC-MS/MS.

Although the present invention has been described hereinabove by way of specific embodiments thereof, it can be modified, without departing from the spirit and nature of the subject invention as defined in the appended claims. In the claims, the word “comprising” is used as an open-ended term, substantially equivalent to the phrase “including, but not limited to”. The singular forms “a”, “an” and “the” include corresponding plural references unless the context clearly dictates otherwise.

REFERENCES (1) Murata, S.; Takahama, Y.; Kasahara, M.; Tanaka, K. Nat Immunol 2018, 19, 923-931.

(2) Davis, M. M.; Krogsgaard, M.; Huse, M.; Huppa, J.; Lillemeier, B. F.; Li, Q. J. Annu Rev Immunol 2007, 25, 681-695.

(3) Neefjes, J.; Jongsma, M. L.; Paul, P.; Bakke, O. Nat Rev Immunol 2011, 11, 823-836.

(4) Roche, P. A.; Furuta, K. Nat Rev Immunol 2015, 15, 203-216.

(5) Blum, J. S.; Wearsch, P. A.; Cresswell, P. Annu Rev Immunol 2013, 31, 443-473.

(6) Rock, K. L.; Reits, E.; Neefjes, J. Trends Immunol 2016, 37, 724-737.

(7) Hoare, H. L.; Sullivan, L. C.; Pietra, G.; Clements, C. S.; Lee, E. J.; Ely, L. K.; Beddoe, T.; Falco, M.; Kjer-Nielsen, L.; Reid, H. H.; McCluskey, J.; Moretta, L.; Rossjohn, J.; Brooks, A. G. Nat Immunol 2006, 7, 256-264.

(8) Robinson, J.; Guethlein, L. A.; Cereb, N.; Yang, S. Y.; Norman, P. J.; Marsh, S. G. E.; Parham, P. PLoS Genet 2017, 13, e1006862.

(9) Robinson, J.; Halliwell, J. A.; Hayhurst, J. D.; Flicek, P.; Parham, P.; Marsh, S. G. Nucleic Acids Res 2015, 43, D423-431.

(10) Weinzierl, A. O.; Lemmel, C.; Schoor, O.; Muller, M.; Kruger, T.; Wernet, D.; Hennenlotter, J.; Stenzl, A.; Klingel, K.; Rammensee, H. G.; Stevanovic, S. Mol Cell Proteomics 2007, 6, 102-113.

(11) Lanoix, J.; Durette, C.; Courcelles, M.; Cossette, E.; Comtois-Marotte, S.; Hardy, M. P.; Cote, C.; Perreault, C.; Thibault, P. Proteomics 2018, 18, e1700251.

(12) Bassani-Sternberg, M.; Braunlein, E.; Klar, R.; Engleitner, T.; Sinitcyn, P.; Audehm, S.; Straub, M.; Weber, J.; Slotta-Huspenina, J.; Specht, K.; Martignoni, M. E.; Werner, A.; Hein, R.; D, H. B.; Peschel, C.; Rad, R.; Cox, J.; Mann, M.; Krackhardt, A. M. Nat Commun 2016, 7, 13404.

(13) Bilich, T.; Nelde, A.; Bichmann, L.; Roerden, M.; Salih, H. R.; Kowalewski, D. J.; Schuster, H.; Tsou, C. C.; Marcu, A.; Neidert, M. C.; Lubke, M.; Rieth, J.; Schemionek, M.; Brummendorf, T. H.; Vucinic, V.; Niederwieser, D.; Bauer, J.; Marklin, M.; Peper, J. K.; Klein, R., et al. Blood 2019, 133, 550-565.

(14) Caron, E.; Kowalewski, D. J.; Chiek Koh, C.; Sturm, T.; Schuster, H.; Aebersold, R. Mol Cell Proteomics 2015, 14, 3105-3117.

(15) Shraibman, B.; Barnea, E.; Kadosh, D. M.; Haimovich, Y.; Slobodin, G.; Rosner, I.; Lopez-Larrea, C.; Hilf, N.; Kuttruff, S.; Song, C.; Britten, C.; Castle, J.; Kreiter, S.; Frenzel, K.; Tatagiba, M.; Tabatabai, G.; Dietrich, P. Y.; Dutoit, V.; Wick, W.; Platten, M., et al. Mol Cell Proteomics 2018, 17, 2132-2145.

(16) Mommen, G. P.; Frese, C. K.; Meiring, H. D.; van Gaans-van den Brink, J.; de Jong, A. P.; van Els, C. A.; Heck, A. J. Proc Natl Acad Sci USA 2014, 111, 4507-4512.

(17) Murphy, J. P.; Konda, P.; Kowalewski, D. J.; Schuster, H.; Clements, D.; Kim, Y.; Cohen, A. M.; Sharif, T.; Nielsen, M.; Stevanovic, S.; Lee, P. W.; Gujar, S. J Proteome Res 2017, 16, 1806-1816.

(18) Granados, D. P.; Yahyaoui, W.; Laumont, C. M.; Daouda, T.; Muratore-Schroeder, T. L.; Cote, C.; Laverdure, J. P.; Lemieux, S.; Thibault, P.; Perreault, C. Blood 2012, 119, e181-191.

(19) Liepe, J.; Marino, F.; Sidney, J.; Jeko, A.; Bunting, D. E.; Sette, A.; Kloetzel, P. M.; Stumpf, M. P.; Heck, A. J.; Mishto, M. Science 2016, 354, 354-358.

(20) Laumont, C. M.; Perreault, C. Cell Mol Life Sci 2018, 75, 607-621.

(21) Granados, D. P.; Laumont, C. M.; Thibault, P.; Perreault, C. Curr Opin Immunol 2015, 34, 1-8.

(22) Roopenian, D.; Choi, E. Y.; Brown, A. Immunol Rev 2002, 190, 86-94.

(23) Spierings, E.; Hendriks, M.; Absi, L.; Canossi, A.; Chhaya, S.; Crowley, J.; Dolstra, H.; Eliaou, J. F.; Ellis, T.; Enczmann, J.; Fasano, M. E.; Gervais, T.; Gorodezky, C.; Kircher, B.; Laurin, D.; Leffell, M. S.; Loiseau, P.; Malkki, M.; Markiewicz, M.; Martinetti, M., et al. PLoS Genet 2007, 3, e103.

(24) Murphy, J. P.; Yu, Q.; Konda, P.; Paulo, J. A.; Jedrychowski, M. P.; Kowalewski, D. J.; Schuster, H.; Kim, Y.; Clements, D.; Jain, A.; Stevanovic, S.; Gygi, S. P.; Mancias, J. D.; Gujar, S. Anal Chem 2019, 91, 5106-5115.

(25) Pfammatter, S.; Bonneil, E.; McManus, F. P.; Prasad, S.; Bailey, D. J.; Belford, M.; Dunyach, J. J.; Thibault, P. Mol Cell Proteomics 2018, 17, 2051-2067.

(26) Pfammatter, S.; Bonneil, E.; Thibault, P. J Proteome Res 2016, 15, 4653-4665.

(27) Granados, D. P.; Sriranganadane, D.; Daouda, T.; Zieger, A.; Laumont, C. M.; Caron-Lizotte, O.; Boucher, G.; Hardy, M. P.; Gendron, P.; Cote, C.; Lemieux, S.; Thibault, P.; Perreault, C. Nat Commun 2014, 5, 3600.

(28) Zecha, J.; Satpathy, S.; Kanashova, T.; Avanessian, S. C.; Kane, M. H.; Clauser, K. R.; Mertins, P.; Carr, S. A.; Kuster, B. Mol Cell Proteomics 2019, 18, 1468-1478.

(29) Courcelles, M.; Durette, C.; Daouda, T.; Laverdure, J. P.; Vincent, K.; Lemieux, S.; Perreault, C.; Thibault, P. J Proteome Res 2020.

(30) Hunt, S. E.; McLaren, W.; Gil, L.; Thormann, A.; Schuilenburg, H.; Sheppard, D.; Parton, A.; Armean, I. M.; Trevanion, S. J.; Flicek, P.; Cunningham, F. Database (Oxford) 2018, 2018.

(31) Laumont, C. M.; Vincent, K.; Hesnard, L.; Audemard, E.; Bonneil, E.; Laverdure, J. P.; Gendron, P.; Courcelles, M.; Hardy, M. P.; Cote, C.; Durette, C.; St-Pierre, C.; Benhammadi, M.; Lanoix, J.; Vobecky, S.; Haddad, E.; Lemieux, S.; Thibault, P.; Perreault, C. Sci Transl Med 2018, 10.

(32) Pearson, H.; Daouda, T.; Granados, D. P.; Durette, C.; Bonneil, E.; Courcelles, M.; Rodenbrock, A.; Laverdure, J. P.; Cote, C.; Mader, S.; Lemieux, S.; Thibault, P.; Perreault, C. J Clin Invest 2016, 126, 4690-4701.

(33) Garrison, E.; Marth, G. arXiv e-prints 2012.

(34) Bray, N. L.; Pimentel, H.; Melsted, P.; Pachter, L. Nat Biotechnol 2016, 34, 525-527.

(35) Thompson, A.; Schafer, J.; Kuhn, K.; Kienle, S.; Schwarz, J.; Schmidt, G.; Neumann, T.; Johnstone, R.; Mohammed, A. K.; Hamon, C. Anal Chem 2003, 75, 1895-1904.

(36) Tsai, C. F.; Smith, J. S.; Krajewski, K.; Zhao, R.; Moghieb, A. M.; Nicora, C. D.; Xiong, X.; Moore, R. J.; Liu, T.; Smith, R. D.; Jacobs, J. M.; Rajagopal, S.; Shi, T. Anal Chem 2019, 91, 11606-11613.

(37) Genomes Project, C.; Abecasis, G. R.; Altshuler, D.; Auton, A.; Brooks, L. D.; Durbin, R. M.; Gibbs, R. A.; Hurles, M. E.; McVean, G. A. Nature 2010, 467, 1061-1073.

(38) Granados, D. P.; Rodenbrock, A.; Laverdure, J. P.; Cote, C.; Caron-Lizotte, O.; Carli, C.; Pearson, H.; Janelle, V.;

Durette, C.; Bonneil, E.; Roy, D. C.; Delisle, J. S.; Lemieux, S.; Thibault, P.; Perreault, C. Leukemia 2016, 30, 1344-1354.

(39) Ehx, G.; Perreault, C. Genome Med 2019, 11, 29.

(40) McAlister, G. C.; Nusinow, D. P.; Jedrychowski, M. P.; Wuhr, M.; Huttlin, E. L.; Erickson, B. K.; Rad, R.; Haas, W.; Gygi, S. P. Anal Chem 2014, 86, 7150-7158.

(41) Perez-Riverol, Y.; Csordas, A.; Bai, J.; Bernal-Llinares, M.; Hewapathirana, S.; Kundu, D. J.; Inuganti, A.; Griss, J.; Mayer, G.; Eisenacher, M.; Perez, E.; Uszkoreit, J.; Pfeuffer, J.; Sachsenberg, T.; Yilmaz, S.; Tiwary, S.; Cox, J.; Audain, E.; Walzer, M.; Jarnuczak, A. F., et al. Nucleic Acids Res 2019, 47, D442-D450.

(42) Ehx G, Larouche J D, Durette C, Laverdure J P, Hesnard L, Vincent K, Hardy M P, Thériault C, Rulleau C, Lanoix J, Bonneil E, Feghaly A, Apavaloaei A, Noronha N, Laumont C M, Delisle J S, Vago L, Hébert J, Sauvageau G, Lemieux S, Thibault P, Perreault C. Immunity. 2021, 54, Epub ahead of print.

(43) Martin Thomsen, Claus Lundegaard, Søren Buus, Ole Lund, and Morten Nielsen. Immunogenetics. 2013 September; 65(9): 655-665.

(44) Douglass et al., *Sci. Immunol.* 6, eabd5515 (2021) 1 Mar. 2021;

(45) Hsiue et al., *Science*. 2021 Mar. 5; 371(6533): eabc8697. Epub 2021 Mar. 1.

(46) Yang et al., *Theranostics* 2019, Vol. 9, Issue 25: 7792-7806.

What is claimed is:

1. A method of stimulating a T cell response against lymphoblastic leukemia in a subject comprising administering to the subject an effective amount of:

(i) a leukemia tumor antigen peptide (TAP) comprising the amino acid sequence of SEQ ID NO:4; or a nucleic acid encoding said TAP;

(ii) a combination comprising of the leukemia TAP or nucleic acid defined in (i), and at least one additional leukemia TAP or nucleic acid encoding the at least one additional leukemia TAP, wherein the at least one additional leukemia TAP comprises one of the amino acid sequences set forth in SEQ ID NOs: 1-3, 5-88 and 92;

(iii) a vehicle comprising the leukemia TAP or nucleic acid defined in (i), or the combination defined in (ii);

(iv) a composition comprising the leukemia TAP or nucleic acid defined in (i), the combination defined in (ii); or the vehicle defined in (iii); or (v) a vaccine comprising the leukemia TAP or nucleic acid defined in (i), the combination defined in (ii); the vehicle defined in (iii) or the composition defined in (iv); and an adjuvant.

2. The method of claim 1, wherein said lymphoblastic leukemia is acute lymphoblastic leukemia (ALL).

3. The method of claim 2, wherein the ALL is B-ALL.

4. The method of claim 1, further comprising administering at least one additional antitumor agent or therapy to the subject.

5. The method of claim 4, wherein said at least one additional antitumor agent or therapy is a chemotherapeutic agent, immunotherapy, an immune checkpoint inhibitor, radiotherapy or surgery.

6. The method of claim 1, wherein the leukemia TAP consists of the amino acid sequence of SEQ ID NO:4.

7. The method of claim 1, wherein the method comprises administering to the subject an effective amount of (a) an mRNA molecule encoding the leukemia TAP, or (b) a vehicle, composition or vaccine comprising the mRNA molecule.

8. The method of claim 6, wherein the method comprises administering to the subject an effective amount of (a) an mRNA molecule encoding the leukemia TAP, or (b) a vehicle, composition or vaccine comprising the mRNA molecule.

9. The method of claim 7, wherein the method further comprises administering to the subject an effective amount of an immune checkpoint inhibitor.

10. The method of claim 8, wherein the method further comprises administering to the subject an effective amount of an immune checkpoint inhibitor.

11. The method of claim 7, wherein the lymphoblastic leukemia is B-cell acute lymphoblastic leukemia (B-ALL).

12. The method of claim 8, wherein the lymphoblastic leukemia is B-cell acute lymphoblastic leukemia (B-ALL).

* * * * *

SEQUENCE LISTING

```
<160> NUMBER OF SEQ ID NOS: 184

<210> SEQ ID NO 1
<211> LENGTH: 8
<212> TYPE: PRT
<213> ORGANISM: Homo sapiens

<400> SEQUENCE: 1

Asn Glu Gln Thr Thr Ile Leu Tyr
1               5


<210> SEQ ID NO 2
<211> LENGTH: 9
<212> TYPE: PRT
<213> ORGANISM: Homo sapiens

<400> SEQUENCE: 2

Ala Leu Phe Ser Asn Glu Val Ser Leu
1               5


<210> SEQ ID NO 3
<211> LENGTH: 9
<212> TYPE: PRT
<213> ORGANISM: Homo sapiens

<400> SEQUENCE: 3

Phe Ile Pro Asp Leu Phe Thr Glu Leu
1               5


<210> SEQ ID NO 4
<211> LENGTH: 9
<212> TYPE: PRT
<213> ORGANISM: Homo sapiens

<400> SEQUENCE: 4

Phe Leu Leu Asp His Ile Leu Thr Ile
1               5


<210> SEQ ID NO 5
<211> LENGTH: 9
<212> TYPE: PRT
<213> ORGANISM: Homo sapiens

<400> SEQUENCE: 5

Phe Leu Leu Glu Ser Arg Glu Thr Leu
1               5


<210> SEQ ID NO 6
<211> LENGTH: 9
```

<212> TYPE: PRT
<213> ORGANISM: Homo sapiens

<400> SEQUENCE: 6

Phe Leu Leu Pro Thr Ser Leu Ser Leu
1 5

<210> SEQ ID NO 7
<211> LENGTH: 9
<212> TYPE: PRT
<213> ORGANISM: Homo sapiens

<400> SEQUENCE: 7

Phe Leu Leu Ser Asp Glu Leu Leu Leu
1 5

<210> SEQ ID NO 8
<211> LENGTH: 9
<212> TYPE: PRT
<213> ORGANISM: Homo sapiens

<400> SEQUENCE: 8

Gly Leu Ala Thr Ala Val Trp Leu Leu
1 5

<210> SEQ ID NO 9
<211> LENGTH: 9
<212> TYPE: PRT
<213> ORGANISM: Homo sapiens

<400> SEQUENCE: 9

Gly Leu Leu Thr Ala Ser Ile Phe Leu
1 5

<210> SEQ ID NO 10
<211> LENGTH: 9
<212> TYPE: PRT
<213> ORGANISM: Homo sapiens

<400> SEQUENCE: 10

Gly Thr Leu Cys Leu Leu Thr Phe Ile
1 5

<210> SEQ ID NO 11
<211> LENGTH: 9
<212> TYPE: PRT
<213> ORGANISM: Homo sapiens

<400> SEQUENCE: 11

Lys Leu Leu Gln Pro Leu Pro Ile Thr
1 5

<210> SEQ ID NO 12
<211> LENGTH: 9
<212> TYPE: PRT
<213> ORGANISM: Homo sapiens

<400> SEQUENCE: 12

Leu Leu Gln Asn Leu Ile Val Leu Leu
1 5

<210> SEQ ID NO 13
<211> LENGTH: 9
<212> TYPE: PRT
<213> ORGANISM: Homo sapiens

<400> SEQUENCE: 13

Leu Leu Ser Leu Tyr Leu Val Ser Ile
1 5

<210> SEQ ID NO 14
<211> LENGTH: 9
<212> TYPE: PRT
<213> ORGANISM: Homo sapiens

<400> SEQUENCE: 14

Leu Met Leu Leu Phe Val Val Leu Leu
1 5

<210> SEQ ID NO 15
<211> LENGTH: 9
<212> TYPE: PRT
<213> ORGANISM: Homo sapiens

<400> SEQUENCE: 15

Ser Leu Ala Asn Glu Thr His Thr Leu
1 5

<210> SEQ ID NO 16
<211> LENGTH: 9
<212> TYPE: PRT
<213> ORGANISM: Homo sapiens

<400> SEQUENCE: 16

Val Leu Leu Asp Phe Pro Ala Leu Leu
1 5

<210> SEQ ID NO 17
<211> LENGTH: 9
<212> TYPE: PRT
<213> ORGANISM: Homo sapiens

<400> SEQUENCE: 17

Val Leu Leu Ser Lys Ile Leu Tyr Pro
1 5

<210> SEQ ID NO 18
<211> LENGTH: 9
<212> TYPE: PRT
<213> ORGANISM: Homo sapiens

<400> SEQUENCE: 18

Trp Leu Val Glu Lys Leu Ser Gly Val
1 5

<210> SEQ ID NO 19
<211> LENGTH: 9
<212> TYPE: PRT
<213> ORGANISM: Homo sapiens

<400> SEQUENCE: 19

Tyr Leu Phe Ala His Ser Ile Ile Leu
1 5

<210> SEQ ID NO 20
<211> LENGTH: 8
<212> TYPE: PRT
<213> ORGANISM: Homo sapiens

<400> SEQUENCE: 20

Tyr Leu Gly Tyr Ala Val Ala Val
1 5

<210> SEQ ID NO 21
<211> LENGTH: 9
<212> TYPE: PRT
<213> ORGANISM: Homo sapiens

<400> SEQUENCE: 21

Tyr Leu Gln Glu Ile Ser Leu Arg Leu
1 5

<210> SEQ ID NO 22
<211> LENGTH: 9
<212> TYPE: PRT
<213> ORGANISM: Homo sapiens

<400> SEQUENCE: 22

Ser Leu Leu Gly Ile Gly Leu Leu Ala
1 5

<210> SEQ ID NO 23
<211> LENGTH: 10
<212> TYPE: PRT
<213> ORGANISM: Homo sapiens

<400> SEQUENCE: 23

Ala Ala Met Glu Ser Pro Ile Gln Ser Lys
1 5 10

<210> SEQ ID NO 24
<211> LENGTH: 11
<212> TYPE: PRT
<213> ORGANISM: Homo sapiens

<400> SEQUENCE: 24

Ala Leu Phe Gly Phe Val Gly Phe Pro Asn Lys
1 5 10

<210> SEQ ID NO 25
<211> LENGTH: 9
<212> TYPE: PRT
<213> ORGANISM: Homo sapiens

<400> SEQUENCE: 25

Ala Leu Phe Val Leu Thr Ser Ile Lys
1 5

<210> SEQ ID NO 26
<211> LENGTH: 9
<212> TYPE: PRT
<213> ORGANISM: Homo sapiens

<400> SEQUENCE: 26

Ala Thr Ser Leu Thr Ile Gln Glu Lys
1 5

<210> SEQ ID NO 27
<211> LENGTH: 9
<212> TYPE: PRT
<213> ORGANISM: Homo sapiens

<400> SEQUENCE: 27

Ala Val Ala Val Pro Leu Leu Pro Arg

```
1               5


<210> SEQ ID NO 28
<211> LENGTH: 9
<212> TYPE: PRT
<213> ORGANISM: Homo sapiens

<400> SEQUENCE: 28

Gly Thr Ile Ser Gly Gly Phe Phe Lys
1               5


<210> SEQ ID NO 29
<211> LENGTH: 8
<212> TYPE: PRT
<213> ORGANISM: Homo sapiens

<400> SEQUENCE: 29

Gly Val Ala Asn Ser Leu Leu Lys
1               5


<210> SEQ ID NO 30
<211> LENGTH: 9
<212> TYPE: PRT
<213> ORGANISM: Homo sapiens

<400> SEQUENCE: 30

Gly Val Ser Pro Val Leu Phe Leu Lys
1               5


<210> SEQ ID NO 31
<211> LENGTH: 9
<212> TYPE: PRT
<213> ORGANISM: Homo sapiens

<400> SEQUENCE: 31

Leu Leu Gly Leu Pro Gln Pro Pro Lys
1               5


<210> SEQ ID NO 32
<211> LENGTH: 9
<212> TYPE: PRT
<213> ORGANISM: Homo sapiens

<400> SEQUENCE: 32

Leu Ser Ser Arg Leu Pro Leu Gly Lys
1               5


<210> SEQ ID NO 33
<211> LENGTH: 9
<212> TYPE: PRT
<213> ORGANISM: Homo sapiens

<400> SEQUENCE: 33

Asn Leu Leu Phe Ser Arg Val Phe Lys
1               5


<210> SEQ ID NO 34
<211> LENGTH: 9
<212> TYPE: PRT
<213> ORGANISM: Homo sapiens

<400> SEQUENCE: 34

Ser Thr Gly Val Leu Thr Val Leu Lys
1               5
```

<210> SEQ ID NO 35
<211> LENGTH: 9
<212> TYPE: PRT
<213> ORGANISM: Homo sapiens

<400> SEQUENCE: 35

Ser Val Phe Asp Arg Thr Asn Asn Arg
1               5

<210> SEQ ID NO 36
<211> LENGTH: 9
<212> TYPE: PRT
<213> ORGANISM: Homo sapiens

<400> SEQUENCE: 36

Ser Val Val Pro His Pro Leu Gln Lys
1               5

<210> SEQ ID NO 37
<211> LENGTH: 9
<212> TYPE: PRT
<213> ORGANISM: Homo sapiens

<400> SEQUENCE: 37

Thr Thr Ser Ser Ile Tyr Ile Arg Lys
1               5

<210> SEQ ID NO 38
<211> LENGTH: 9
<212> TYPE: PRT
<213> ORGANISM: Homo sapiens

<400> SEQUENCE: 38

Leu Tyr Thr Phe Ile Lys His Glu Phe
1               5

<210> SEQ ID NO 39
<211> LENGTH: 10
<212> TYPE: PRT
<213> ORGANISM: Homo sapiens

<400> SEQUENCE: 39

Ser Tyr Phe Asp Pro Ser Tyr Ser Asn Phe
1               5                   10

<210> SEQ ID NO 40
<211> LENGTH: 9
<212> TYPE: PRT
<213> ORGANISM: Homo sapiens

<400> SEQUENCE: 40

Ser Tyr Leu Ala Ser Phe Leu Leu Tyr
1               5

<210> SEQ ID NO 41
<211> LENGTH: 9
<212> TYPE: PRT
<213> ORGANISM: Homo sapiens

<400> SEQUENCE: 41

Val Tyr Ser Pro Ser Pro Leu Asn Phe
1               5

<210> SEQ ID NO 42

<211> LENGTH: 8
<212> TYPE: PRT
<213> ORGANISM: Homo sapiens

<400> SEQUENCE: 42

Val Tyr Thr Gln Val Ser Ala Phe
1 5

<210> SEQ ID NO 43
<211> LENGTH: 8
<212> TYPE: PRT
<213> ORGANISM: Homo sapiens

<400> SEQUENCE: 43

Tyr Ser Val Leu Thr Val Thr Phe
1 5

<210> SEQ ID NO 44
<211> LENGTH: 8
<212> TYPE: PRT
<213> ORGANISM: Homo sapiens

<400> SEQUENCE: 44

Asn Leu Gly Leu Phe Leu Ser Tyr
1 5

<210> SEQ ID NO 45
<211> LENGTH: 9
<212> TYPE: PRT
<213> ORGANISM: Homo sapiens

<400> SEQUENCE: 45

Ala Val Gly Gly Phe Arg Ser Ser Trp
1 5

<210> SEQ ID NO 46
<211> LENGTH: 10
<212> TYPE: PRT
<213> ORGANISM: Homo sapiens

<400> SEQUENCE: 46

Ser Gln Val Gln Ala Val Leu Leu Ala Trp
1 5 10

<210> SEQ ID NO 47
<211> LENGTH: 9
<212> TYPE: PRT
<213> ORGANISM: Homo sapiens

<400> SEQUENCE: 47

Gln Thr Asn Ser Gly Ser Leu Ala Arg
1 5

<210> SEQ ID NO 48
<211> LENGTH: 9
<212> TYPE: PRT
<213> ORGANISM: Homo sapiens

<400> SEQUENCE: 48

Asp Val Ala Gly Val Gly Met Pro Lys
1 5

<210> SEQ ID NO 49
<211> LENGTH: 9
<212> TYPE: PRT

<213> ORGANISM: Homo sapiens

<400> SEQUENCE: 49

Asp Val Met Ala Ser Leu Ala Arg Val
1 5

<210> SEQ ID NO 50
<211> LENGTH: 9
<212> TYPE: PRT
<213> ORGANISM: Homo sapiens

<400> SEQUENCE: 50

Glu Val Gly Ala Val Phe Ala Val Leu
1 5

<210> SEQ ID NO 51
<211> LENGTH: 9
<212> TYPE: PRT
<213> ORGANISM: Homo sapiens

<400> SEQUENCE: 51

Val Val Ala Asp Ile Leu Leu Ser Val
1 5

<210> SEQ ID NO 52
<211> LENGTH: 10
<212> TYPE: PRT
<213> ORGANISM: Homo sapiens

<400> SEQUENCE: 52

Ser Ser Leu Ser Gly Pro Val Ser Ser Leu
1 5 10

<210> SEQ ID NO 53
<211> LENGTH: 8
<212> TYPE: PRT
<213> ORGANISM: Homo sapiens

<400> SEQUENCE: 53

Ala Phe Arg Val Ile Val Ala Leu
1 5

<210> SEQ ID NO 54
<211> LENGTH: 9
<212> TYPE: PRT
<213> ORGANISM: Homo sapiens

<400> SEQUENCE: 54

Glu His Tyr Asn Lys Val Val Val Met
1 5

<210> SEQ ID NO 55
<211> LENGTH: 9
<212> TYPE: PRT
<213> ORGANISM: Homo sapiens

<400> SEQUENCE: 55

Val Gln Ala Gln Val Leu Glu Ala Ile
1 5

<210> SEQ ID NO 56
<211> LENGTH: 9
<212> TYPE: PRT
<213> ORGANISM: Homo sapiens

<400> SEQUENCE: 56

Asn Asn Met Ala Ile Ile Tyr Ser Tyr
1 5

<210> SEQ ID NO 57
<211> LENGTH: 9
<212> TYPE: PRT
<213> ORGANISM: Homo sapiens

<400> SEQUENCE: 57

Glu Pro Ser His Ser Ile Asn Val Tyr
1 5

<210> SEQ ID NO 58
<211> LENGTH: 11
<212> TYPE: PRT
<213> ORGANISM: Homo sapiens

<400> SEQUENCE: 58

Ile Pro Val Gly Ser Gly Leu Gly Tyr Val Leu
1 5 10

<210> SEQ ID NO 59
<211> LENGTH: 9
<212> TYPE: PRT
<213> ORGANISM: Homo sapiens

<400> SEQUENCE: 59

Asp His Asp Ile Gly Val Tyr Ser Val
1 5

<210> SEQ ID NO 60
<211> LENGTH: 8
<212> TYPE: PRT
<213> ORGANISM: Homo sapiens

<400> SEQUENCE: 60

His Phe Glu Trp Gln Pro Pro Leu
1 5

<210> SEQ ID NO 61
<211> LENGTH: 9
<212> TYPE: PRT
<213> ORGANISM: Homo sapiens

<400> SEQUENCE: 61

Gly Glu Phe Leu Val Pro Leu Ser Leu
1 5

<210> SEQ ID NO 62
<211> LENGTH: 10
<212> TYPE: PRT
<213> ORGANISM: Homo sapiens

<400> SEQUENCE: 62

Gly Glu Val Asp Gly Ala Gln Gln Ala Met
1 5 10

<210> SEQ ID NO 63
<211> LENGTH: 9
<212> TYPE: PRT
<213> ORGANISM: Homo sapiens

<400> SEQUENCE: 63

```
Ile Glu Glu Val Ser Gln Gly Leu Leu
1               5


<210> SEQ ID NO 64
<211> LENGTH: 11
<212> TYPE: PRT
<213> ORGANISM: Homo sapiens

<400> SEQUENCE: 64

Ile Glu Ser Glu Asp Phe Gly Phe Trp Ser Leu
1               5                   10


<210> SEQ ID NO 65
<211> LENGTH: 9
<212> TYPE: PRT
<213> ORGANISM: Homo sapiens

<400> SEQUENCE: 65

Leu Glu Asn Ser Gly Phe Ile Leu Ile
1               5


<210> SEQ ID NO 66
<211> LENGTH: 10
<212> TYPE: PRT
<213> ORGANISM: Homo sapiens

<400> SEQUENCE: 66

Arg Glu Pro Leu Glu Ile Leu Ile Thr Leu
1               5                   10


<210> SEQ ID NO 67
<211> LENGTH: 9
<212> TYPE: PRT
<213> ORGANISM: Homo sapiens

<400> SEQUENCE: 67

Glu Glu Thr Asp Ala Tyr Lys Ser Leu
1               5


<210> SEQ ID NO 68
<211> LENGTH: 9
<212> TYPE: PRT
<213> ORGANISM: Homo sapiens

<400> SEQUENCE: 68

Ser Glu Leu Gln Leu Pro Val Thr Phe
1               5


<210> SEQ ID NO 69
<211> LENGTH: 9
<212> TYPE: PRT
<213> ORGANISM: Homo sapiens

<400> SEQUENCE: 69

Gln Glu Ile Ala Thr Ser His Asn Ile
1               5


<210> SEQ ID NO 70
<211> LENGTH: 8
<212> TYPE: PRT
<213> ORGANISM: Homo sapiens

<400> SEQUENCE: 70

Ala Gln Phe Leu Leu Phe Ile Ala
1               5
```

<210> SEQ ID NO 71
<211> LENGTH: 9
<212> TYPE: PRT
<213> ORGANISM: Homo sapiens

<400> SEQUENCE: 71

Phe Glu Ile Ser Ser Val Thr Thr Ala
1               5

<210> SEQ ID NO 72
<211> LENGTH: 9
<212> TYPE: PRT
<213> ORGANISM: Homo sapiens

<400> SEQUENCE: 72

Lys Glu Val Gly Gly Leu Arg Ser Ala
1               5

<210> SEQ ID NO 73
<211> LENGTH: 8
<212> TYPE: PRT
<213> ORGANISM: Homo sapiens

<400> SEQUENCE: 73

Thr Glu Phe Gly Pro Val Ile Gly
1               5

<210> SEQ ID NO 74
<211> LENGTH: 9
<212> TYPE: PRT
<213> ORGANISM: Homo sapiens

<400> SEQUENCE: 74

Ile Ser Leu Pro Ala Leu Glu Val Leu
1               5

<210> SEQ ID NO 75
<211> LENGTH: 10
<212> TYPE: PRT
<213> ORGANISM: Homo sapiens

<400> SEQUENCE: 75

Leu Pro Ser Pro Pro Leu Pro Pro Ser Leu
1               5                   10

<210> SEQ ID NO 76
<211> LENGTH: 9
<212> TYPE: PRT
<213> ORGANISM: Homo sapiens

<400> SEQUENCE: 76

Leu Tyr Leu Pro Ser Val Val Leu Ile
1               5

<210> SEQ ID NO 77
<211> LENGTH: 10
<212> TYPE: PRT
<213> ORGANISM: Homo sapiens

<400> SEQUENCE: 77

Arg Pro Pro Ala Pro Leu Leu Pro Val Leu
1               5                   10

<210> SEQ ID NO 78
<211> LENGTH: 8
<212> TYPE: PRT
<213> ORGANISM: Homo sapiens

<400> SEQUENCE: 78

Ser Leu His Tyr Ser Val Ser Leu
1 5

<210> SEQ ID NO 79
<211> LENGTH: 9
<212> TYPE: PRT
<213> ORGANISM: Homo sapiens

<400> SEQUENCE: 79

Ser Leu Pro Asp His Gln Gly Val Leu
1 5

<210> SEQ ID NO 80
<211> LENGTH: 9
<212> TYPE: PRT
<213> ORGANISM: Homo sapiens

<400> SEQUENCE: 80

Glu Ala Val Ser Gln Gly Lys Asp Phe
1 5

<210> SEQ ID NO 81
<211> LENGTH: 9
<212> TYPE: PRT
<213> ORGANISM: Homo sapiens

<400> SEQUENCE: 81

Tyr Ser Ser Tyr Leu Ser Ile His Tyr
1 5

<210> SEQ ID NO 82
<211> LENGTH: 9
<212> TYPE: PRT
<213> ORGANISM: Homo sapiens

<400> SEQUENCE: 82

Ala Ser Leu Gly Leu Ser Leu Ala Leu
1 5

<210> SEQ ID NO 83
<211> LENGTH: 9
<212> TYPE: PRT
<213> ORGANISM: Homo sapiens

<400> SEQUENCE: 83

Leu Cys His Arg Thr Pro Pro Ser Leu
1 5

<210> SEQ ID NO 84
<211> LENGTH: 9
<212> TYPE: PRT
<213> ORGANISM: Homo sapiens

<400> SEQUENCE: 84

Leu Ser Ile Ser Pro Phe Gln Ala Ile
1 5

<210> SEQ ID NO 85
<211> LENGTH: 9

<212> TYPE: PRT
<213> ORGANISM: Homo sapiens

<400> SEQUENCE: 85

Gly Trp Gly Gly Ser Pro Leu Tyr Leu
1 5

<210> SEQ ID NO 86
<211> LENGTH: 9
<212> TYPE: PRT
<213> ORGANISM: Homo sapiens

<400> SEQUENCE: 86

Tyr Phe Asp Pro Ser Tyr Ser Asn Phe
1 5

<210> SEQ ID NO 87
<211> LENGTH: 9
<212> TYPE: PRT
<213> ORGANISM: Homo sapiens

<400> SEQUENCE: 87

Ile Ser Leu Ser Ser Ile Val Ser Val
1 5

<210> SEQ ID NO 88
<211> LENGTH: 9
<212> TYPE: PRT
<213> ORGANISM: Homo sapiens

<400> SEQUENCE: 88

Leu Ser Ile Ser Ser Leu Val Ser Val
1 5

<210> SEQ ID NO 89
<211> LENGTH: 9
<212> TYPE: PRT
<213> ORGANISM: Homo sapiens

<400> SEQUENCE: 89

Ser Leu Thr Ala Leu Val Phe His Val
1 5

<210> SEQ ID NO 90
<211> LENGTH: 9
<212> TYPE: PRT
<213> ORGANISM: Homo sapiens

<400> SEQUENCE: 90

Arg Ile Phe Gly Phe Arg Leu Trp Lys
1 5

<210> SEQ ID NO 91
<211> LENGTH: 9
<212> TYPE: PRT
<213> ORGANISM: Homo sapiens

<400> SEQUENCE: 91

Thr Ser Phe Ala Glu Thr Trp Met Lys
1 5

<210> SEQ ID NO 92
<211> LENGTH: 9
<212> TYPE: PRT
<213> ORGANISM: Homo sapiens

<400> SEQUENCE: 92

Ile Pro Leu Asn Pro Phe Ser Ser Leu
1               5

<210> SEQ ID NO 93
<211> LENGTH: 24
<212> TYPE: DNA
<213> ORGANISM: Homo sapiens

<400> SEQUENCE: 93
aatgaacaga ctaccatttt gtac 24

<210> SEQ ID NO 94
<211> LENGTH: 27
<212> TYPE: DNA
<213> ORGANISM: Homo sapiens

<400> SEQUENCE: 94
gcacttttta gcaatgaagt gtctttg 27

<210> SEQ ID NO 95
<211> LENGTH: 27
<212> TYPE: DNA
<213> ORGANISM: Homo sapiens

<400> SEQUENCE: 95
ttcatcccag atctatttac agaatta 27

<210> SEQ ID NO 96
<211> LENGTH: 27
<212> TYPE: DNA
<213> ORGANISM: Homo sapiens

<400> SEQUENCE: 96
tttcttttgg atcacatatt gaccatt 27

<210> SEQ ID NO 97
<211> LENGTH: 27
<212> TYPE: DNA
<213> ORGANISM: Homo sapiens

<400> SEQUENCE: 97
ttcctattgg agtccaggga aacttta 27

<210> SEQ ID NO 98
<211> LENGTH: 27
<212> TYPE: DNA
<213> ORGANISM: Homo sapiens

<400> SEQUENCE: 98
ttcttgcttc caacttcact ttctttg 27

<210> SEQ ID NO 99
<211> LENGTH: 26
<212> TYPE: DNA
<213> ORGANISM: Homo sapiens

<400> SEQUENCE: 99
tttcttctct ctgatgaact tctttt 26

<210> SEQ ID NO 100
<211> LENGTH: 27

```
<212> TYPE: DNA
<213> ORGANISM: Homo sapiens

<400> SEQUENCE: 100

gggctggcca cagccgtgtg gctgctc                                          27


<210> SEQ ID NO 101
<211> LENGTH: 27
<212> TYPE: DNA
<213> ORGANISM: Homo sapiens

<400> SEQUENCE: 101

ggattattaa cggcatccat tttcttg                                          27


<210> SEQ ID NO 102
<211> LENGTH: 27
<212> TYPE: DNA
<213> ORGANISM: Homo sapiens

<400> SEQUENCE: 102

ggtaccttgt gcctattaac tttcatt                                          27


<210> SEQ ID NO 103
<211> LENGTH: 27
<212> TYPE: DNA
<213> ORGANISM: Homo sapiens

<400> SEQUENCE: 103

aaactcctcc aacctctgcc cattacc                                          27


<210> SEQ ID NO 104
<211> LENGTH: 27
<212> TYPE: DNA
<213> ORGANISM: Homo sapiens

<400> SEQUENCE: 104

cttcttcaaa atttaatagt gctgtta                                          27


<210> SEQ ID NO 105
<211> LENGTH: 27
<212> TYPE: DNA
<213> ORGANISM: Homo sapiens

<400> SEQUENCE: 105

ctcttaagtt tgtatttagt aagtata                                          27


<210> SEQ ID NO 106
<211> LENGTH: 27
<212> TYPE: DNA
<213> ORGANISM: Homo sapiens

<400> SEQUENCE: 106

ttaatgttac tctttgtcgt attacta                                          27


<210> SEQ ID NO 107
<211> LENGTH: 27
<212> TYPE: DNA
<213> ORGANISM: Homo sapiens

<400> SEQUENCE: 107

tctttggcca acgagaccca caccctt                                          27


<210> SEQ ID NO 108
```

<211> LENGTH: 27
<212> TYPE: DNA
<213> ORGANISM: Homo sapiens

<400> SEQUENCE: 108
gtactgttgg actttccggc tctgtta 27

<210> SEQ ID NO 109
<211> LENGTH: 27
<212> TYPE: DNA
<213> ORGANISM: Homo sapiens

<400> SEQUENCE: 109
gttttacttt caaaaatact atatcca 27

<210> SEQ ID NO 110
<211> LENGTH: 27
<212> TYPE: DNA
<213> ORGANISM: Homo sapiens

<400> SEQUENCE: 110
tggttggtgg agaagctcag tggtgtg 27

<210> SEQ ID NO 111
<211> LENGTH: 27
<212> TYPE: DNA
<213> ORGANISM: Homo sapiens

<400> SEQUENCE: 111
tacttgtttg cacattccat tatctta 27

<210> SEQ ID NO 112
<211> LENGTH: 24
<212> TYPE: DNA
<213> ORGANISM: Homo sapiens

<400> SEQUENCE: 112
tacctgggtt acgctgtggc cgtg 24

<210> SEQ ID NO 113
<211> LENGTH: 27
<212> TYPE: DNA
<213> ORGANISM: Homo sapiens

<400> SEQUENCE: 113
tatctgcaag aaatatcatt aagatta 27

<210> SEQ ID NO 114
<211> LENGTH: 27
<212> TYPE: DNA
<213> ORGANISM: Homo sapiens

<400> SEQUENCE: 114
agtcttttag gaataggatt gttggca 27

<210> SEQ ID NO 115
<211> LENGTH: 30
<212> TYPE: DNA
<213> ORGANISM: Homo sapiens

<400> SEQUENCE: 115
gcagccatgg agtctcctat acagtccaag 30

<210> SEQ ID NO 116
<211> LENGTH: 33
<212> TYPE: DNA
<213> ORGANISM: Homo sapiens

<400> SEQUENCE: 116
gccctatttg gttttgttgg attccccaac aag 33

<210> SEQ ID NO 117
<211> LENGTH: 27
<212> TYPE: DNA
<213> ORGANISM: Homo sapiens

<400> SEQUENCE: 117
gcactgtttg tgttaacatc aataaaa 27

<210> SEQ ID NO 118
<211> LENGTH: 27
<212> TYPE: DNA
<213> ORGANISM: Homo sapiens

<400> SEQUENCE: 118
gctacaagtc tcaccatcca ggaaaaa 27

<210> SEQ ID NO 119
<211> LENGTH: 27
<212> TYPE: DNA
<213> ORGANISM: Homo sapiens

<400> SEQUENCE: 119
gctgtagcag ttcccctcct gcctagg 27

<210> SEQ ID NO 120
<211> LENGTH: 27
<212> TYPE: DNA
<213> ORGANISM: Homo sapiens

<400> SEQUENCE: 120
ggaactatat caggtggctt cttcaaa 27

<210> SEQ ID NO 121
<211> LENGTH: 24
<212> TYPE: DNA
<213> ORGANISM: Homo sapiens

<400> SEQUENCE: 121
ggtgtggcca atagtctttt aaaa 24

<210> SEQ ID NO 122
<211> LENGTH: 27
<212> TYPE: DNA
<213> ORGANISM: Homo sapiens

<400> SEQUENCE: 122
ggcgtctctc ctgtgttatt tctaaag 27

<210> SEQ ID NO 123
<211> LENGTH: 27
<212> TYPE: DNA
<213> ORGANISM: Homo sapiens

<400> SEQUENCE: 123
cttctgggct tgcctcagcc tcctaaa 27

<210> SEQ ID NO 124
<211> LENGTH: 27
<212> TYPE: DNA
<213> ORGANISM: Homo sapiens

<400> SEQUENCE: 124
ctgtcttcaa gactgccact ggggaag 27

<210> SEQ ID NO 125
<211> LENGTH: 27
<212> TYPE: DNA
<213> ORGANISM: Homo sapiens

<400> SEQUENCE: 125
aaccttctgt ttagtagagt ttttaag 27

<210> SEQ ID NO 126
<211> LENGTH: 27
<212> TYPE: DNA
<213> ORGANISM: Homo sapiens

<400> SEQUENCE: 126
tcaactggag tcctcactgt gctaaag 27

<210> SEQ ID NO 127
<211> LENGTH: 27
<212> TYPE: DNA
<213> ORGANISM: Homo sapiens

<400> SEQUENCE: 127
agtgtctttg acaggaccaa taaccgt 27

<210> SEQ ID NO 128
<211> LENGTH: 27
<212> TYPE: DNA
<213> ORGANISM: Homo sapiens

<400> SEQUENCE: 128
tcagtagtgc ctcatcccct tcaaaag 27

<210> SEQ ID NO 129
<211> LENGTH: 27
<212> TYPE: DNA
<213> ORGANISM: Homo sapiens

<400> SEQUENCE: 129
acaaccagtt caatctacat aagaaag 27

<210> SEQ ID NO 130
<211> LENGTH: 27
<212> TYPE: DNA
<213> ORGANISM: Homo sapiens

<400> SEQUENCE: 130
ttgtacacat ttataaaaca tgaattc 27

<210> SEQ ID NO 131
<211> LENGTH: 30
<212> TYPE: DNA
<213> ORGANISM: Homo sapiens

<400> SEQUENCE: 131
tcctactttg atccttcgta cagcaatttt 30

<210> SEQ ID NO 132
<211> LENGTH: 27
<212> TYPE: DNA
<213> ORGANISM: Homo sapiens

<400> SEQUENCE: 132
tcatacctgg catctttctt gttgtac 27

<210> SEQ ID NO 133
<211> LENGTH: 27
<212> TYPE: DNA
<213> ORGANISM: Homo sapiens

<400> SEQUENCE: 133
gtatattctc caagcccatt gaatttc 27

<210> SEQ ID NO 134
<211> LENGTH: 24
<212> TYPE: DNA
<213> ORGANISM: Homo sapiens

<400> SEQUENCE: 134
gtgtacacgc aggtgtccgc cttt 24

<210> SEQ ID NO 135
<211> LENGTH: 24
<212> TYPE: DNA
<213> ORGANISM: Homo sapiens

<400> SEQUENCE: 135
tattctgttc taacagtaac tttt 24

<210> SEQ ID NO 136
<211> LENGTH: 24
<212> TYPE: DNA
<213> ORGANISM: Homo sapiens

<400> SEQUENCE: 136
aatctggggc tttttctctc atac 24

<210> SEQ ID NO 137
<211> LENGTH: 27
<212> TYPE: DNA
<213> ORGANISM: Homo sapiens

<400> SEQUENCE: 137
gccgtgggag gcttcaggag cagctgg 27

<210> SEQ ID NO 138
<211> LENGTH: 30
<212> TYPE: DNA
<213> ORGANISM: Homo sapiens

<400> SEQUENCE: 138
tcacaggttc aagcagttct cctagcttgg 30

<210> SEQ ID NO 139
<211> LENGTH: 27
<212> TYPE: DNA
<213> ORGANISM: Homo sapiens

<400> SEQUENCE: 139
cagacaaaca gtggatctct cgccaga 27

<210> SEQ ID NO 140
<211> LENGTH: 27
<212> TYPE: DNA
<213> ORGANISM: Homo sapiens

<400> SEQUENCE: 140
gacgtggcag gagttggcat gcccaag 27

<210> SEQ ID NO 141
<211> LENGTH: 27
<212> TYPE: DNA
<213> ORGANISM: Homo sapiens

<400> SEQUENCE: 141
gatgtgatgg cctccctcgc cagagtc 27

<210> SEQ ID NO 142
<211> LENGTH: 27
<212> TYPE: DNA
<213> ORGANISM: Homo sapiens

<400> SEQUENCE: 142
gaagtgggag ccgtgtttgc tgtctta 27

<210> SEQ ID NO 143
<211> LENGTH: 27
<212> TYPE: DNA
<213> ORGANISM: Homo sapiens

<400> SEQUENCE: 143
gtggttgccg acatcctgct gtctgtg 27

<210> SEQ ID NO 144
<211> LENGTH: 30
<212> TYPE: DNA
<213> ORGANISM: Homo sapiens

<400> SEQUENCE: 144
tcatctctga gtggtccagt gagctcgctg 30

<210> SEQ ID NO 145
<211> LENGTH: 24
<212> TYPE: DNA
<213> ORGANISM: Homo sapiens

<400> SEQUENCE: 145
gcctttaggg ttattgttgc ttta 24

<210> SEQ ID NO 146
<211> LENGTH: 27
<212> TYPE: DNA
<213> ORGANISM: Homo sapiens

<400> SEQUENCE: 146
gaacactaca ataaagtagt ggtaatg 27

<210> SEQ ID NO 147
<211> LENGTH: 27
<212> TYPE: DNA
<213> ORGANISM: Homo sapiens

<400> SEQUENCE: 147
gtgcaagccc aggttttaga agccatc 27

<210> SEQ ID NO 148
<211> LENGTH: 27
<212> TYPE: DNA
<213> ORGANISM: Homo sapiens

<400> SEQUENCE: 148
aacaatatgg caataatcta ttcttat 27

<210> SEQ ID NO 149
<211> LENGTH: 27
<212> TYPE: DNA
<213> ORGANISM: Homo sapiens

<400> SEQUENCE: 149
gagccatccc attcaataaa tgtttat 27

<210> SEQ ID NO 150
<211> LENGTH: 33
<212> TYPE: DNA
<213> ORGANISM: Homo sapiens

<400> SEQUENCE: 150
atccccgttg gaagtggtct gggctacgtg ctg 33

<210> SEQ ID NO 151
<211> LENGTH: 27
<212> TYPE: DNA
<213> ORGANISM: Homo sapiens

<400> SEQUENCE: 151
gaccatgaca tcggtgtgta cagcgtc 27

<210> SEQ ID NO 152
<211> LENGTH: 24
<212> TYPE: DNA
<213> ORGANISM: Homo sapiens

<400> SEQUENCE: 152
cactttgagt ggcagccacc tctg 24

<210> SEQ ID NO 153
<211> LENGTH: 27
<212> TYPE: DNA
<213> ORGANISM: Homo sapiens

<400> SEQUENCE: 153
ggggagttcc ttgttcctct gtccctc 27

<210> SEQ ID NO 154
<211> LENGTH: 30
<212> TYPE: DNA
<213> ORGANISM: Homo sapiens

<400> SEQUENCE: 154
ggtgaagtgg atggggcaca gcaggcaatg 30

<210> SEQ ID NO 155
<211> LENGTH: 27
<212> TYPE: DNA
<213> ORGANISM: Homo sapiens

<400> SEQUENCE: 155
atagaggagg tgagccaggg gctgctc 27

<210> SEQ ID NO 156
<211> LENGTH: 33
<212> TYPE: DNA
<213> ORGANISM: Homo sapiens

<400> SEQUENCE: 156
atagagtcag aagactttgg attttggagt ctg 33

<210> SEQ ID NO 157
<211> LENGTH: 27
<212> TYPE: DNA
<213> ORGANISM: Homo sapiens

<400> SEQUENCE: 157
ctggagaata gtggatttat attaata 27

<210> SEQ ID NO 158
<211> LENGTH: 30
<212> TYPE: DNA
<213> ORGANISM: Homo sapiens

<400> SEQUENCE: 158
agagaaccat tggagatact cattactctt 30

<210> SEQ ID NO 159
<211> LENGTH: 27
<212> TYPE: DNA
<213> ORGANISM: Homo sapiens

<400> SEQUENCE: 159
gaagagacag atgcctacaa aagcctc 27

<210> SEQ ID NO 160
<211> LENGTH: 27
<212> TYPE: DNA
<213> ORGANISM: Homo sapiens

<400> SEQUENCE: 160
agtgaattac aactacctgt tactttc 27

<210> SEQ ID NO 161
<211> LENGTH: 27
<212> TYPE: DNA
<213> ORGANISM: Homo sapiens

<400> SEQUENCE: 161
caggagatag caacaagcca taatata 27

<210> SEQ ID NO 162
<211> LENGTH: 24
<212> TYPE: DNA
<213> ORGANISM: Homo sapiens

<400> SEQUENCE: 162
gcccaattcc ttctctttat tgca 24

<210> SEQ ID NO 163
<211> LENGTH: 27
<212> TYPE: DNA
<213> ORGANISM: Homo sapiens

<400> SEQUENCE: 163
tttgaaatca gctctgtaac cacagcc 27

<210> SEQ ID NO 164
<211> LENGTH: 27
<212> TYPE: DNA
<213> ORGANISM: Homo sapiens

<400> SEQUENCE: 164
aaagaggtgg gtgggcttag gtcagct 27

<210> SEQ ID NO 165
<211> LENGTH: 24
<212> TYPE: DNA
<213> ORGANISM: Homo sapiens

<400> SEQUENCE: 165
actgagtttg gtcctgtcat tggg 24

<210> SEQ ID NO 166
<211> LENGTH: 27
<212> TYPE: DNA
<213> ORGANISM: Homo sapiens

<400> SEQUENCE: 166
atatcccttc ctgctctaga ggttctg 27

<210> SEQ ID NO 167
<211> LENGTH: 30
<212> TYPE: DNA
<213> ORGANISM: Homo sapiens

<400> SEQUENCE: 167
ctcccctccc ctccccttcc tccctccctc 30

<210> SEQ ID NO 168
<211> LENGTH: 27
<212> TYPE: DNA
<213> ORGANISM: Homo sapiens

<400> SEQUENCE: 168
ttatatttgc cctctgttgt gctgatc 27

<210> SEQ ID NO 169
<211> LENGTH: 29
<212> TYPE: DNA
<213> ORGANISM: Homo sapiens

<400> SEQUENCE: 169
cggccaccag ctcctctgct ccctgtcct 29

<210> SEQ ID NO 170
<211> LENGTH: 24
<212> TYPE: DNA
<213> ORGANISM: Homo sapiens

<400> SEQUENCE: 170
tcactgcact actctgtctc ttta 24

<210> SEQ ID NO 171
<211> LENGTH: 27
<212> TYPE: DNA

<213> ORGANISM: Homo sapiens

<400> SEQUENCE: 171
agtctcccag atcaccaggg tgtctta 27

<210> SEQ ID NO 172
<211> LENGTH: 27
<212> TYPE: DNA
<213> ORGANISM: Homo sapiens

<400> SEQUENCE: 172
gaggcagttt cccaggggaa ggatttt 27

<210> SEQ ID NO 173
<211> LENGTH: 27
<212> TYPE: DNA
<213> ORGANISM: Homo sapiens

<400> SEQUENCE: 173
tattctagtt atttaagcat tcattat 27

<210> SEQ ID NO 174
<211> LENGTH: 27
<212> TYPE: DNA
<213> ORGANISM: Homo sapiens

<400> SEQUENCE: 174
gcctcactgg gcttaagctt ggctttg 27

<210> SEQ ID NO 175
<211> LENGTH: 27
<212> TYPE: DNA
<213> ORGANISM: Homo sapiens

<400> SEQUENCE: 175
ttgtgccacc gcactccacc cagcctg 27

<210> SEQ ID NO 176
<211> LENGTH: 27
<212> TYPE: DNA
<213> ORGANISM: Homo sapiens

<400> SEQUENCE: 176
ttatctattt ctccttttca ggctatc 27

<210> SEQ ID NO 177
<211> LENGTH: 27
<212> TYPE: DNA
<213> ORGANISM: Homo sapiens

<400> SEQUENCE: 177
gggtggggag ggagtccttt gtaccta 27

<210> SEQ ID NO 178
<211> LENGTH: 27
<212> TYPE: DNA
<213> ORGANISM: Homo sapiens

<400> SEQUENCE: 178
tactttgatc cttcgtacag caatttt 27

<210> SEQ ID NO 179
<211> LENGTH: 27

```
<212> TYPE: DNA
<213> ORGANISM: Homo sapiens

<400> SEQUENCE: 179

atttctctct cttctatagt ttctgta                                          27


<210> SEQ ID NO 180
<211> LENGTH: 27
<212> TYPE: DNA
<213> ORGANISM: Homo sapiens

<400> SEQUENCE: 180

ttatctattt cttctcttgt gagtgtt                                          27


<210> SEQ ID NO 181
<211> LENGTH: 27
<212> TYPE: DNA
<213> ORGANISM: Homo sapiens

<400> SEQUENCE: 181

tccctcacag cactagtatt tcatgtt                                          27


<210> SEQ ID NO 182
<211> LENGTH: 27
<212> TYPE: DNA
<213> ORGANISM: Homo sapiens

<400> SEQUENCE: 182

aggatttttg gctttcggct ctggaaa                                          27


<210> SEQ ID NO 183
<211> LENGTH: 27
<212> TYPE: DNA
<213> ORGANISM: Homo sapiens

<400> SEQUENCE: 183

acatcctttg cagagacatg gatgaaa                                          27


<210> SEQ ID NO 184
<211> LENGTH: 27
<212> TYPE: DNA
<213> ORGANISM: Homo sapiens

<400> SEQUENCE: 184

atacctttga atcctttcag ttctttg                                          27
```